United States Patent

Metzmaker et al.

(10) Patent No.: US 9,180,242 B2
(45) Date of Patent: Nov. 10, 2015

(54) METHODS AND DEVICES FOR MULTIPLE FLUID TRANSFER

(75) Inventors: Thomas Metzmaker, San Diego, CA (US); Sean Saint, San Diego, CA (US); Michael Michaud, San Diego, CA (US); Mike Rosinko, Anaheim, CA (US); Vance Swanson, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 732 days.

(21) Appl. No.: 13/474,032

(22) Filed: May 17, 2012

(65) Prior Publication Data

US 2013/0306191 A1 Nov. 21, 2013

(51) Int. Cl.
*A61M 5/14* (2006.01)
*A61M 5/168* (2006.01)
*A61M 39/02* (2006.01)
A61M 39/10 (2006.01)
A61J 1/20 (2006.01)

(52) U.S. Cl.
CPC .......... *A61M 5/1413* (2013.01); *A61M 5/16827* (2013.01); *A61M 39/02* (2013.01); *A61J 1/2096* (2013.01); *A61M 2039/1077* (2013.01); *A61M 2039/1094* (2013.01)

(58) Field of Classification Search
CPC .................. A61M 39/10; A61M 2039/1094; A61M 2039/1077; A61M 5/14244; B65B 3/003; B65B 3/006
USPC .......... 141/2, 9, 100, 104, 383, 386, 346–354; 604/151, 500
See application file for complete search history.

(56) References Cited

U.S. PATENT DOCUMENTS

| RE28,890 E | 7/1976 | Ingram et al. |
|---|---|---|
| 4,411,651 A | 10/1983 | Schulman |
| 4,491,155 A | 1/1985 | Meyer et al. |
| 4,636,226 A | 1/1987 | Canfora |
| 4,673,415 A | 6/1987 | Stanford |
| 4,678,460 A | 7/1987 | Rosner |
| 4,684,367 A | 8/1987 | Schaffer et al. |
| 4,685,903 A | 8/1987 | Cable et al. |
| 4,718,430 A | 1/1988 | Holzer |
| 4,976,162 A | 12/1990 | Kamen |
| 5,084,021 A | 1/1992 | Baldwin |
| 5,135,498 A | 8/1992 | Kam et al. |

(Continued)

FOREIGN PATENT DOCUMENTS

| EP | 560571 B1 | 5/1997 |
|---|---|---|
| WO | WO 9532013 A1 | 11/1995 |

(Continued)

OTHER PUBLICATIONS

Application and File history for U.S. Appl. No. 13/557,163, filed Jul. 24, 2012. Inventors: DiPerna et al.

(Continued)

*Primary Examiner* — Timothy L Maust
*Assistant Examiner* — Timothy P Kelly
(74) *Attorney, Agent, or Firm* — Patterson Thuente Pedersen, P.A.

(57) ABSTRACT

Devices and methods are disclosed for transferring multiple fluids from multiple supply reservoirs to multiple corresponding receptacle reservoirs. The devices and methods may be configured to prevent or reduce the incidence of a user transferring a fluid to an incorrect receptacle reservoir.

39 Claims, 30 Drawing Sheets

(56) References Cited

U.S. PATENT DOCUMENTS

| | | |
|---|---|---|
| 5,176,644 A | 1/1993 | Srisathapat et al. |
| 5,192,272 A | 3/1993 | Faure |
| 5,218,987 A | 6/1993 | Heil |
| 5,240,603 A | 8/1993 | Frank et al. |
| 5,322,418 A | 6/1994 | Comer |
| 5,322,626 A | 6/1994 | Frank et al. |
| 5,356,375 A | 10/1994 | Higley |
| 5,356,379 A | 10/1994 | Vaillancourt |
| 5,368,562 A | 11/1994 | Blomquist et al. |
| 5,438,510 A | 8/1995 | Bryant et al. |
| 5,441,027 A | 8/1995 | Buchanon et al. |
| 5,482,745 A | 1/1996 | Cuellar et al. |
| 5,492,534 A | 2/1996 | Athayde et al. |
| 5,527,307 A | 6/1996 | Srisathapat et al. |
| 5,615,671 A | 4/1997 | Schoonen et al. |
| 5,634,896 A | 6/1997 | Bryant et al. |
| 5,665,065 A | 9/1997 | Colman et al. |
| 5,702,384 A | 12/1997 | Umeyama et al. |
| 5,730,149 A | 3/1998 | Nakayama et al. |
| 5,785,688 A | 7/1998 | Joshi et al. |
| 5,830,175 A | 11/1998 | Flower |
| 5,891,097 A | 4/1999 | Saito et al. |
| 5,924,448 A | 7/1999 | West |
| 5,931,814 A | 8/1999 | Alex et al. |
| 5,954,685 A | 9/1999 | Tierney |
| 5,957,890 A | 9/1999 | Mann et al. |
| 5,988,165 A | 11/1999 | Richey, II et al. |
| 6,023,629 A | 2/2000 | Tamada |
| 6,065,279 A | 5/2000 | Kuromitsu et al. |
| 6,099,504 A | 8/2000 | Gross et al. |
| 6,144,869 A | 11/2000 | Berner et al. |
| 6,190,359 B1 | 2/2001 | Heruth |
| 6,202,708 B1 | 3/2001 | Bynum |
| 6,210,368 B1 | 4/2001 | Rogers |
| 6,248,093 B1 | 6/2001 | Moberg |
| 6,256,533 B1 | 7/2001 | Yuzhakov et al. |
| 6,261,272 B1 | 7/2001 | Gross et al. |
| 6,283,944 B1 | 9/2001 | McMullen et al. |
| 6,293,429 B2 | 9/2001 | Sadler et al. |
| 6,302,107 B1 | 10/2001 | Richey, II et al. |
| 6,306,420 B1 | 10/2001 | Cheikh |
| 6,331,172 B1 | 12/2001 | Epstein et al. |
| 6,341,232 B1 | 1/2002 | Conn et al. |
| 6,346,095 B1 | 2/2002 | Gross et al. |
| 6,366,808 B1 | 4/2002 | Schroeppel et al. |
| 6,374,876 B2 | 4/2002 | Bynum |
| 6,393,318 B1 | 5/2002 | Conn et al. |
| 6,394,981 B2 | 5/2002 | Heruth |
| 6,406,455 B1 | 6/2002 | Willis et al. |
| 6,409,698 B1 | 6/2002 | Robinson et al. |
| 6,438,414 B1 | 8/2002 | Conn et al. |
| 6,467,267 B2 | 10/2002 | Kanazawa et al. |
| 6,471,689 B1 | 10/2002 | Joseph et al. |
| 6,478,385 B2 | 11/2002 | Nishii et al. |
| 6,520,936 B1 | 2/2003 | Mann |
| 6,530,900 B1 | 3/2003 | Daily et al. |
| 6,537,268 B1 | 3/2003 | Gibson et al. |
| 6,550,245 B2 | 4/2003 | Nishii et al. |
| 6,562,001 B2 | 5/2003 | Lebel et al. |
| 6,571,128 B2 | 5/2003 | Lebel et al. |
| 6,572,566 B2 | 6/2003 | Effenhauser |
| 6,577,899 B2 | 6/2003 | Lebel et al. |
| 6,589,158 B2 | 7/2003 | Winkler |
| 6,589,229 B1 | 7/2003 | Connelly et al. |
| 6,594,514 B2 | 7/2003 | Berner et al. |
| 6,648,821 B2 | 11/2003 | Lebel et al. |
| 6,656,158 B2 | 12/2003 | Mahoney et al. |
| 6,656,159 B2 | 12/2003 | Flaherty et al. |
| 6,702,779 B2 | 3/2004 | Connelly et al. |
| 6,723,072 B2 | 4/2004 | Flaherty et al. |
| 6,738,663 B2 | 5/2004 | Schroeppel et al. |
| 6,767,188 B2 | 7/2004 | Vrane et al. |
| 6,805,122 B2 | 10/2004 | Richey, II et al. |
| 6,805,687 B2 | 10/2004 | Dextradeur et al. |
| 6,830,560 B1 | 12/2004 | Gross et al. |
| 6,854,432 B2 | 2/2005 | Hirano |
| 6,873,268 B2 | 3/2005 | Lebel et al. |
| 6,918,542 B2 | 7/2005 | Silverbrook et al. |
| 6,923,006 B2 | 8/2005 | Walton et al. |
| 6,923,180 B2 | 8/2005 | Richey, II et al. |
| 6,928,338 B1 | 8/2005 | Buchser et al. |
| 6,935,531 B1 | 8/2005 | Clayton |
| 6,948,918 B2 | 9/2005 | Hansen |
| 6,958,705 B2 | 10/2005 | Lebel et al. |
| 6,960,184 B2 | 11/2005 | Willis et al. |
| 6,974,115 B2 | 12/2005 | Silva |
| 6,974,437 B2 | 12/2005 | Lebel et al. |
| 6,979,315 B2 | 12/2005 | Rogers et al. |
| 7,008,403 B1 | 3/2006 | Mallett |
| 7,063,684 B2 | 6/2006 | Moberg |
| 7,073,713 B2 | 7/2006 | Silverbrook et al. |
| 7,083,108 B2 | 8/2006 | Silverbrook et al. |
| 7,092,011 B2 | 8/2006 | Silverbrook et al. |
| 7,097,104 B2 | 8/2006 | Silverbrook et al. |
| 7,163,520 B2 | 1/2007 | Bernard et al. |
| 7,187,404 B2 | 3/2007 | Silverbrook et al. |
| 7,193,521 B2 | 3/2007 | Moberg et al. |
| 7,201,319 B2 | 4/2007 | Silverbrook et al. |
| 7,201,730 B2 | 4/2007 | Davidner et al. |
| 7,207,964 B2 | 4/2007 | Davidner et al. |
| 7,225,807 B2 | 6/2007 | Papania et al. |
| 7,226,278 B2 | 6/2007 | Nason et al. |
| 7,234,645 B2 | 6/2007 | Silverbrook et al. |
| 7,289,142 B2 | 10/2007 | Silverbrook |
| 7,291,126 B2 | 11/2007 | Shekalim |
| 7,311,693 B2 | 12/2007 | Shekalim |
| 7,334,556 B2 | 2/2008 | Wachigai et al. |
| 7,341,581 B2 | 3/2008 | Mallett |
| 7,344,507 B2 | 3/2008 | Briggs et al. |
| 7,347,854 B2 | 3/2008 | Shelton et al. |
| 7,362,971 B2 | 4/2008 | Silverbrook et al. |
| 7,373,083 B2 | 5/2008 | Silverbrook et al. |
| 7,374,556 B2 | 5/2008 | Mallett |
| 7,377,706 B2 | 5/2008 | Silverbrook et al. |
| 7,407,490 B2 | 8/2008 | Bendsen et al. |
| 7,445,616 B2 | 11/2008 | Petrakis |
| 7,460,152 B2 | 12/2008 | Silverbrook et al. |
| 7,475,825 B2 | 1/2009 | Silverbrook et al. |
| 7,483,050 B2 | 1/2009 | Silverbrook et al. |
| 7,517,440 B2 | 4/2009 | Anex et al. |
| 7,524,045 B2 | 4/2009 | Silverbrook et al. |
| 7,530,968 B2 | 5/2009 | Gonnelli |
| 7,588,550 B2 | 9/2009 | Leonard et al. |
| 7,597,682 B2 | 10/2009 | Moberg |
| 7,605,710 B2 | 10/2009 | Crnkovich et al. |
| 7,621,893 B2 | 11/2009 | Moberg et al. |
| 7,654,127 B2 | 2/2010 | Krulevitch et al. |
| 7,662,140 B2 | 2/2010 | Heruth et al. |
| 7,678,071 B2 | 3/2010 | Lebel et al. |
| 7,713,240 B2 | 5/2010 | Istoc et al. |
| 7,726,955 B2 | 6/2010 | Ryser et al. |
| 7,766,873 B2 | 8/2010 | Moberg et al. |
| 7,794,434 B2 | 9/2010 | Mounce et al. |
| 7,811,262 B2 | 10/2010 | Moberg et al. |
| 7,811,279 B2 | 10/2010 | John |
| 7,828,764 B2 | 11/2010 | Moberg et al. |
| 7,831,310 B2 | 11/2010 | Lebel et al. |
| 7,849,872 B2 * | 12/2010 | Phillips et al. ................ 137/212 |
| 7,892,206 B2 | 2/2011 | Moberg et al. |
| 7,922,462 B2 | 4/2011 | Preuthun et al. |
| 7,935,104 B2 | 5/2011 | Yodfat et al. |
| 7,944,366 B2 | 5/2011 | Krulevitch et al. |
| 7,955,843 B2 | 6/2011 | Barringer, Jr. |
| 7,973,667 B2 | 7/2011 | Crnkovich et al. |
| 7,985,057 B2 | 7/2011 | Haar |
| 7,998,111 B2 | 8/2011 | Moberg et al. |
| 8,002,747 B2 | 8/2011 | Lord et al. |
| 8,007,487 B2 | 8/2011 | Patrick et al. |
| 8,016,789 B2 | 9/2011 | Grant et al. |
| 8,021,334 B2 | 9/2011 | Shekalim |
| 8,043,281 B2 | 10/2011 | Heruth et al. |
| 8,056,582 B2 | 11/2011 | DiPerna |
| 8,062,257 B2 | 11/2011 | Moberg et al. |
| 8,065,096 B2 | 11/2011 | Moberg et al. |

(56) References Cited

U.S. PATENT DOCUMENTS

| | | |
|---|---|---|
| 8,066,688 B2 | 11/2011 | Zinger et al. |
| 8,070,726 B2 | 12/2011 | Gonnelli et al. |
| 8,095,197 B2 | 1/2012 | Santini, Jr. et al. |
| 8,105,280 B2 | 1/2012 | Iddan et al. |
| 8,118,571 B2 | 2/2012 | Krisher |
| 8,118,782 B2 | 2/2012 | Remde |
| 8,128,589 B2 | 3/2012 | Freeman et al. |
| 8,147,451 B2 | 4/2012 | Brockman et al. |
| 8,152,764 B2 | 4/2012 | Istoc et al. |
| 8,182,447 B2 | 5/2012 | Moberg et al. |
| 8,206,350 B2 | 6/2012 | Mann et al. |
| 8,267,892 B2 | 9/2012 | Spencer et al. |
| 8,267,893 B2 | 9/2012 | Moberg et al. |
| 8,287,495 B2 | 10/2012 | Michaud et al. |
| 8,298,184 B2 | 10/2012 | DiPerna et al. |
| 8,310,415 B2 | 11/2012 | Mclaughlin et al. |
| 8,408,421 B2 | 4/2013 | DiPerna |
| 8,414,532 B2 | 4/2013 | Brandt et al. |
| 8,414,536 B2 | 4/2013 | Grant et al. |
| 8,444,595 B2 | 5/2013 | Brukalo et al. |
| 8,448,824 B2 | 5/2013 | DiPerna |
| 8,449,523 B2 | 5/2013 | Brukalo et al. |
| 8,573,027 B2 | 11/2013 | Rosinko et al. |
| 8,641,671 B2 | 2/2014 | Michaud et al. |
| 8,758,323 B2 | 6/2014 | Michaud et al. |
| 8,926,561 B2 | 1/2015 | Verhoef et al. |
| 2003/0055380 A1 | 3/2003 | Flaherty |
| 2003/0216683 A1 | 11/2003 | Shekalim |
| 2004/0078028 A1 | 4/2004 | Flaherty et al. |
| 2005/0137578 A1 | 6/2005 | Heruth et al. |
| 2005/0171512 A1 | 8/2005 | Flaherty |
| 2006/0206054 A1 | 9/2006 | Shekalim |
| 2006/0264835 A1 | 11/2006 | Nielsen et al. |
| 2007/0000337 A1 | 1/2007 | Gross |
| 2007/0088267 A1 | 4/2007 | Shekalim |
| 2007/0112301 A1 | 5/2007 | Preuthun et al. |
| 2007/0149926 A1 | 6/2007 | Moberg et al. |
| 2007/0167905 A1 | 7/2007 | Estes et al. |
| 2007/0264130 A1 | 11/2007 | Mallett |
| 2008/0029173 A1 | 2/2008 | DiPerna |
| 2008/0051765 A1 | 2/2008 | Mounce |
| 2008/0092969 A1 | 4/2008 | DiPerna |
| 2008/0097291 A1 | 4/2008 | Hanson et al. |
| 2008/0097309 A1 | 4/2008 | Enegren et al. |
| 2008/0097327 A1 | 4/2008 | Bente et al. |
| 2008/0196762 A1 | 8/2008 | Mallett et al. |
| 2008/0221523 A1 | 9/2008 | Moberg et al. |
| 2009/0062767 A1 | 3/2009 | Van Antwerp et al. |
| 2009/0069783 A1* | 3/2009 | Ellstrom et al. .............. 604/415 |
| 2009/0163855 A1 | 6/2009 | Shin et al. |
| 2009/0191067 A1 | 7/2009 | Diperna |
| 2009/0217982 A1 | 9/2009 | Diperna |
| 2009/0287180 A1 | 11/2009 | Diperna |
| 2010/0008795 A1 | 1/2010 | Diperna |
| 2010/0036327 A1 | 2/2010 | Diperna |
| 2010/0037680 A1 | 2/2010 | Moberg et al. |
| 2010/0096019 A1 | 4/2010 | Diperna |
| 2010/0114027 A1 | 5/2010 | Jacobson et al. |
| 2010/0152658 A1 | 6/2010 | Hanson et al. |
| 2010/0152674 A1 | 6/2010 | Kavazov et al. |
| 2010/0164727 A1 | 7/2010 | Bazargan et al. |
| 2010/0168670 A1 | 7/2010 | Srisathapat et al. |
| 2010/0168711 A1 | 7/2010 | Bazargan et al. |
| 2010/0174230 A1 | 7/2010 | Istoc et al. |
| 2010/0185142 A1 | 7/2010 | Kamen et al. |
| 2010/0185175 A1 | 7/2010 | Kamen et al. |
| 2010/0192686 A1 | 8/2010 | Kamen et al. |
| 2010/0217192 A1 | 8/2010 | Moberg et al. |
| 2010/0217193 A1 | 8/2010 | Moberg et al. |
| 2011/0004188 A1 | 1/2011 | Shekalim |
| 2011/0054390 A1 | 3/2011 | Searle et al. |
| 2011/0108158 A1 | 5/2011 | Huwiler et al. |
| 2011/0125095 A1 | 5/2011 | Lebel et al. |
| 2011/0133946 A1 | 6/2011 | Kopp et al. |
| 2011/0152770 A1 | 6/2011 | Diperna et al. |
| 2011/0152824 A1 | 6/2011 | Diperna et al. |
| 2011/0160678 A1 | 6/2011 | Chong et al. |
| 2011/0178461 A1 | 7/2011 | Chong et al. |
| 2011/0208123 A1 | 8/2011 | Gray et al. |
| 2011/0319862 A1 | 12/2011 | Friedman et al. |
| 2012/0017688 A1 | 1/2012 | Shekalim |
| 2012/0030610 A1 | 2/2012 | DiPerna et al. |
| 2013/0053816 A1 | 2/2013 | DiPerna et al. |
| 2013/0324928 A1 | 12/2013 | Kruse |
| 2014/0276538 A1 | 9/2014 | Michaud |

FOREIGN PATENT DOCUMENTS

| | | |
|---|---|---|
| WO | WO 99/64103 | 12/1999 |
| WO | WO 0040346 A1 | 7/2000 |
| WO | WO 2007/047279 A1 | 4/2007 |
| WO | WO 2007065944 A1 | 6/2007 |
| WO | WO 2009/143188 A2 | 11/2009 |
| WO | WO 2011/131777 A1 | 10/2011 |

OTHER PUBLICATIONS

Search Report and Written Opinion dated Mar. 4, 2013 for PCT Application No. PCT/US2012/048020 filed Jul. 24, 2012, 10 pages.
International Preliminary Report on Patentability dated Jan. 28, 2014 for PCT Application No. PCT/US2012/048020 filed Jul. 24, 2012, 7 pages.
Search Report and Written Opinion dated Aug. 22, 2013 for PCT Application No. PCT/US2013/040269 filed May 9, 2013, 17 pages.
International Preliminary Report on Patentability dated Oct. 29, 2014 for PCT Application No. PCT/US2013/040269 filed May 9, 2013, 9 pages.

* cited by examiner

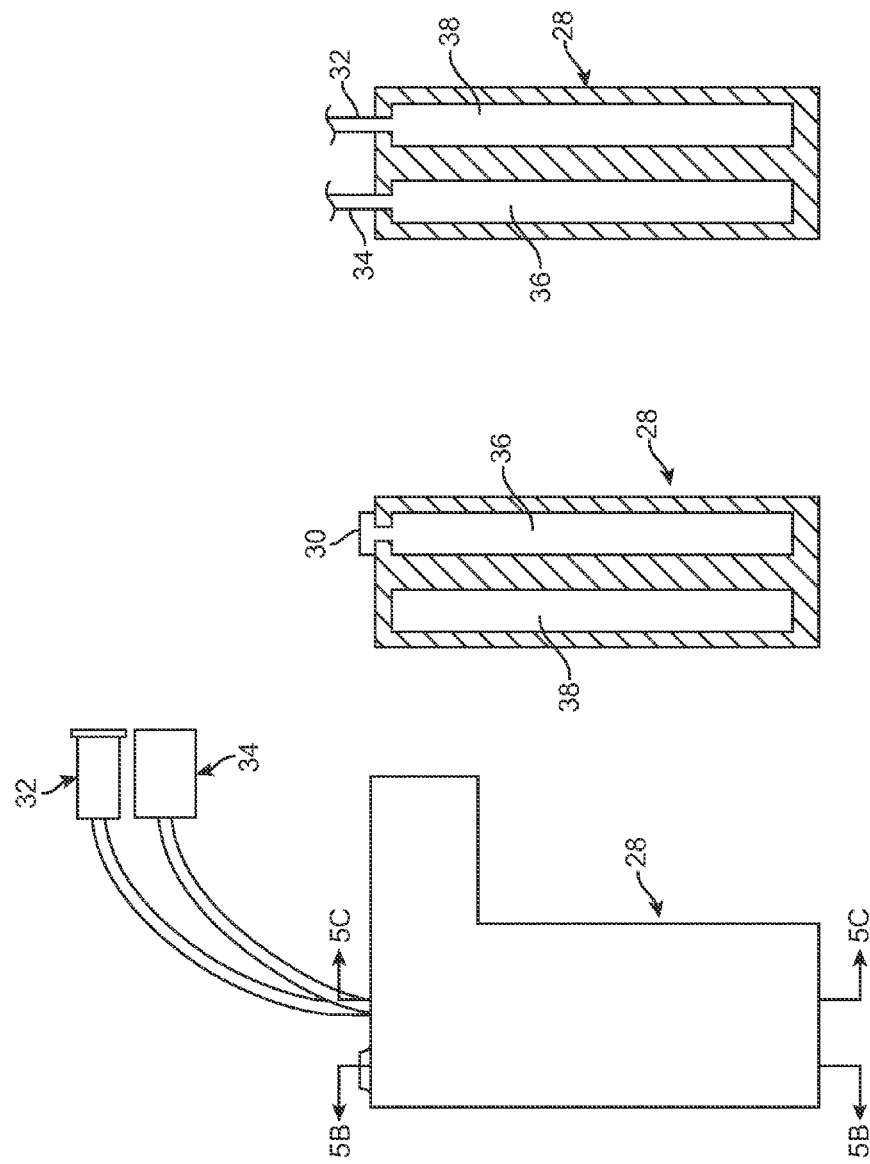

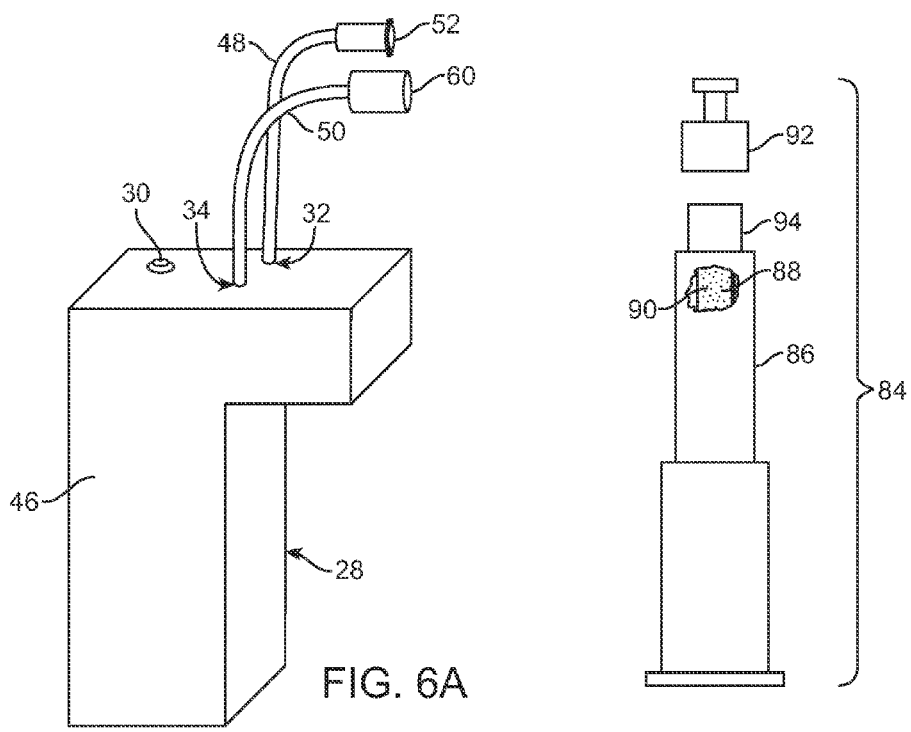
FIG. 6A
FIG. 6B
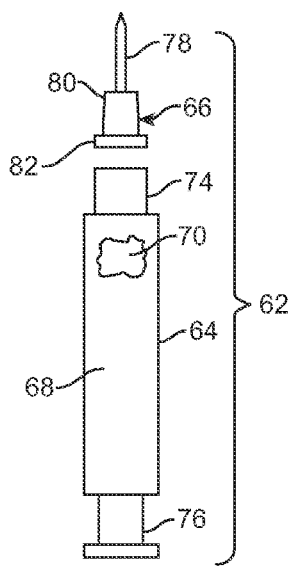
FIG. 6C
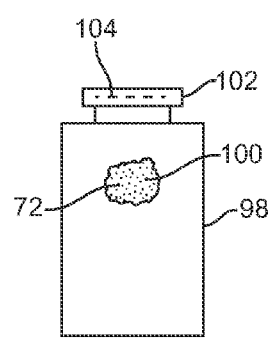
FIG. 6D

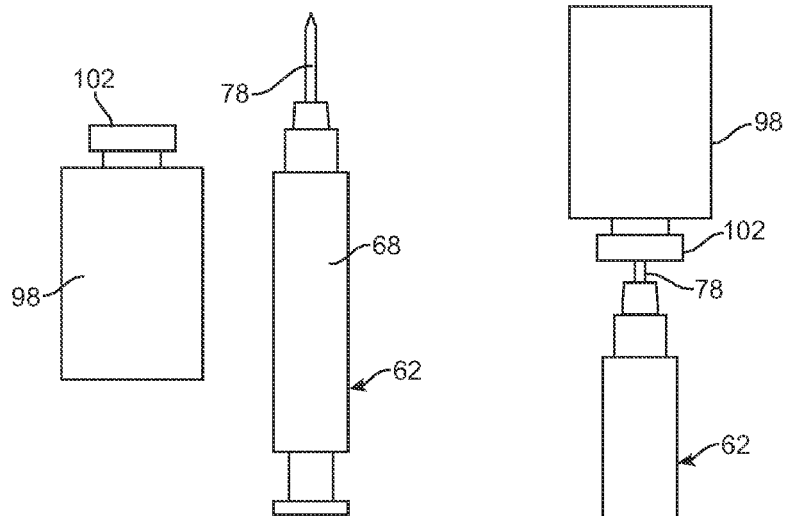
FIG. 6E
FIG. 6F
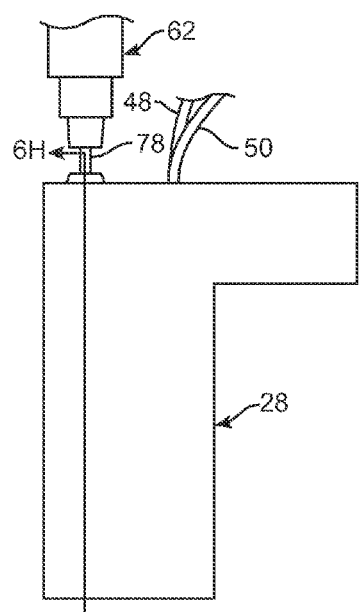
FIG. 6G
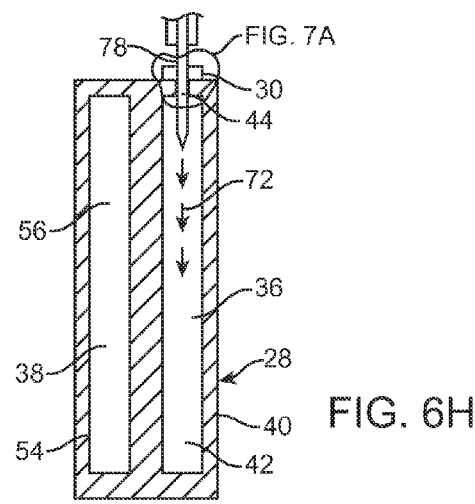
FIG. 6H

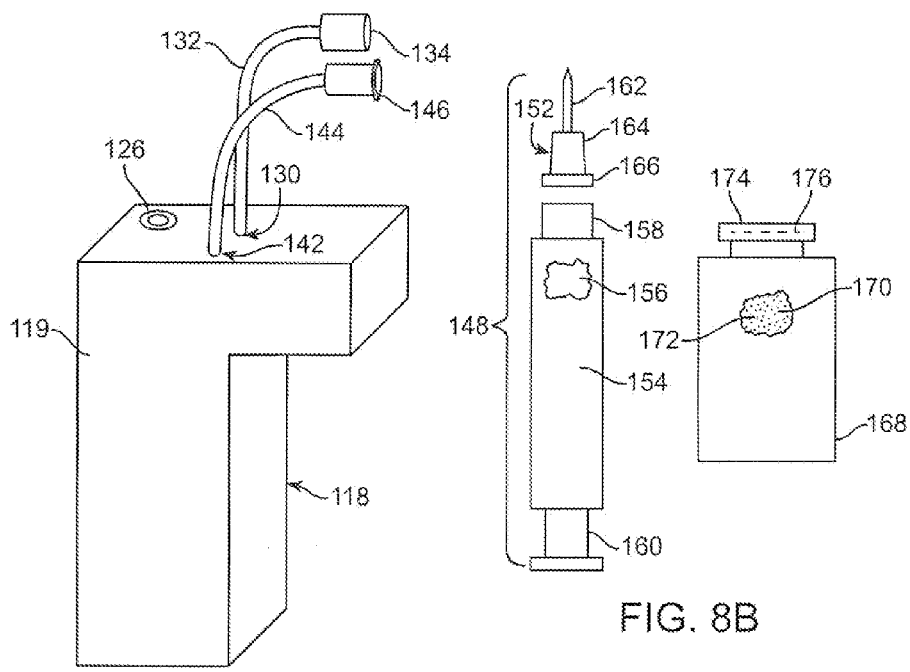
FIG. 8A
FIG. 8B
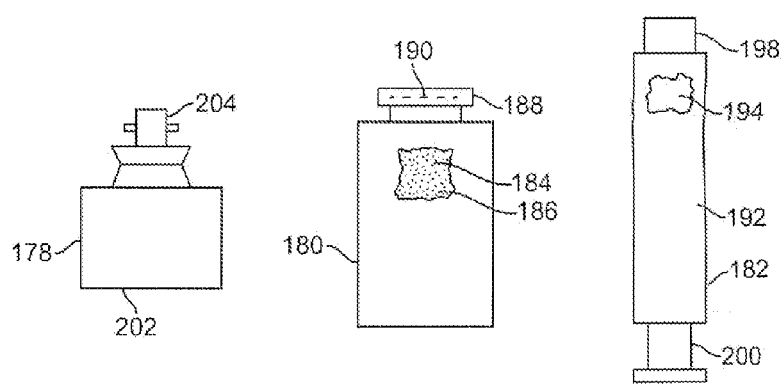
FIG. 8C

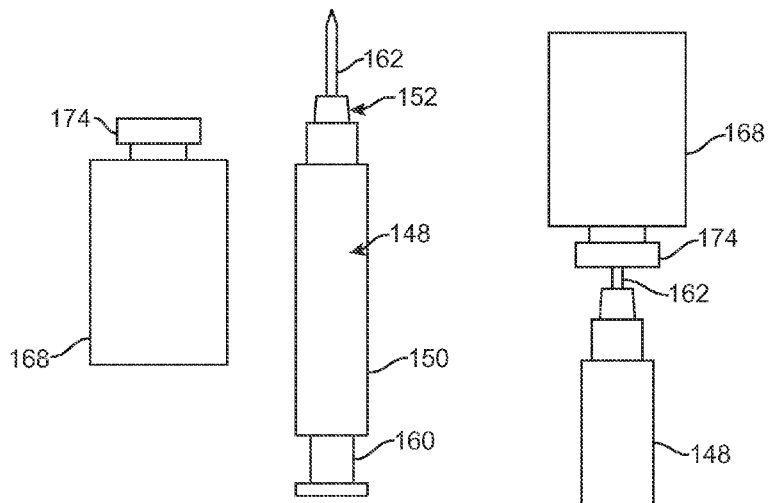
FIG. 8D
FIG. 8E
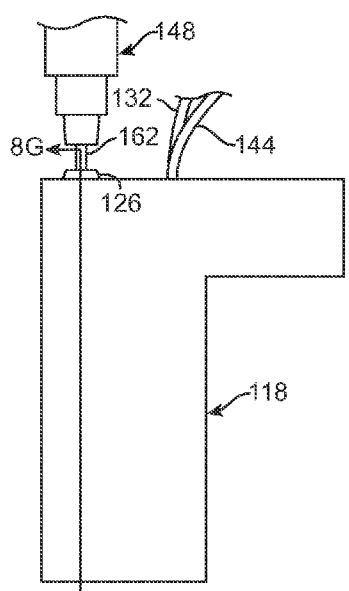
FIG. 8F
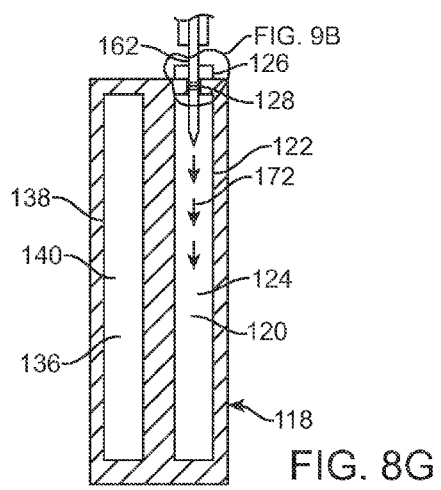
FIG. 8G

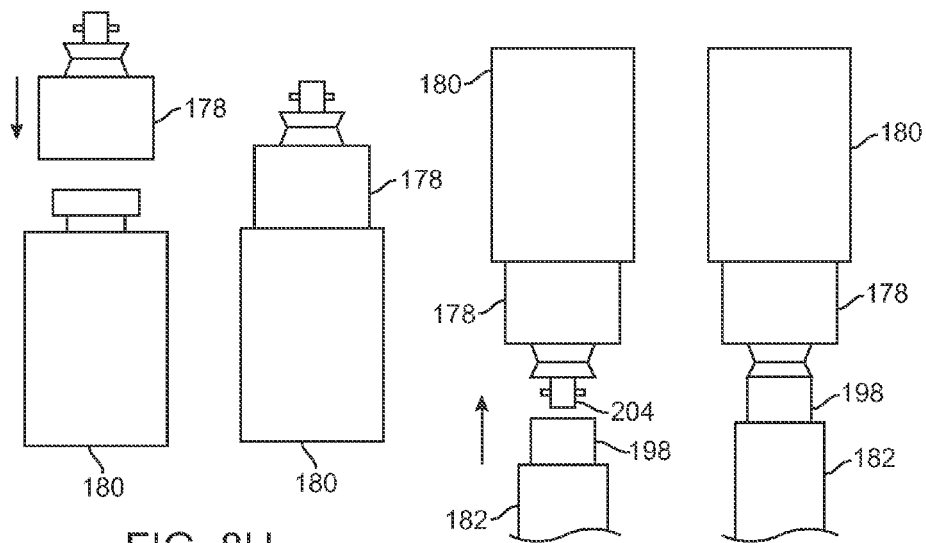
FIG. 8H
FIG. 8I
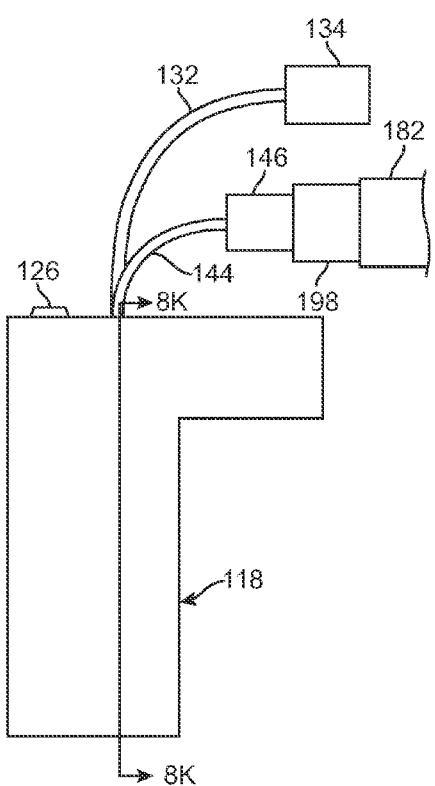
FIG. 8J
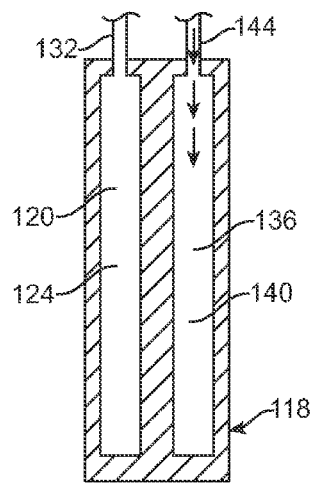
FIG. 8K

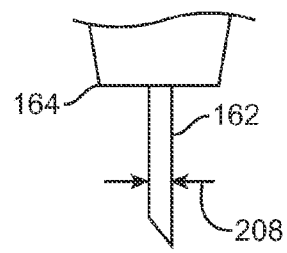
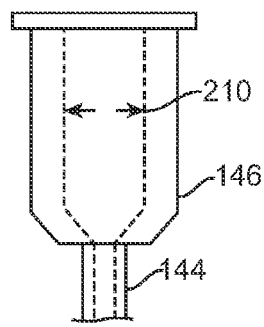
FIG. 9A
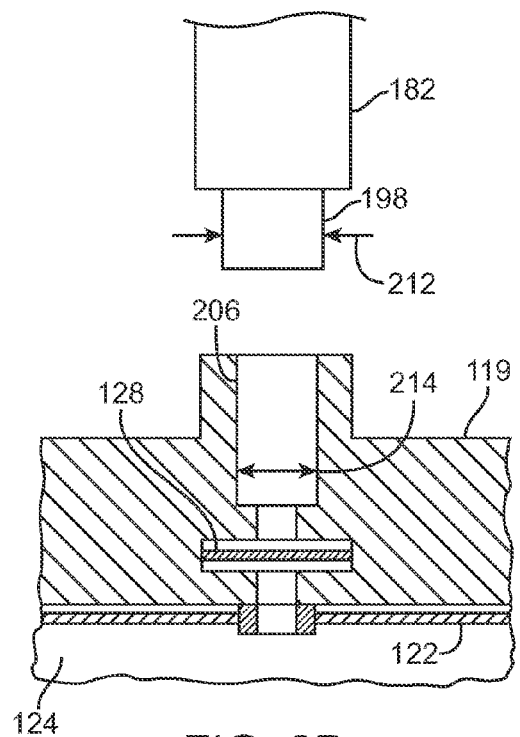
FIG. 9B

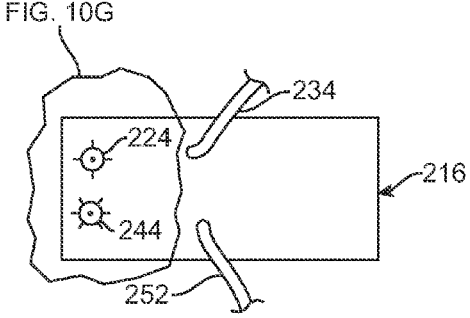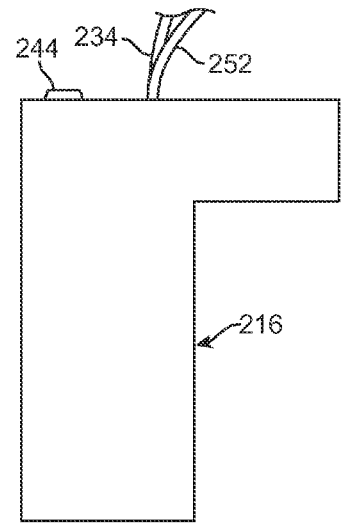
FIG. 10E  FIG. 10F
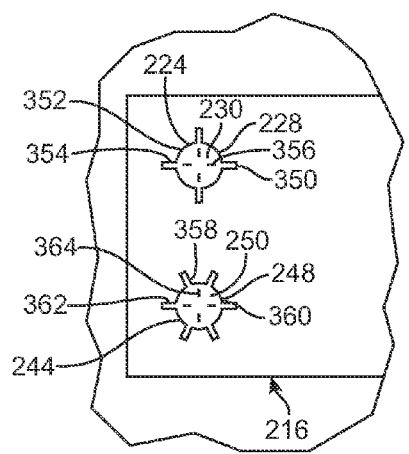
FIG. 10G

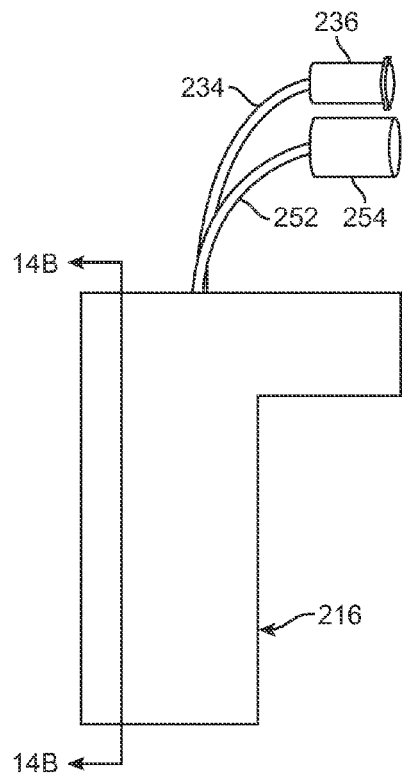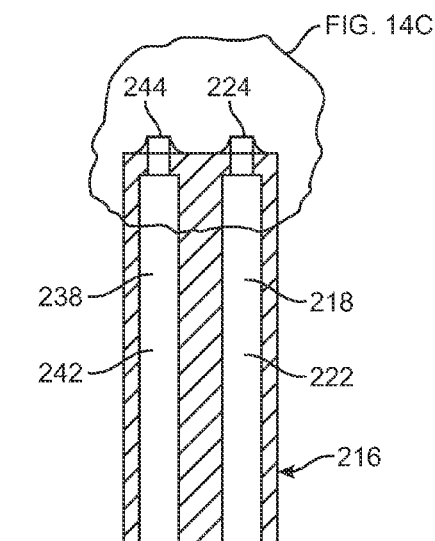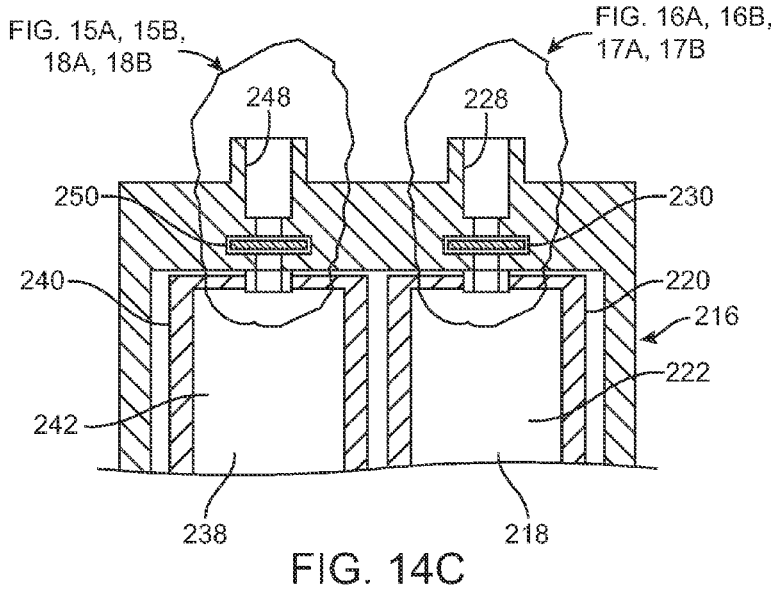

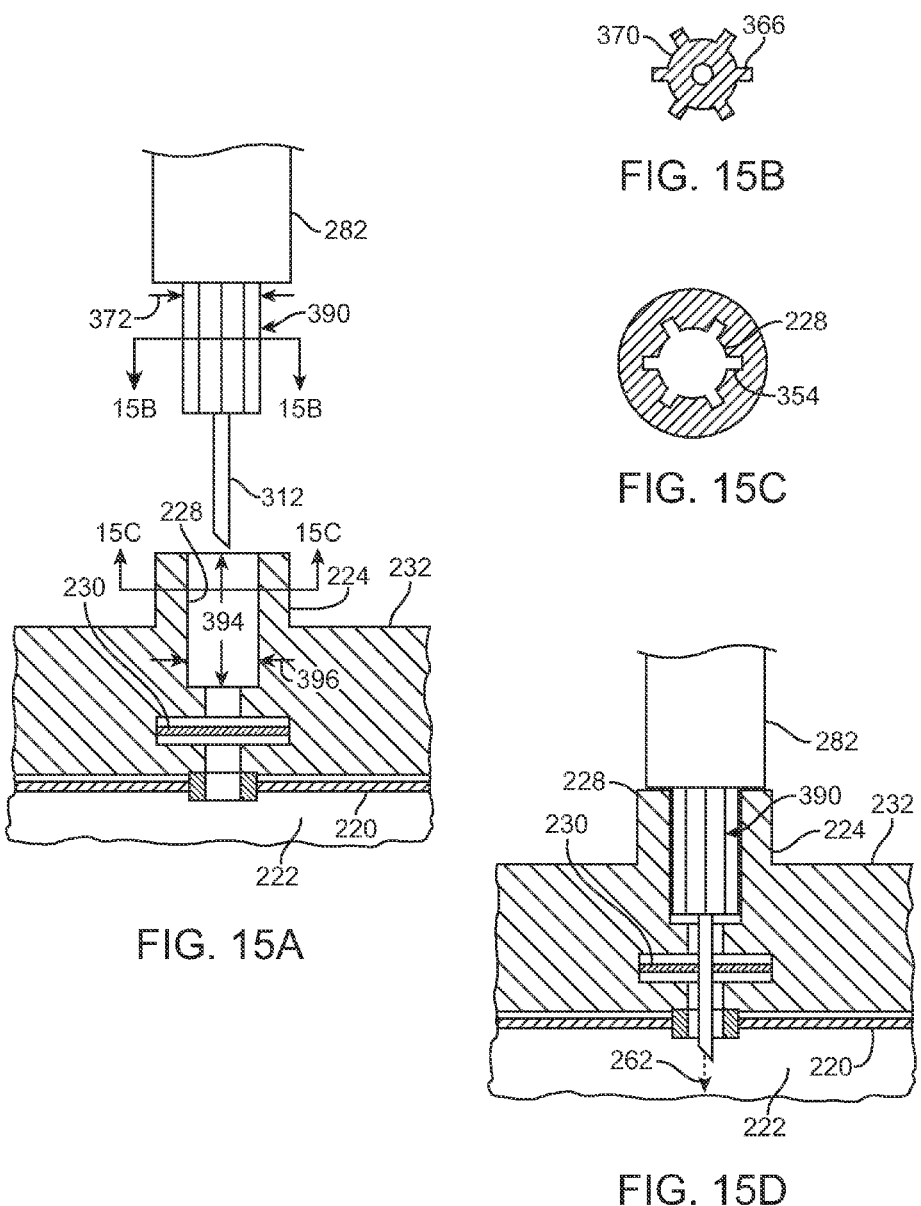

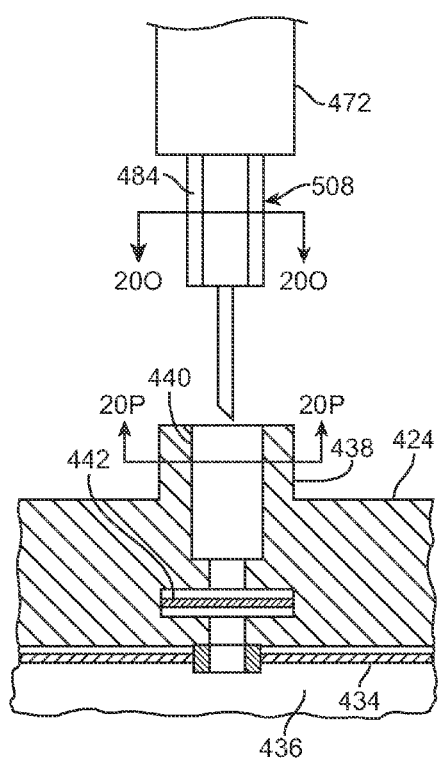
FIG. 20N
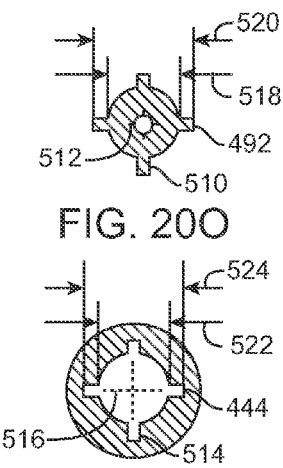
FIG. 20O
FIG. 20P
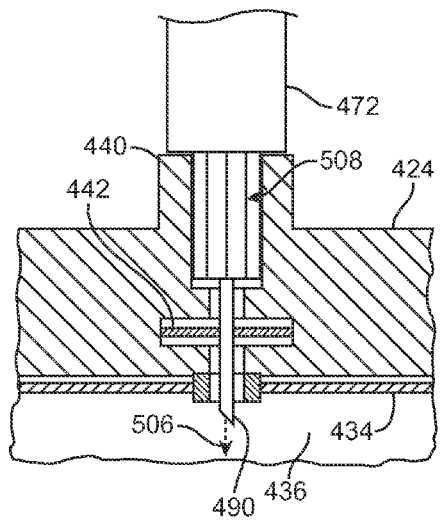
FIG. 20Q

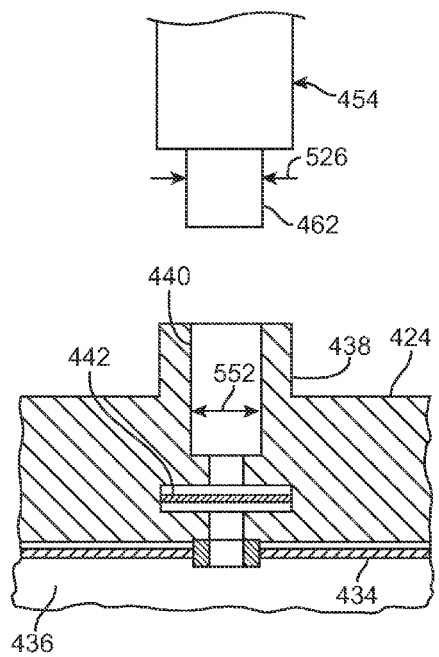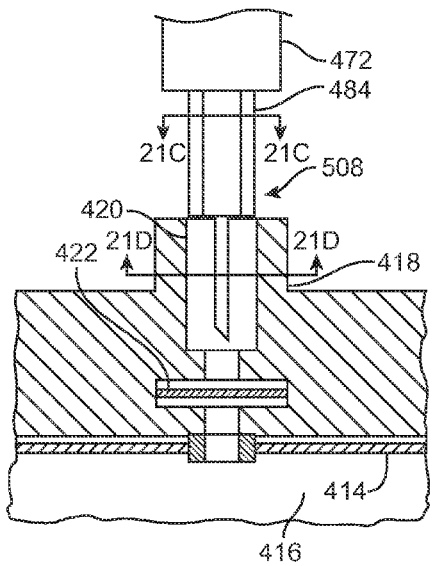
FIG. 21A  FIG. 21B
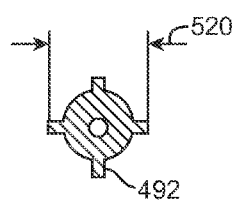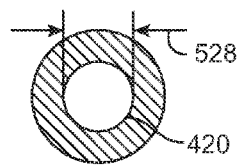
FIG. 21C  FIG. 21D

METHODS AND DEVICES FOR MULTIPLE FLUID TRANSFER

BACKGROUND

A refillable pump device which can accurately dispense multiple fluids has applications which span a wide variety of fields. For example, a refillable pump device could be used for the delivery of multiple pharmaceutical agents in the medical device industry, for the delivery of multiple part adhesives in the chemical industry, for the simultaneous delivery of colorants, seasonings, or preservatives during food products manufacturing, or the like. Although these applications do not represent the complete range of potential uses for a refillable pump device which can accurately dispense multiple fluids they are representative of applications for which, e.g., control of a volumetric flow rate of each individual fluid being delivered may be important.

In the context of drug or medicament delivery from multiple reservoirs, the possibility for human error exists as a user refills a multiple fluid pump device. In such a case, for example, a user incorrectly refilling the internal reservoirs of the pump device can result in an improper drug or medicament dosing for the user. In order to minimize the potential for these and other problems, what is needed are both (a) reliable refilling methods and (b) appropriate mechanical interfaces at each appropriate port of the reservoirs of a pump device or cartridge thereof as well as at each appropriate port of the external reservoir.

SUMMARY

Some embodiments of a fluid transfer system may include a first receptacle reservoir having a first receptacle reservoir body, a first receptacle interior volume disposed within the first receptacle reservoir body, and a first receptacle reservoir interface in fluid communication with the first receptacle interior volume. The fluid transfer system may also include a second receptacle reservoir having a second receptacle reservoir body, a second receptacle interior volume disposed within the second receptacle reservoir body, and a second receptacle reservoir interface in fluid communication with the second receptacle interior volume. A first supply reservoir of the fluid transfer system may include a first supply reservoir body, a first supply interior volume disposed within the first supply reservoir body, a first fluid disposed within the first supply interior volume, and a first supply reservoir interface in fluid communication with the first supply interior volume. The first supply reservoir interface may be capable of coupling with the first receptacle reservoir interface in order to create a first fluid communication junction between the first supply interior volume and the first receptacle interior volume. The first supply reservoir interface may also be configured such that it is mechanically incompatible with the second receptacle reservoir interface so as to prevent the creation of a fluid communication junction between the two interfaces. A second supply reservoir of the fluid transfer system may include a second supply reservoir body, a second supply interior volume disposed within the second supply reservoir, a second fluid disposed within the second supply interior volume, and a second supply reservoir interface in fluid communication with the second supply interior volume. The second supply reservoir interface may be capable of coupling with the second receptacle reservoir interface in order to create a second fluid communication junction between the second supply interior volume and the second reservoir interior volume. The second supply reservoir interface may also be configured such that it is mechanically incompatible with the first receptacle reservoir interface so as to prevent the creation of a fluid communication junction between the two interfaces.

Some embodiments of a method for transferring fluids may include creating a first fluid communication junction between a first receptacle reservoir and a first supply reservoir by coupling a first receptacle reservoir interface to a first supply reservoir interface. A first fluid can then be transferred from the first supply reservoir to the first receptacle reservoir. The first supply reservoir interface may be configured such that it is mechanically incompatible with a second receptacle reservoir interface so as to prevent a fluid communication junction between the two interfaces. The method embodiment may also include creating a second fluid communication junction between a second receptacle reservoir and a second supply reservoir by coupling the second receptacle reservoir interface to a second supply reservoir interface. A second fluid can then be transferred from the second supply reservoir to the second receptacle reservoir. The second supply reservoir interface may be configured such that it is mechanically incompatible with the first receptacle reservoir interface so as to prevent the creation of a fluid communication junction between the two interfaces.

Some embodiments of a fluid transfer system may include a first pump reservoir having a first pump reservoir body, a first reservoir interior volume disposed within the first pump reservoir body, an input port, and a first output port. The input port may include a first reservoir septum disposed within the first pump reservoir body in some cases. The first output port is in fluid communication with the first reservoir interior volume. The fluid transfer system may also include a second pump reservoir having a second pump reservoir body, a second reservoir interior volume disposed within the second pump reservoir body, and a second output port. The second output port has a second output port adapter which may be in fluid communication with the second reservoir interior volume. The fluid transfer system may also include a syringe hub assembly having a syringe body, a syringe interior volume disposed within the syringe body, a first fluid contained within the syringe interior volume, and a hub assembly coupled to the syringe body. The hub assembly may include a needle which is capable of penetrating the first reservoir septum, but which is mechanically incompatible with the second output port adapter. The fluid transfer system may also include a diabetic pen reservoir assembly having a diabetic pen reservoir body, a pen interior volume disposed within the diabetic pen reservoir body, a second fluid contained within the pen interior volume, and a diabetic pen reservoir adapter. The diabetic pen reservoir adapter may be coupled to the diabetic pen reservoir body and configured to be mechanically compatible with the second output port adapter and mechanically incompatible with the input port.

Some embodiments of a method for transferring fluids may include creating a first fluid communication junction between a first pump reservoir and a syringe reservoir by piercing a first reservoir septum of a first input port of the first pump reservoir with a needle of a syringe hub assembly. The method includes transferring a first fluid from the syringe reservoir to the first pump reservoir. The needle may be configured such that it is mechanically incompatible with a second adapter of a second output port of a second pump reservoir so as to prevent the creation of a fluid communication junction between the syringe reservoir and the second output port. The method for transferring fluids may also include creating a second fluid communication junction between the second pump reservoir and a diabetic pen reservoir by coupling the second adapter of the second output port to a diabetic pen reservoir adapter. A second fluid can then be transferred from the diabetic pen reservoir to the second pump reservoir. The diabetic pen reservoir adapter may be configured such that it is mechanically incompatible with the first input port so as to prevent the creation of a fluid communication junction between the pen reservoir adapter and the first input port.

Some embodiments of a fluid transfer system may include a first pump reservoir having a first pump reservoir body and a first reservoir interior volume disposed within the first pump reservoir body. The first pump reservoir may include an input port which has a first reservoir septum that seals the first reservoir interior volume. The first pump reservoir may also include a first output port which is in fluid communication with the first reservoir interior volume. The fluid transfer system may also include a second pump reservoir having a second pump reservoir body and a second reservoir interior volume disposed within the second pump reservoir body. The second pump reservoir may also include a second output port which may be in fluid communication with the second reservoir interior volume. The fluid transfer system may also include a syringe hub assembly having a first syringe body and a first syringe interior volume disposed within the syringe body. A first fluid may be contained within the first syringe interior volume. A hub assembly may be coupled to the first syringe body. The hub assembly may include a needle which is capable of piercing the first reservoir septum in order to create a first fluid communication junction between the first syringe interior volume and the first pump interior volume. The needle may also be configured such that it is mechanically incompatible with the second output port adapter so as to prevent a fluid communication junction between the two components. The fluid transfer system may also include a second syringe reservoir which has a second syringe body, a second syringe interior volume which contains a second fluid and is disposed within the syringe body, and a second syringe port in fluid communication with the second syringe interior volume. The second syringe port may be configured such that it is capable of coupling to the second output port adapter so as to form a fluid communication junction. The second syringe port may also be configured such that it is mechanically incompatible with the input port so as to prevent a fluid communication junction between the two components.

Some embodiments of a method for transferring fluids may include creating a first fluid communication junction between a first pump reservoir and a first syringe reservoir by piercing a first reservoir septum of a first input port of the first pump reservoir with a needle of a syringe hub assembly. The method includes transferring a first fluid from the first syringe reservoir to the first pump reservoir. The needle may be configured such that it is mechanically incompatible with a second adapter of a second output port of a second pump reservoir so as to prevent the creation of a fluid communication junction between the first syringe reservoir and the second output port. The method for transferring multiple fluids may also include creating a second fluid communication junction between the second pump reservoir and a second syringe reservoir by coupling the second adapter of the second output port to a second syringe port. A second fluid can then be transferred from the second syringe reservoir to the second pump reservoir. The second syringe port may be configured such that it is mechanically incompatible with the first input port so as to prevent the creation of a fluid communication junction between the second syringe reservoir and the first input port.

Some embodiments of a vial adapter assembly may include a hub assembly having a hub body with a proximal section that is configured to mate with a syringe port and a needle sealingly secured to a distal section of the hub body. The vial adapter assembly may also include a vial adapter which may have a vial adapter body of resilient material and a distal cavity of sufficient inner dimensions to engage a vial reservoir. The distal cavity may also include at least one hooked clip which is disposed toward the distal cavity. The hooked clip may be configured such that after the vial reservoir is engaged by the hooked clip the needle is disposed in an interior volume and in fluid communication with an interior volume of the vial reservoir. The vial adapter assembly may also include an engagement feature which releasably secures the hub body to the vial adapter body such that the needle is disposed within and is in axial alignment of the distal cavity.

Some embodiments of a method for transferring fluids may include coupling a vial adapter assembly to a vial reservoir by inserting a spigot port located on the vial reservoir into a distal cavity of the vial adapter assembly such that a needle contained within the distal cavity punctures a vial septum disposed within the spigot port which creates a fluid communication junction between the vial reservoir and an interior channel of a hub assembly. The vial adapter assembly may be coupled to the vial reservoir by at least one hooked clip which engages the spigot port. The method for transferring fluids may further include attaching a syringe reservoir to the hub assembly and transferring a fluid from the vial reservoir to the syringe reservoir. The fluid transfer method may further include disengaging an engagement feature which releasably secures the hub assembly to the vial adapter assembly with the syringe reservoir remaining coupled to the hub assembly and the vial reservoir remaining secured to the vial adapter assembly.

Some embodiments of a fluid transfer system may include a first vial adapter assembly which may have a first hub assembly and a first vial adapter. The first hub assembly may include a first hub body having a proximal section capable of mating with a syringe port, and a distal section which is sealingly secured to a first needle. The first hub assembly may also include a first key feature that is mechanically compatible with a first keyed port of a first receptacle reservoir, but is mechanically incompatible with a second keyed port of a second receptacle reservoir. The first vial adapter may include a first vial adapter body having a first distal cavity which has an inner transverse dimension configured to couple to a first spigot of a first vial reservoir but not couple to a second spigot port of a second vial reservoir. The first distal cavity may also include at least one first hooked clip capable of engaging with the first spigot port but not the second spigot port. A first engagement feature may releasably secure the first hub body to the first vial adapter body such that the first needle is disposed within and is in axial alignment of the first distal cavity. The fluid transfer system may also include a second vial adapter assembly which may have a second hub assembly and a second vial adapter. The second hub assembly may include a second hub body which has a proximal section capable of mating with a syringe port, and a distal section which is sealingly secured to a second needle. The second hub assembly may also include a second key feature that is mechanically compatible with the second keyed port of the second receptacle reservoir, but is mechanically incompatible with the first keyed port of the first receptacle reservoir. The second vial adapter may include a second vial adapter body having a second distal cavity which has an inner transverse dimension configured to couple to the second spigot of the second vial reservoir but not couple to the first spigot port of the first vial reservoir. The second distal cavity may also include at least one second hooked clip capable of engaging with the second spigot port but not the first spigot port. A second engagement feature may releasably secure the second hub body to the second vial adapter body such that the second needle is disposed within and is in axial alignment of the second distal cavity.

Some embodiments of a method for transferring fluids may include providing a first vial adapter assembly. The first vial adapter assembly may include a first hub having a first needle extending from it and a first key feature which is mechanically compatible with a first keyed port of a first pump reservoir and which is mechanically incompatible with a second keyed port of a second pump reservoir. The first vial adapter assembly may also include a first vial adapter which has a first distal cavity which is configured to couple to a first spigot of a first vial reservoir but mechanically incompatible with a second spigot port of a second vial reservoir. The first vial adapter assembly may also include a first engagement feature which releasably secures the hub to the first vial adapter with the first needle disposed within the first distal cavity. The method for transferring fluids may also include providing a first vial reservoir which has a first vial internal volume that contains a first fluid. The first vial reservoir may also include a first spigot port which is in fluid communication with the first vial internal volume, and a first vial septum which is disposed within and seals the first spigot port. The fluid transfer method may further include providing a second vial adapter assembly. The second vial adapter assembly may include a second hub having a second needle extending from it and a second key feature which is mechanically compatible with the second keyed port of the first pump reservoir and which is mechanically incompatible with the first keyed port of the second pump reservoir. The second vial adapter assembly may also include a second vial adapter which may have a second distal cavity that is configured to couple to the second spigot of the second vial reservoir but mechanically incompatible with the first spigot port of the first vial reservoir. The second vial adapter assembly may also include a second engagement feature which releasably secures the second hub to the second vial adapter with the second needle disposed within the second distal cavity. The fluid transfer method may also include providing a second vial reservoir which may have a second vial internal volume that contains a second fluid. The second vial reservoir may also have a second spigot port which is in fluid communication with the second vial internal volume, and a second vial septum that is disposed within and seals the second spigot port. The fluid transfer method may further include coupling the first vial adapter assembly to the first vial reservoir by inserting the first spigot port into the first distal cavity so that the first tubular needle punctures the first vial septum and the first vial adapter assembly is mechanically captured to the first vial reservoir. The fluid transfer method may also include coupling the first syringe to the first hub and transferring the first fluid from the first vial reservoir to a first syringe reservoir of the first syringe through a lumen of the first tubular needle. The fluid transfer method may also include detaching the first hub from the first vial adapter by disengaging the first engagement feature. The fluid transfer method may also include coupling the second vial adapter assembly to the second vial reservoir by inserting the second spigot port into the second distal cavity so that the second tubular needle punctures the second vial septum and the second vial adapter assembly is mechanically captured to the second vial reservoir. The fluid transfer method may also include coupling a second syringe reservoir to the second hub and then transferring the second fluid from the second vial reservoir to a second syringe reservoir of the second syringe through a lumen of the second needle. The fluid transfer method may also include detaching the second hub from the second vial adapter by disengaging the second engagement feature.

Some embodiments of fluid transfer system may include a first hub assembly and a first keyed port. The first hub assembly may include a first hub body that has a proximal section that is configured to mate with a syringe port. The first hub assembly may also include a first hub key feature which is disposed on a perimeter of the first hub body, and which is configured to couple to a first keyed port of a first receptacle reservoir but which is mechanically incompatible with a second keyed port of a second receptacle reservoir. A first needle including an elongated tubular member of high strength material may be sealingly secured to a distal section of the first hub body. The first keyed port may include a first channel which is in fluid communication with an interior volume of a first receptacle reservoir. The first channel may be configured such that it can accommodate the insertion of the first hub body. A first septum is disposed within and seals the first channel, and is positioned at a depth within the first channel that is substantially equal to or greater than a distance that the first needle extends from the first hub. The first keyed port may also include a first port key feature which is disposed on an inner perimeter of the first channel, and which is configured to couple with the first hub key feature but which is mechanically incompatible with a second hub key feature. Other embodiments of the fluid transfer system may include a second hub assembly and a second keyed port. The second hub assembly may include a second hub body which has a proximal section that is configured to couple with a syringe port. The second hub assembly may also include a second hub key feature which is disposed on a perimeter of the second hub body, and which is configured to couple to the second keyed port of the first receptacle reservoir but which is mechanically incompatible with the first keyed port of the first receptacle reservoir. A second needle including an elongate tubular member of high strength material may be sealingly secured to a distal section of the second hub body. The second keyed port may include a second channel which is in fluid communication with an interior volume of a second receptacle reservoir. The second channel may be configured such that it can accommodate the insertion of the second hub body. A second septum is disposed within and seals the second channel, and is positioned at a depth within the second channel that is substantially equal to or greater than a distance that the second needle extends from the second hub. The second keyed port may also include a second port key feature which is disposed on an inner perimeter of the second channel, and which is configured to couple with the second hub key feature but which is mechanically incompatible with the first hub key feature.

Some embodiments of a method for transferring fluids may include creating a first fluid communication junction between a first receptacle reservoir and a first supply reservoir by coupling a first receptacle keyed interface to a mechanically compatible first supply keyed interface. A first fluid may then be transferred from the first supply reservoir into the first receptacle reservoir through the first fluid communication junction. The first supply keyed interface is configured to be mechanically incompatible with a second receptacle keyed interface so as to prevent a fluid communication junction between the two interfaces. Other embodiments of the method may include creating a second fluid communication junction between a second receptacle reservoir and a second supply reservoir by coupling the second receptacle keyed interface to a mechanically compatible second supply keyed interface. A second fluid can then be transferred from the second supply reservoir into the second receptacle reservoir through the second fluid communication junction. The second supply keyed interface is configured to be mechanically incompatible with the first receptacle keyed interface so as to prevent a fluid communication junction between the two interfaces.

Some embodiments of a fluid transfer system may include a first vial adapter assembly, a first vial reservoir, a first receptacle reservoir, a second vial adapter assembly, a second vial reservoir, and a second receptacle reservoir. The first vial adapter assembly may include a first hub assembly, a first vial adapter, and a first engagement feature. The first vial adapter assembly may include a first hub having a first hub body. The first hub body may include a proximal section which is capable of mating with a syringe port and a distal section which is sealingly secured to a first needle. The first hub assembly may also include a first hub key feature which is disposed on a perimeter of the first hub body and which is mechanically compatible with a first keyed port of a first receptacle reservoir, but which is mechanically incompatible with a second keyed port of a second receptacle reservoir. The first vial adapter assembly may also include a first vial adapter which has a first vial adapter body. The first vial adapter body may incorporate a first distal cavity which has an inner transverse dimension configured to couple to a first spigot port of a first vial reservoir, but not couple to a second spigot port of a second vial reservoir. The first distal cavity may also include a first hooked clip configured to engage a first spigot port but not a second spigot port. The first vial adapter assembly may also include a first engagement feature which releasably secures the first hub body to the first vial adapter body such that the first needle of the first hub assembly is disposed within and is in axial alignment with the first distal cavity of the first vial adapter. The first vial reservoir has a first vial reservoir body which may include a first vial internal volume disposed within it. The first vial reservoir may also include a first spigot port in fluid communication with the first vial internal volume, a first vial septum disposed within the first spigot port, and a first fluid disposed within the first vial internal volume. The first receptacle reservoir may include an interior volume and a first keyed port. The first keyed port may have a first channel which is in fluid communication with the interior volume of the first receptacle reservoir, and a first septum which is disposed within and seals the first channel at a depth which is greater than or equal to a distance which the first needle extends from the first hub body. The first keyed port may also have a first port keyed feature which is disposed on a perimeter of the first channel and which is mechanically compatible with the first hub key feature. The second vial adapter assembly may include a second hub assembly, a second vial adapter, and a second engagement feature. The second vial adapter assembly may include a second hub having a second hub body. The second hub body may include a proximal section which is capable of mating with a syringe port and a distal section which is sealingly secured to a second needle. The second hub assembly may also include a second hub key feature which is disposed on a perimeter of the second hub body and which is mechanically compatible with the second keyed port of the second receptacle reservoir, but which is mechanically incompatible with the first keyed port of the first receptacle reservoir. The second vial adapter assembly may also include a second vial adapter which has a second vial adapter body. The second vial adapter body may incorporate a second distal cavity which has an inner transverse dimension configured to couple to the second spigot port of the second vial reservoir, but not to couple to the first spigot port of the first vial reservoir. The second distal cavity may also include a second hooked clip configured to engage the second spigot port but not the first spigot port. The second vial adapter assembly may also include a second engagement feature which releasably secures the second hub body to the second vial adapter body such that the second needle of the second hub assembly is disposed within and is in axial alignment with the second distal cavity of the second vial adapter. The second vial reservoir has a second vial reservoir body which may include a second vial internal volume disposed within it. The second vial reservoir may also include the second spigot port which is in fluid communication with the second vial internal volume, a second vial septum disposed within the second spigot port, and a second fluid disposed within the second vial internal volume. The second receptacle reservoir may include an interior volume and a second keyed port. The second keyed port may have a second channel which is in fluid communication with the interior volume of the second receptacle reservoir, and a second septum which is disposed within and seals the second channel at a depth which is greater than or equal to a distance which the second needle extends from the second hub body. The second keyed port may also have a second port keyed feature which is disposed on a perimeter of the second channel and which is mechanically compatible with the second hub key feature.

Some embodiments of a fluid transfer system may include a first pump reservoir, a second pump reservoir, a diabetic pen reservoir assembly, and a syringe hub assembly. The first pump reservoir may include a first reservoir body having a first reservoir interior volume which is disposed within the first reservoir body and which is capable of containing fluid. The first pump reservoir may also include a first input port which has a first channel that is in fluid communication with the first reservoir interior volume. The first input port may also include a first septum that is disposed within and seals the first channel. A tubular bayonet needle may be configured to be inserted through the first septum such that an inner lumen of the bayonet needle is in fluid communication with the first reservoir interior volume. The first pump reservoir may also include a first output port which has a first fluid line that is in fluid communication with the first reservoir interior volume, and a first output port adapter which is secured to and in fluid communication with the first fluid line. The second pump reservoir may include a second pump reservoir body having a second reservoir interior volume which is disposed within the second reservoir body and which is capable of containing fluid. The second pump reservoir may also include a second input port which has a second channel which is in fluid communication with the second reservoir interior volume. A second septum is disposed within and seals the second channel, and a second key feature is disposed on a perimeter of the second channel. The second pump reservoir may also include a second output port comprising a second fluid line which is in fluid communication with the second reservoir interior volume, and a second output port adapter which is secured to and in fluid communication with the second fluid line. The diabetic pen reservoir assembly may include a diabetic pen reservoir body which has a pen interior volume disposed within it. A first fluid may be contained within the pen interior volume. The diabetic pen reservoir assembly may also include a pen port which is in fluid communication with the pen interior volume. The pen port may be configured to couple to the bayonet needle in order to create a second fluid communication junction between the pen interior volume and the first interior volume. The pen port is mechanically incompatible with the first channel of the first input port so as to prevent a fluid communication junction between the two components. The syringe hub assembly may include a syringe and a hub assembly. The syringe may include a syringe which has a syringe body, a syringe interior volume disposed within the syringe body, a second fluid contained within the syringe interior volume, and a syringe port. The hub assembly may include a hub body having a proximal section secured to the syringe port, and a distal section of the hub body which is sealingly secured to a needle. The hub assembly may also include a hub key feature which is disposed on a perimeter of the hub body, and which is mechanically compatible with the second input port so as to allow for the coupling of the hub assembly to the second input port and which is mechanically incompatible with the first input port. The needle is configured to pierce the second reservoir septum in order to create a second fluid communication junction between the syringe interior volume and the second interior volume, but is configured to be mechanically incompatible with the second output port adapter so as to prevent the creation of a fluid communication junction between the two components.

Some embodiments of a method for transferring fluids may include creating a first fluid communication junction between a first pump reservoir and a diabetic pen reservoir by coupling a diabetic pen port of the diabetic pen reservoir to a bayonet needle adapter. The bayonet needle adapter is secured to the first pump reservoir by a bayonet needle which may be configured to be disposed through a first reservoir septum of a first port of the first pump reservoir. A first fluid may then be transferred from the diabetic pen reservoir to the first pump reservoir through the first fluid communication junction. The diabetic pen port is configured to be mechanically incompatible with a second keyed input port so as to prevent the creation of a fluid communication junction between the two components. The method for transferring fluids may further include inserting a keyed hub assembly coupled to a syringe reservoir into the second keyed input port of a second pump reservoir such that a needle of the keyed hub assembly penetrates a second reservoir septum thereby creating a second fluid communication junction between the second pump reservoir and the syringe reservoir. The keyed hub assembly is mechanically incompatible with the first input port so as to prevent the creation of a fluid communication junction between the two components.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

FIG. 3A is a view in transverse section of the dual reservoir cartridge embodiment of FIG. 3 showing a first input port in fluid communication with a first pump reservoir and a second input port in fluid communication with a second pump reservoir.

FIG. 3B is a view in transverse section of the dual reservoir cartridge embodiment of FIG. 3 showing a first output port in fluid communication with the first pump reservoir and a second output port in fluid communication with the second pump reservoir.

FIG. 5A shows the dual reservoir cartridge embodiment of FIG. 4.

FIG. 5B is a view in transverse section of the dual reservoir cartridge embodiment of FIG. 5A showing a first input port in fluid communication with a first pump reservoir.

FIG. 5C is a view in transverse section of the dual reservoir cartridge embodiment of FIG. 5A showing a first output port in fluid communication with the first pump reservoir and a second output port in fluid communication with a second pump reservoir.

FIG. 6A is a perspective view of the dual reservoir cartridge embodiment.

FIG. 6B shows a diabetic pen reservoir embodiment and a female luer adapter embodiment capable of mating with a port of the diabetic pen adapter.

FIG. 6C shows a syringe reservoir embodiment and a hub assembly embodiment capable of mating with a syringe port of the syringe reservoir.

FIG. 6D shows a vial reservoir embodiment with a spigot port.

FIG. 6E shows the vial reservoir embodiment of FIG. 6D and a syringe hub assembly embodiment.

FIG. 6F shows a needle of the syringe hub assembly embodiment of FIG. 6E inserted into the spigot port of the vial reservoir embodiment of FIG. 6D and a plunger of the syringe reservoir embodiment being activated.

FIG. 6G shows the needle of the syringe hub assembly embodiment of FIG. 6F inserted into an input port of the dual reservoir cartridge embodiment of FIG. 6A.

FIG. 6H is a view in transverse section of the dual reservoir cartridge embodiment of FIG. 6G showing a first fluid being transferred from the syringe reservoir embodiment to a first pump reservoir of the dual reservoir cartridge of FIG. 6A.

FIG. 8A is a perspective view of a dual reservoir cartridge embodiment with a single input port and multiple output ports.

FIG. 8B shows embodiments of a first syringe reservoir, a hub assembly, and a first vial reservoir.

FIG. 8C shows embodiments of a vial adapter, a second vial reservoir, and a second syringe reservoir.

FIG. 8D depicts the first vial reservoir embodiment of FIG. 8B and embodiments of the first syringe reservoir and hub assembly of FIG. 8B in a coupled state.

FIG. 8E shows a needle of the first syringe hub assembly embodiment of FIG. 8B inserted into a first spigot port of the vial reservoir embodiment of FIG. 8B and a plunger of the first syringe hub assembly being activated.

FIG. 8F shows the needle of the first syringe hub assembly embodiment of FIG. 8D inserted into an input port of the dual reservoir cartridge embodiment of FIG. 8A.

FIG. 8G is a view in transverse section of the dual reservoir cartridge embodiment of FIG. 8F showing a first fluid being transferred from the first syringe hub assembly embodiment of FIG. 8D to a first pump reservoir of the dual reservoir cartridge embodiment of FIG. 8A.

FIG. 8H shows the vial adapter embodiment and second vial reservoir embodiment of FIG. 8C being coupled together in order to form the vial adapter reservoir assembly embodiment.

FIG. 8I depicts the second syringe reservoir embodiment of FIG. 8C being coupled to the vial adapter reservoir assembly embodiment of FIG. 8H.

FIG. 8J depicts the second syringe reservoir embodiment of FIG. 8I coupled to a female luer adapter of the second output port of the dual reservoir cartridge embodiment of FIG. 8A.

FIG. 8K is a view in transverse section of the dual reservoir cartridge embodiment of FIG. 8J showing a second fluid being transferred from the second syringe reservoir embodiment to a second pump reservoir of the dual reservoir cartridge.

FIG. 9A illustrates an embodiment of the mechanical incompatibility between the syringe hub assembly embodiment of FIG. 8D and the male luer adapter of the first output port of the dual reservoir cartridge embodiment of FIG. 8A.

FIG. 9B illustrates an embodiment of the mechanical incompatibility between the second syringe reservoir embodiment of FIG. 8C and the input port of the dual reservoir cartridge embodiment shown in FIG. 8A.

FIG. 10E depicts a top view of the dual reservoir cartridge embodiment of FIG. 10A.

FIG. 10F is a side view of the dual reservoir cartridge embodiment of FIG. 10A.

FIG. 10G is an enlarged view of the multiple reservoir cartridge of FIG. 10E showing a first keyed input port and a second keyed input port.

FIG. 14A depicts the dual reservoir cartridge embodiment of FIG. 10A.

FIG. 14B is a view in transverse section of the dual reservoir cartridge embodiment shown in FIG. 14A.

FIG. 14C is an enlarged view of the dual reservoir cartridge embodiment shown in FIG. 14B.

FIG. 15A shows a first keyed port embodiment of the dual reservoir cartridge of FIG. 14C and the coupled first syringe reservoir embodiment and first hub assembly embodiment of FIG. 13D.

FIG. 15B is a view in transverse section of the first hub assembly embodiment of FIG. 15A.

FIG. 15C is a view in transverse section of the first keyed port embodiment of FIG. 15A.

FIG. 15D shows a first fluid communication junction embodiment created by inserting the first hub assembly embodiment of FIG. 15A into the first keyed port embodiment of FIG. 15A.

FIG. 20N shows the syringe hub assembly embodiment of FIG. 20I and a second keyed input port embodiment of the dual reservoir cartridge of FIG. 20M.

FIG. 20O is a view in transverse section of the syringe hub assembly embodiment of FIG. 20N.

FIG. 20P is a view in transverse section of the second keyed input port embodiment of FIG. 20N.

FIG. 20Q shows the syringe hub assembly embodiment of FIG. 20N inserted into the second keyed input port embodiment of FIG. 20N.

FIG. 21A illustrates an embodiment of the mechanical incompatibility between the diabetic pen reservoir embodiment of FIG. 20B and the second keyed input port embodiment of the dual reservoir cartridge of FIG. 20M.

FIG. 21B illustrates an embodiment of the mechanical incompatibility between the coupled syringe reservoir and hub assembly embodiment of FIG. 20I and a first input port embodiment of the dual reservoir cartridge FIG. 20M.

FIG. 21C is a view in transverse section of the hub assembly embodiment of FIG. 21B.

FIG. 21D is a view in transverse section of the first input port embodiment of FIG. 21B.

DETAILED DESCRIPTION

Figure 1:
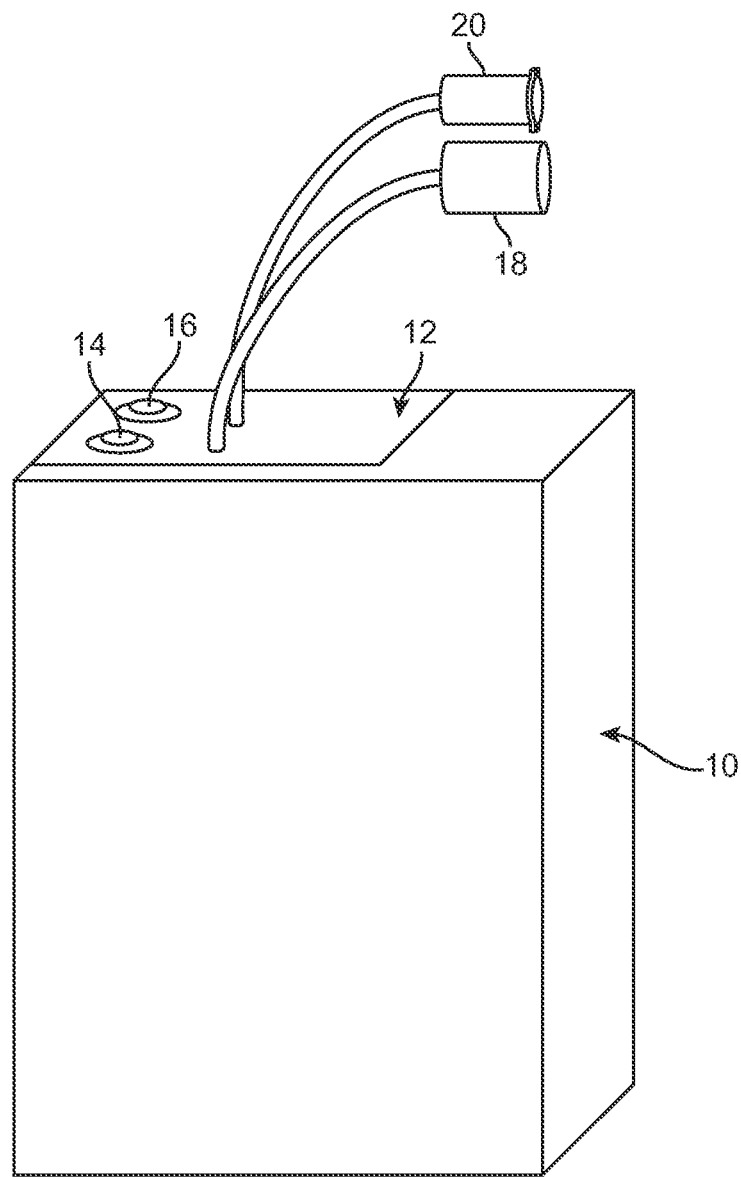
FIG. 1 is a perspective view of an embodiment of a pump device.

As discussed above, a refillable pump device which can accurately dispense multiple fluids has applications which span a wide variety of fields. The ability of the refillable pump device to dispense multiple fluids (including liquids and/or gasses) may require multiple internal reservoirs within the pump device, each with distinguishable input and output ports in some cases. The input port for each internal reservoir may serve as an access site via which a user can refill the given internal reservoir. In turn, the output port for each internal reservoir may serve as a means by which a liquid or gas can exit the pump device and be delivered to a target area. Alternatively, either output port may be used in order to refill the respective internal reservoir in fluid communication with respectively therewith.

In the case where the refillable pump device is used as a medical device for the delivery of multiple agents or medicaments, including, e.g., multiple pharmaceutical or bioactive agents wherein different volumetric doses of the different agents may be delivered to a patient or caregiver, then the proper refilling of each internal reservoir of the pump device by the user may be particularly important.

When a pump device is activated, the volumetric flow rate of a fluid from each internal reservoir may be calibrated to deliver the appropriate distinguishable doses for each agent over a desired temporal period; e.g., the period during which the pump device is activated. For diabetic indications, the patient or caregiver is typically the user who refills the pump device with insulin or other suitable medications which may include Symlin®, Byetta®, Bydureon®, Victoza®, Glucagon®, saline, antibiotics, or any other suitable medications which may be delivered subdermally or by other suitable delivery methods. The patient or caregiver can refill the respective internal reservoirs of the pump device from a variety of different external reservoir configurations which can include drug vials, insulin pen vials, and insulin pen assemblies.

For a case where a pump device includes a disposable cartridge, it may be desirable to isolate agent reservoirs and agent ports in the cartridge which can detach from a body of the pump device. The ability of the user (e.g., the patient or caregiver) to detach the cartridge from the body of the pump device may allow, for example, cartridge replacement after a specified number of uses or after the agent has been partially or completely dispensed therefrom. The pump device body may contain features such as a fluid pumping mechanism, feedback control circuitry, and patient or caregiver user interface through which the pump device may be controlled. The accompanying cartridge may contain single or multiple agent reservoirs and a single or multiple input and output ports. In the case of a cartridge having multiple reservoirs, multiple input ports may be used in order to refill the multiple internal reservoirs, whereas the multiple output ports may be used to deliver multiple agents to the patient or caregiver. For some method embodiments, it may be desirable to refill one or more of the multiple internal reservoirs using one or more of the multiple output ports.

Transferring fluids from supply reservoirs such as, e.g., syringes, vials, and insulin pens to receptacle reservoirs such as, e.g., the internal reservoirs of a pump cartridge may be accomplished any number of methods. For instance, the fluid could be transferred from a supply reservoir to a receptacle reservoir by decreasing the fluid pressure within an interior volume of the receptacle reservoir with a pump device. The fluid could also be transferred from a supply reservoir into a receptacle reservoir by increasing the fluid pressure within an interior volume of the supply reservoir with a pump device. The fluid could also be transferred from a supply reservoir to a receptacle reservoir by decreasing an internal volume of the supply reservoir with a moveable plunger that is contained within the internal volume of the supply reservoir. The fluid also could be transferred from a supply reservoir to a receptacle reservoir by increasing the internal volume of the receptacle reservoir with a moveable plunger contained within the internal volume of the receptacle reservoir.

FIGS. 1-3B illustrate an embodiment of a pump system including a multi-reservoir cartridge 12 having multiple input and output ports which can be inserted into the pump device 10 in order to deliver multiple pharmaceutical agents to a patient or caregiver. For some embodiments, it may be possible for the pump device to simultaneously deliver different doses of the different agents to the patient or caregiver. In some cases, the patient or caregiver can refill the cartridge receptacle reservoirs with the different agents from multiple supply reservoirs. It may be desirable in some cases for the various ports of the supply reservoirs and receptacle reservoirs be configured such that the possibility of patient or caregiver filling a given receptacle reservoir with an agent from the wrong supply reservoir is mechanically prevented.

Figure 2:
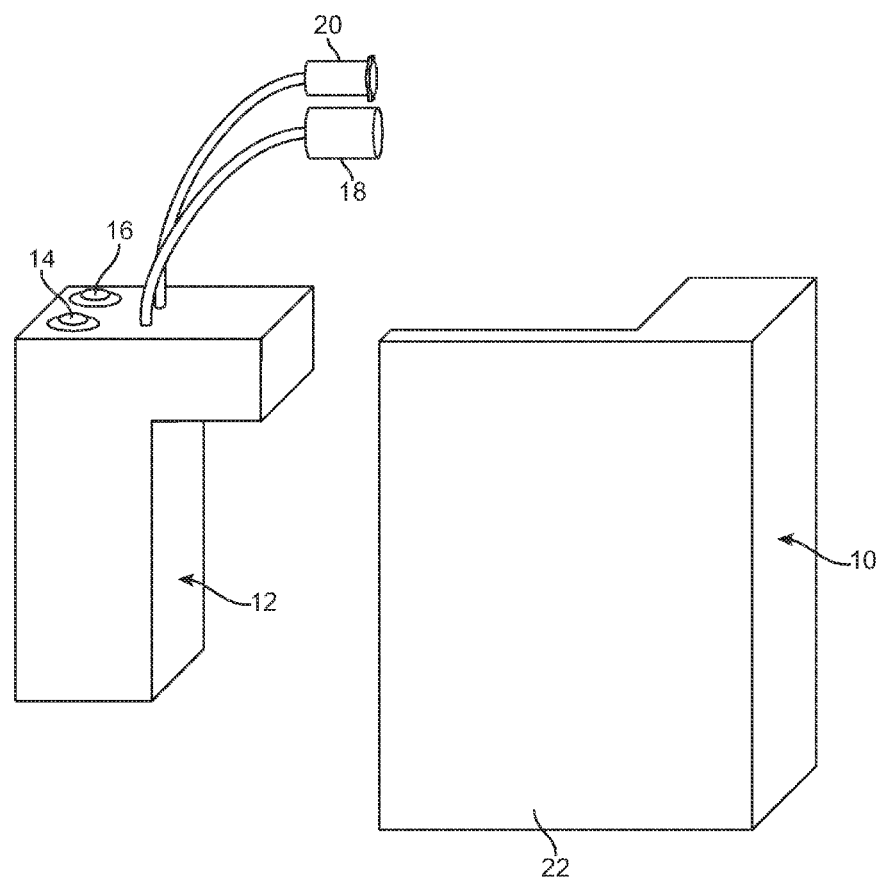
FIG. 2 shows the pump device embodiment of FIG. 1 with a dual reservoir cartridge embodiment removed from the pump device.
Figure 3:
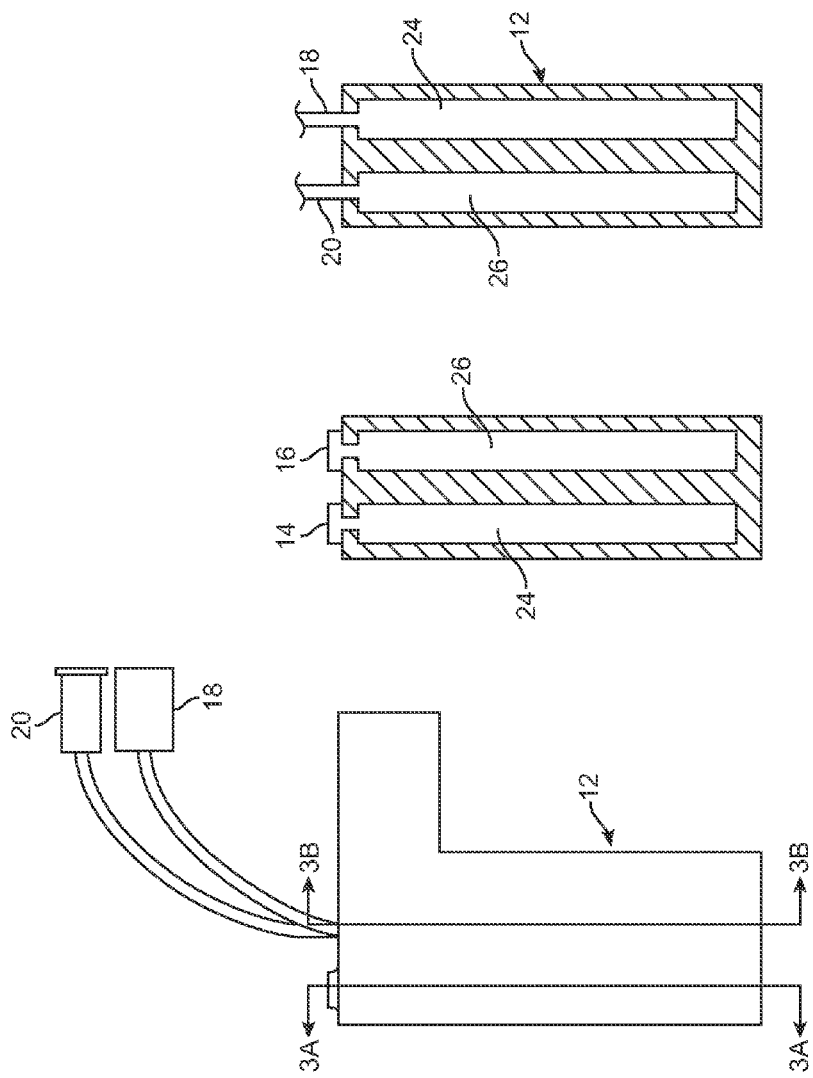
FIG. 3 shows the dual reservoir cartridge embodiment of FIG. 2.

FIG. 1 is a perspective view of a pump device embodiment 10 with a multiple reservoir cartridge embodiment 12 having multiple input and output ports. The multiple reservoir cartridge incorporates embodiments of a first input port 14, a second input port 16, a first output port 18, and a second output port 20. FIG. 2 shows the pump device 10 of FIG. 1 with the multiple reservoir cartridge 12 separated from the pump device body 22. FIG. 3 is a frontal view of the multiple reservoir cartridge 12 of FIG. 2. FIG. 3A is a transverse sectional view of the multiple reservoir cartridge 12 of FIG. 3 showing the first input port 14 which is in fluid communication with a first pump reservoir 24, and the second input port 16 which is in fluid communication with a second pump reservoir 26. FIG. 3B is a transverse sectional view of the multiple reservoir cartridge 12 of FIG. 3 showing the first output port 18 which is in fluid communication with the first pump reservoir 24, and the second output port 20 which is in fluid communication with the second pump reservoir 26.

Figure 4:
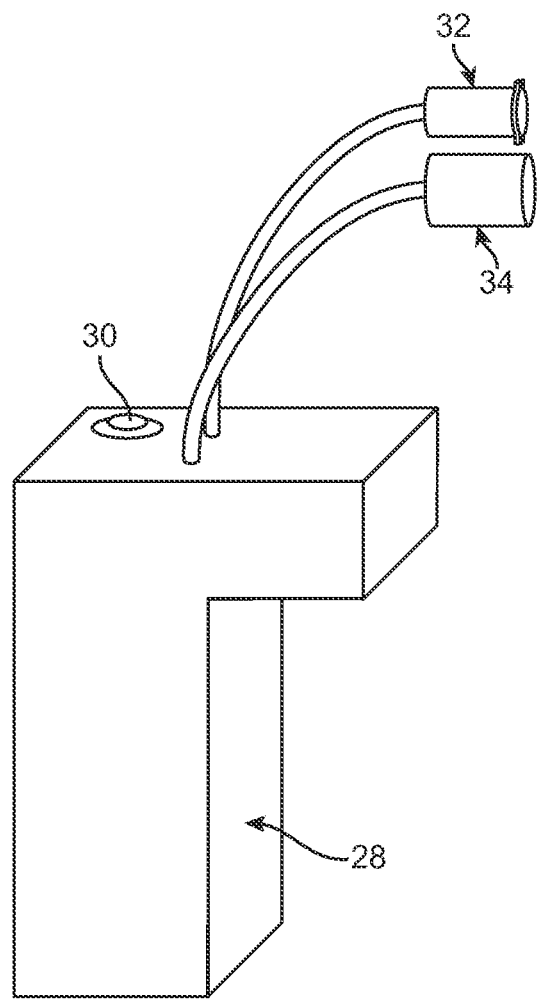
FIG. 4 is a perspective view of an embodiment of a dual reservoir cartridge.

FIG. 4 is a perspective view of a multiple reservoir cartridge 28 embodiment with a single input port and multiple output ports. The multiple reservoir cartridge 28 incorporates embodiments of an input port 30, a first output port 32, and a second output port 34. FIG. 5A is a frontal view of the multiple reservoir cartridge 28 of FIG. 4. FIG. 5B is a transverse sectional view of the multiple reservoir cartridge 28 of FIG. 5A showing the input port 30 which is in fluid communication with a second pump reservoir 38. FIG. 5C is a transverse sectional view of the multiple reservoir cartridge embodiment 28 of FIG. 5A showing the first output port 32 which is in fluid communication with a first pump reservoir 36, as well as the second output reservoir 34 which is in fluid communication with the second pump reservoir 38.

The multiple reservoir cartridges are distinguished by the configuration of each fluid interface port which is connected to each pump reservoir of the cartridge embodiment. A user may refill the pump reservoirs from multiple supply reservoirs with each fluid being delivered to its intended respective pump reservoir. Thus, the various fluid interface ports of the supply reservoirs and pump reservoirs may be mechanically configured such that the possibility of a user filling a given pump reservoir with an agent from the wrong supply reservoir is prevented. FIGS. 6A-7B illustrate such a fluid transfer system wherein multiple fluids may be transferred selectively from multiple supply reservoirs into the respective pump reservoirs of the multiple reservoir cartridge embodiment 28.

FIGS. 6A and 6H show the multiple reservoir cartridge 28 which may include a first pump reservoir 36 having a first pump reservoir body 40, a first reservoir interior volume 42 disposed within the first pump reservoir body 40, an input port 30 and a first output port 32. The first pump reservoir body 40 may be fabricated from a thin flexible material. The input port 30 may include a reservoir septum 44 which is disposed within a multiple reservoir cartridge body 46. The reservoir septum 44 may be configured to seal the first reservoir interior volume 42. The first output port 32 is in fluid communication with the first reservoir interior volume 42. The first output port 32 includes a first fluid line 48 which may be a flexible tube with an inner fluid lumen which connects the first reservoir interior volume 42 to a first output port adapter 52.

Figure 6I:
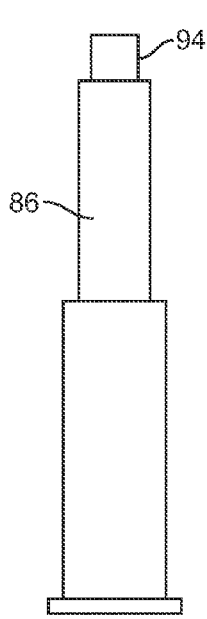
FIG. 6I shows the diabetic pen reservoir embodiment and female luer adapter embodiment both of FIG. 6B.
Figure 6J:
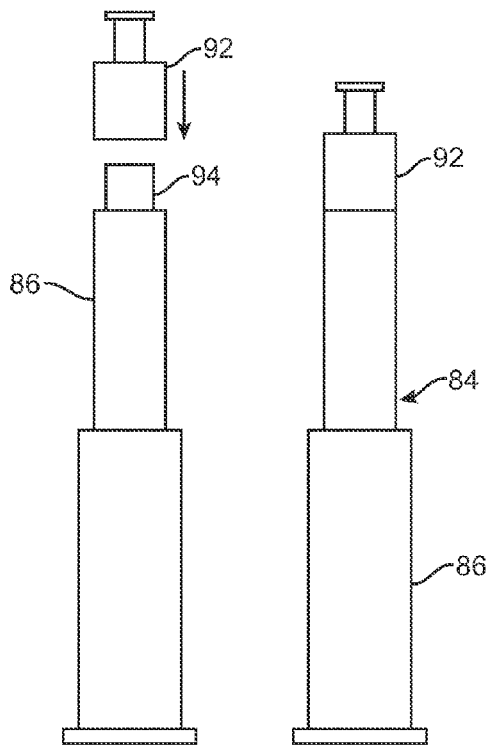
FIG. 6J shows the diabetic pen reservoir embodiment and female luer adapter embodiment of FIG. 6I coupled to form a pen reservoir assembly embodiment.
Figure 6K:
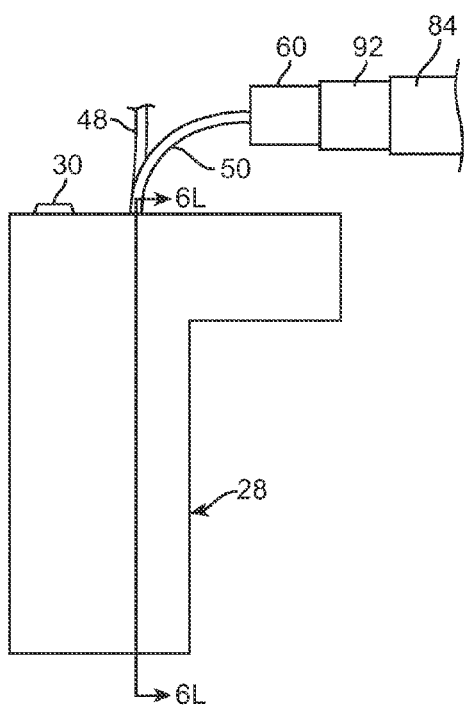
FIG. 6K shows the pen reservoir assembly embodiment of FIG. 6J coupled to a male luer adapter of a second output port of the dual reservoir cartridge of FIG. 6A.
Figure 6L:
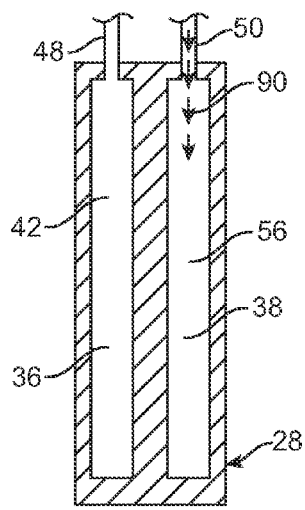
FIG. 6L is a view in transverse section of the multiple reservoir cartridge embodiment of FIG. 6K showing a second fluid being transferred from a diabetic pen reservoir to a second pump reservoir.

The fluid transfer system may also include a second pump reservoir 38 of the multiple reservoir cartridge 28, as illustrated in FIGS. 6H and 6L. The second pump reservoir 38 may include a second pump reservoir body 54, a second reservoir interior volume 56 disposed within a second pump reservoir body 54, and a second output port 34 (FIG. 6A). The second pump reservoir body 54 may be fabricated from a thin flexible material. The second output port 34 may include a second output port adapter 60 which is in fluid communication with the second reservoir interior volume 56. The second output port 34 may also include a second fluid line 50 which may be a flexible tube with an inner fluid lumen which connects the second reservoir interior volume 56 to the second output port adapter 60.

The fluid transfer system may also include a syringe hub assembly 62 which is shown in FIGS. 6C and 6E. FIG. 6C illustrates a syringe reservoir 64 and a hub assembly 66 in a decoupled state. FIG. 6E shows the syringe reservoir 64 coupled or releasably secured to the hub assembly 66 forming the syringe hub assembly 62. The syringe hub assembly 62 may include a syringe body 68, a syringe interior volume 70 disposed within the syringe body 68, a first fluid 72 contained within the syringe interior volume 70, and the hub assembly 66 which may be coupled to the syringe body 68. As shown in FIG. 6C, the syringe reservoir 64 has a syringe port 74 which may be in fluid communication with the syringe interior volume 70. The syringe reservoir 64 also has a plunger 76, which, when manipulated, can vary the volume of the syringe interior volume 70 and thereby draw a fluid into or out of the syringe interior volume 70. As also shown in FIG. 6C, the hub assembly 66 includes a tubular needle 78 sealingly secured to a hub distal section 80, and a hub proximal section 82 which is capable of coupling to the syringe port 74. The needle 78 of the hub assembly 66 shown in FIG. 6E is capable of penetrating the reservoir septum 44 of the first pump reservoir 36 but is mechanically incompatible with the second output port adapter 60 of the second pump reservoir 38.

The fluid transfer system may also include a diabetic pen reservoir assembly 84 as shown in FIGS. 6B, 6I, and 6J. The diabetic pen reservoir assembly 84 shown in FIG. 6B may include a diabetic pen reservoir body 86, a pen interior volume 88 disposed within the diabetic pen reservoir body 86, a second fluid 90 contained within the pen interior volume 88, and a diabetic pen reservoir adapter 92. The diabetic pen reservoir body 86 may include a pen port 94 which is in fluid communication with the pen interior volume 88. The pen port 94 may be capable of coupling with the diabetic pen reservoir adapter 92. FIGS. 6B and 6I show the diabetic pen reservoir adapter 92 and diabetic pen reservoir body 86 in a decoupled state, while FIG. 6J illustrates the diabetic pen reservoir adapter 92 as it is coupled to the diabetic pen reservoir body 86. The diabetic pen reservoir adapter 92 is configured to be mechanically compatible with the second output port adapter 60 and mechanically incompatible with the input port 30 of the first pump reservoir 36. For some embodiments, the second output port adapter 60 may be a male luer adapter and the diabetic pen reservoir adapter 92 may be a female luer adapter as shown in FIGS. 6A and 6B, respectively. Additionally, the input port 30 may include a channel 96 (not shown) disposed within the multiple reservoir cartridge body 46. In this case, the channel 96 transverse diameter may be too small to accept the diabetic pen reservoir adapter 92, thus providing mechanical incompatibility and preventing the creation of a fluid communication junction between the diabetic pen reservoir assembly 84 and the first pump reservoir 36.

Prior to being transferred into the first pump reservoir 36, the first fluid 72 may be transferred from a vial reservoir 98 to the syringe reservoir 64 of the syringe hub assembly 62. FIG. 6D shows the vial reservoir 98. The vial reservoir 98 has a vial interior volume 100 which contains the first fluid 72. A spigot port 102 disposed on the exterior of the vial reservoir 98 contains a vial septum 104 which seals the vial interior volume 100. FIG. 6E shows the syringe hub assembly 62 of FIG. 6C and the vial reservoir 98 of FIG. 6D. FIG. 6F depicts the needle 78 of the syringe hub assembly 62 penetrating the vial septum 104 disposed within the spigot port 102 of the vial reservoir 98 thereby creating a fluid communication junction between the vial reservoir 98 and the syringe reservoir 64. FIG. 6F also depicts the plunger 76 being activated in order to transfer the first fluid 72 from the vial reservoir 98 to the syringe reservoir 64. After the first fluid 72 has been transferred from the vial reservoir 98 to the syringe hub assembly 62, it may then be transferred into the first pump reservoir 36. Similarly, the second fluid 90 may be transferred from the diabetic pen reservoir assembly 84 to the second pump reservoir 38. The fluid transfer system illustrated in FIGS. 6A-6F may be used to achieve these fluid transfers.

Some embodiments of a method for transferring fluids using the fluid transfer system are shown in FIGS. 6H-6L. The method may include creating a first fluid communication junction between the first pump reservoir 36 and the syringe reservoir 64 by piercing the reservoir septum 44 of the first input port 30 with the needle 78 of the syringe hub assembly 62 as is shown in FIG. 6G. FIG. 6G shows the needle 78 of the syringe hub assembly 62 inserted into the input port 30 of the multiple reservoir cartridge 28. FIG. 6H is a sectional view of FIG. 6G showing the needle 78 having penetrated the reservoir septum 44. The first fluid 72 is shown being transferred from the syringe reservoir 64 to the first pump reservoir 36 through the needle 30 which is in fluid communication with the first reservoir interior volume 42. The first fluid 72 may be transferred by depressing the plunger 76 of the syringe reservoir 64. The needle 78 may be configured such that it is mechanically incompatible with the second output port adapter 60 of the second output port 34 of the second pump reservoir 38 so as to mechanically prevent coupling between the syringe reservoir 64 and the second output port 34 and the creation of a fluid communication junction between the syringe reservoir 64 and the second output port 34.

The method may also include creating a second fluid communication junction between the second pump reservoir 38 and the diabetic pen reservoir assembly 84 by coupling the second output port adapter 60 of the second output port 34 to the diabetic pen reservoir adapter 92. FIG. 6K depicts the diabetic pen reservoir assembly 84 coupled to the second output port adapter 60. FIG. 6L is a sectional view of FIG. 6K showing the second fluid 90 being transferred from the diabetic pen reservoir assembly 84 to the second reservoir interior volume 56 of the second pump reservoir 38. The diabetic pen reservoir adapter 92 is configured such that it is mechanically incompatible with the input port 30 so as to prevent the creation of a fluid communication junction between the diabetic pen reservoir adapter 92 and the input port 30.

FIGS. 6H-6L depict the successful transfer of the first fluid 72 from the syringe reservoir 64 to the first pump reservoir 36, and the transfer of the second fluid 90 from the diabetic pen reservoir assembly 84 to the second pump reservoir 38. The method embodiment discussed may be performed by a patient or caregiver filling the multiple reservoir cartridge 28 of a pump device 10 with multiple pharmaceutical agents. In some cases it may be important that during the refilling procedure each agent is delivered to its appropriate respective receptacle due to the fact that the pump device 10 may deliver different agent doses from each receptacle. The existence of mechanical incompatibilities between the various interface ports in the method discussed may be used to prevent the user from transferring the wrong agent to the wrong receptacle reservoir.

Figure 7A:
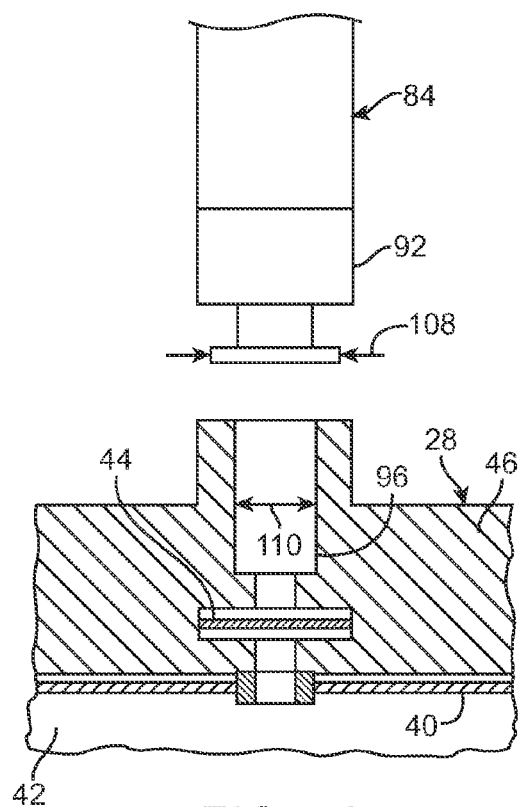
FIG. 7A illustrates an embodiment of mechanical incompatibility between the pen reservoir assembly embodiment of FIG. 6J and the input port of the dual reservoir cartridge embodiment of FIG. 6A.

In some cases the second output port adapter 60 of the fluid transfer system may be a male luer adapter and the diabetic pen reservoir adapter 92 may be a female luer adapter as shown in FIGS. 6A and 6B, respectively. Additionally, the reservoir septum 44 may be disposed within a channel 96 of the multiple reservoir cartridge body 46. In this case, if the user incorrectly attempts to transfer the second fluid 90 from the diabetic pen reservoir assembly 84 to the first pump reservoir 36, this would necessitate the attempted creation of a fluid communication junction between the diabetic pen reservoir adapter 92 and the input port 30 of the multiple reservoir cartridge 28. FIG. 7A illustrates how the mechanical incompatibility between the diabetic pen reservoir adapter 92 of the diabetic pen reservoir assembly 84 and the input port 30 (shown in the section view of FIG. 6H) prevents the creation of a fluid communication junction between the diabetic pen reservoir assembly 84 and the first pump reservoir 36.

In order to establish a fluid communication junction between the diabetic pen reservoir assembly 84 and the first pump reservoir 36, the septum 44, which seals the first reservoir interior volume 42, needs to be penetrated or otherwise interrupted. As discussed above, this may be carried out by a sharpened tubular member such as the needle 78 which is configured to reach the septum 44 and has a sharpened end which is configured to penetrate the septum 44. As shown in FIG. 7A, the outer transverse diameter 108 of the diabetic pen reservoir adapter 92 is too large to insert into the interior transverse diameter 110 of the channel 96 of the input port 30. In addition, the end of the diabetic pen reservoir adapter 92 is blunted and is not configured to penetrate the septum 44 even if the diabetic pen reservoir adapter 92 was small enough to pass through the channel 96 and reach the septum 44. For some embodiments, the septum 44 and any other such septum embodiments discussed herein may be made from or may include a layer of resilient material that resists penetration by a blunt object. For some embodiments, the septum may be made from or may include a layer of any suitable elastomeric material, including rubber or suitable polymers. Thus, the creation of a viable fluid communication junction between the two embodiments is prevented by their mechanical incompatibility.

Figure 7B:
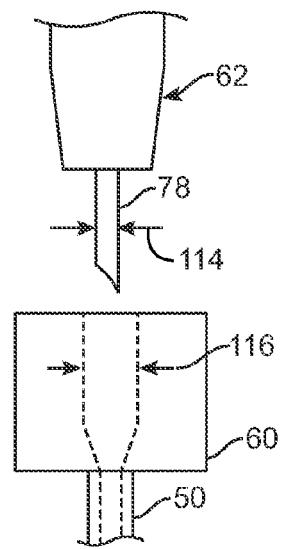
FIG. 7B illustrates an embodiment of the mechanical incompatibility between the syringe hub assembly embodiment of FIG. 6E and a male luer adapter of the first input port of the dual reservoir cartridge embodiment of FIG. 6A.

If a user attempts to transfer the first fluid from the syringe reservoir 64 to the second pump reservoir 38, this would necessitate the attempted creation of a fluid communication junction between the needle 78 of the syringe hub assembly 62 and the second output port adapter 60 of the second output port 34. FIG. 7B illustrates how the mechanical incompatibility between the needle 78 and the second output port adapter 60 mechanically prevents the creation of a fluid communication junction between the syringe reservoir 64 and the second pump reservoir 38. As shown in FIG. 7B, the outer transverse diameter 114 of the needle 78 is too small to form a fluid seal with the inner transverse diameter 116 of the second output port adapter 60. Thus, the creation of a viable fluid communication junction between the components is prevented by their mechanical incompatibility. If the needle 78 were inserted into the second output port adapter 60, any fluid dispensed from the needle 78 will leak from the gap between the outer transverse diameter 114 of the needle 78 and the inner transverse diameter 116 of the second output port adapter 60. Thus, no pressure differential would be created between the syringe reservoir 64 and the second pump reservoir 38 and therefore no fluid would be transferred into the second pump reservoir 38.

The components of an embodiment of a fluid transfer system are shown in FIG. 8A-8K. The fluid transfer system may include a multiple reservoir cartridge 118 having a first pump reservoir 120 with a first pump reservoir body 122 and a first reservoir interior volume 124 disposed within the first pump reservoir body 122. The first pump reservoir body 122 may be fabricated from a thin flexible material. The multiple reservoir cartridge may also have a multiple reservoir cartridge body 119. The first pump reservoir 120 may include an input port 126 which has a reservoir septum 128 that seals the first reservoir interior volume 124. The first pump reservoir 120 may also include a first output port 130 which is in fluid communication with the first reservoir interior volume 124. The first output port 130 may include a first fluid line 132 (which may be, e.g., a flexible tube) which has an inner lumen and which connects the first reservoir interior volume to a first output port adapter 134.

The multiple reservoir cartridge 118 of FIG. 8A may also include a second pump reservoir 136 which may have a second pump reservoir body 138 and a second reservoir interior volume 140 disposed within the second pump reservoir body 138. The second pump reservoir body 138 as shown in FIG. 8G may be fabricated from a thin flexible material. The second pump reservoir 136 may also include a second output port 142 which may be in fluid communication with the second reservoir interior volume 140. The second output port 142 may include a second fluid line 144 which may be a flexible tube which has an inner lumen and which connects the second reservoir interior volume 140 to a second output port adapter 146.

The fluid transfer system may also include a syringe hub assembly 148 as shown in FIG. 8D. The syringe hub assembly 148 includes a first syringe reservoir 150 and a hub assembly 152, both of which are shown in FIG. 8B. The first syringe reservoir 150 shown in FIG. 8B may include a first syringe body 154 and a first syringe interior volume 156 disposed within the first syringe body 154. The first syringe body 154 may also include a first syringe port 158 which is capable of coupling with the hub assembly 152. The first syringe reservoir 150 may also have a first plunger 160 which may form a slidable fluid tight seal against an inner surface of a bore of the interior volume and when manipulated can vary the volume of the first syringe interior volume 156 and thereby transfer a fluid into or out of the first syringe interior volume 156. The hub assembly 152 includes a tubular needle 162 having an inner lumen, the tubular needle being sealingly secured to a hub distal section 164 and a hub proximal section 166 which is capable of coupling to the first syringe port 158. The needle 162 of the hub assembly 152 shown in FIG. 8B is capable of penetrating the reservoir septum 128 of the first pump reservoir 120, but is mechanically incompatible with the second output port adapter 146 of the second pump reservoir 136. FIG. 8D shows the hub assembly 152 coupled to the first syringe reservoir 150, thus forming the syringe hub assembly 148. The hub assembly 152 is coupled or releasably secured to the first syringe reservoir 150.

A first vial reservoir 168 is shown in FIG. 8B. The first vial reservoir 168 has a first vial interior volume 170. A first spigot port 174 disposed on the exterior of the first vial reservoir contains a first vial septum 176 which seals the first vial interior volume 170. The first vial interior volume 170 contains a first fluid 172.

FIG. 8C includes three more components of the fluid transfer system, a vial adapter 178, a second vial reservoir 180, and a second syringe reservoir 182. The second vial reservoir 180 shown in FIG. 8C has a second vial interior volume 184 which contains a second fluid 186. A second spigot port 188 disposed on the exterior of the second vial reservoir 180 contains a second vial septum 190 which seals the second vial interior volume 184. The second syringe reservoir 182 may include a second syringe body 192 and a second syringe interior volume 194 disposed within the second syringe body 192. The second syringe body 192 may also include a second syringe port 198 which is configured for coupling with the vial adapter 178. The second syringe port 198 is contiguously formed into the second syringe body 192. The second syringe reservoir 182 may also have a second plunger 200 which forms a fluid tight slidable seal against an inner bore of the interior volume and when manipulated can vary the volume of the second syringe interior volume 194 and thereby draw a fluid into or out of the second syringe interior volume 194.

The vial adapter 178 shown in FIG. 8C has a proximal section 202 that is capable of coupling to the second vial reservoir 180 and forming a fluid communication junction with the second vial interior volume 184. The vial adapter 178 also has a distal section 204 that is capable of coupling to the second syringe port 198. The second syringe port 198 is configured such that it is capable of coupling to the second output port adapter 146 so as to form a fluid communication junction. The second syringe port 198 is also configured such that it is mechanically incompatible with the input port 126 so as to prevent a fluid communication junction between the two components.

Prior to being transferred into the first pump reservoir 120, the first fluid 172 may be transferred from the first vial reservoir 168 to the first syringe reservoir 150 of the syringe hub assembly 148. FIG. 8E shows the needle 162 of the syringe hub assembly 148 having penetrated the first vial septum 176 (shown in FIG. 8B) of the first vial reservoir 168. Also shown in FIG. 8E is the first plunger 160 being drawn back, thereby transferring the first fluid 172 from the first vial reservoir 168 to the first syringe reservoir 148. In a similar manner, before the second fluid 186 is transferred into the second pump reservoir 136, the second fluid 186 may be transferred from the second vial reservoir 180 to the second syringe reservoir 182. FIG. 8H depicts the coupling of the vial adapter 178 and the second vial reservoir 180. FIG. 8I shows the second syringe port 198 of the second syringe reservoir 182 being coupled to the distal section 204 vial adapter 178. After the vial adapter 178 has been coupled to the second syringe reservoir 182, the second fluid 186 may be transferred from the second vial reservoir 180 to the second syringe reservoir 182.

Some embodiments of a method for transferring fluids using the fluid transfer system are shown in FIGS. 8F, 8G, 8J, and 8K. Some method embodiments may include creating a first fluid communication junction between the first pump reservoir 120 and the first syringe reservoir 150 by a piercing the reservoir septum 128 of the input port 126 of the first pump reservoir 120 with the needle 162 of the syringe hub assembly 148 as is illustrated in FIG. 8F. FIG. 8G is a sectional view of FIG. 8F showing the needle 162 having penetrated the reservoir septum 128. FIG. 8G also depicts the transferring of the first fluid 172 from the first syringe reservoir 150 to the first pump reservoir 120. The needle 162 may be configured such that it is mechanically incompatible with the second output port adapter 146 of the second pump reservoir 136 so as to prevent the creation of a fluid communication junction between the first syringe reservoir 150 and the second output port 142.

The method may also include creating a second fluid communication junction between the second pump reservoir 136 and the second syringe reservoir 182 by coupling the second output port adapter 134 of the second pump reservoir 136 to the second syringe port 198 of the second syringe reservoir 182 as is shown in FIG. 8J. FIG. 8K is a sectional view of FIG. 8J showing the second fluid 186 being transferred from the second syringe reservoir 182 to the second pump reservoir 136. The second syringe port 198 is configured such that it is mechanically incompatible with the input port 126 so as to prevent the creation of a fluid communication junction between the second syringe reservoir 182 and the first pump reservoir 120 if such a fluid communication junction is attempted by a user.

With regard to the method shown in FIGS. 8E-8K, there may be mechanical compatibilities and mechanical incompatibilities configured into the various port interfaces which are used to transfer the fluids between the respective supply and receptacle reservoirs. The purpose of the mechanical incompatibilities is to prevent the user from transferring the first fluid 172 from the first syringe reservoir 150 to the second pump reservoir 136, and/or from transferring the second fluid 186 from the second syringe reservoir 182 to the first pump reservoir 120. These mechanical compatibilities and incompatibilities may be incorporated into structures such as second output port adapter 146 and the hub assembly 152, as well as into the second syringe port 198 and the input port 126.

In some cases, the second output port adapter 146 of the fluid transfer system may be configured as a female luer adapter as shown in FIG. 8A and the second syringe port 198 may be configured as a male luer adapter as shown in FIG. 8C. Additionally, the reservoir septum 128 may be disposed within a channel 206 of the multiple reservoir cartridge body 119. If a user incorrectly attempts to transfer the first fluid 172 from the first syringe reservoir 150 to the second pump reservoir 136, this would necessitate the attempted creation of a fluid communication junction between the needle 162 of the hub assembly 152 and the second output port adapter 146 of the second output port 142.

FIG. 9A illustrates how the mechanical incompatibility between needle 162 and the second output port adapter 146 prevents the creation of a viable fluid communication junction between the first syringe reservoir 150 and the second pump reservoir 136. As shown in FIG. 9A, an exterior transverse diameter 208 of the needle 162 is too small to form a fluid seal with an interior transverse diameter 210 of the second output port adapter 146. Thus, the creation of a viable fluid communication junction between the two embodiments is prevented by their mechanical incompatibility. In some cases, if the needle 162 is inserted into the second output port adapter 146, any fluid dispensed from the needle 162 will leak from the gap between the exterior transverse diameter 208 of the needle 162 and the interior transverse diameter 210 of the second output port adapter 146.

If the user attempts to transfer the second fluid 186 from the second syringe reservoir 182 to the first pump reservoir 120, this would necessitate the attempted creation of a fluid communication junction between the second syringe port 198 of the second syringe reservoir 182 and the channel 206 of the input port 126. FIG. 9B illustrates how the mechanical incompatibility between the second syringe port 198 and the input port 126 (shown in section view see FIG. 8) prevents the creation of a fluid communication junction between the second syringe reservoir 182 and the first pump reservoir 120.

In order to create a fluid communication junction between the second syringe reservoir 182 and the first pump reservoir 120, the reservoir septum 128, which seals the first reservoir interior volume 124, needs to be penetrated or otherwise interrupted. As discussed above, this may be carried out by a sharpened tubular member such as the needle 162 which is configured to reach the reservoir septum 128 and which has a sharpened distal end configured to penetrate the reservoir septum 128. As shown in FIG. 9B, the exterior transverse diameter 212 of the second syringe port 198 is too large to insert into the interior transverse diameter 214 of the channel 206. In addition, the second syringe port 198 is blunted and is not configured to penetrate the reservoir septum 128 even if the if the second syringe port 198 was small enough to pass through the channel 206 and reach the reservoir septum 128. The creation of a viable fluid communication junction between the two embodiments is thereby prevented by their mechanical incompatibility.

Figure 10A:
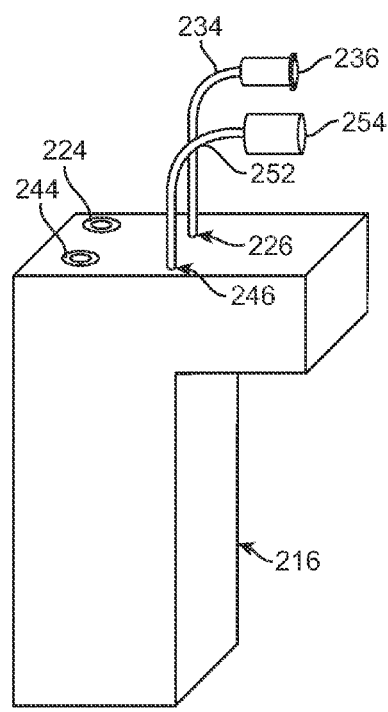
FIG. 10A is a perspective view of a dual reservoir cartridge embodiment with multiple keyed inputs and multiple outputs.

FIGS. 10A-10D depict the components of a fluid transfer system embodiment. FIG. 10A shows a multiple reservoir cartridge embodiment 216. The multiple reservoir cartridge 216 may include a first pump reservoir 218 (as shown in FIG. 14C) having a first pump reservoir body 220 which may have a first reservoir interior volume 222 disposed within it. The first pump reservoir body 220 may be fabricated from a thin flexible material. The first pump reservoir 218 may also include a first keyed port 224 and a first output port 226. The first keyed 224 port may include a first channel 228 which is in fluid communication with the first reservoir interior volume 222. The first channel 228 may incorporate a first reservoir septum 230 which is disposed within a multiple reservoir cartridge body 232 and which seals the first channel 228. The first output port 226 may include a first fluid line 234 that may be a flexible tube. The first fluid line 234 is in fluid communication with the first reservoir interior volume 222 and is attached to a first output port adapter 236.

The multiple reservoir cartridge 216 of FIG. 10A may also include a second pump reservoir 238 (as shown in FIG. 14C) having a second pump reservoir body 240 which may have a second reservoir interior volume 242 disposed within it. The second pump reservoir body 240 may be fabricated from a thin flexible material. The second pump reservoir 238 may also include a second keyed port 244 and a second output port 246. The second keyed port 244 may include a second channel 248 which is in fluid communication with the second reservoir interior volume 242. The second channel 248 may incorporate a second reservoir septum 250 which is disposed within the multiple reservoir cartridge body 232 and which seals the second channel 248. The second output port 246 may include a second fluid line 252 that may be a flexible tube having an inner lumen or conduit extending therein. The second fluid line 252 is in fluid communication with the second reservoir interior volume 242 and is attached to a second output port adapter 254.

Figure 10B:
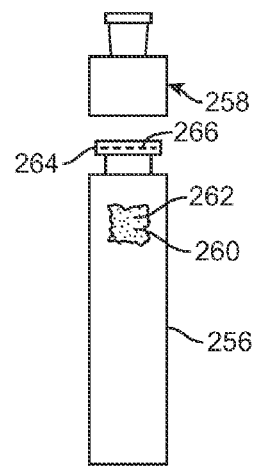
FIG. 10B shows embodiments of a first vial reservoir and a first vial adapter assembly.
Figure 10C:
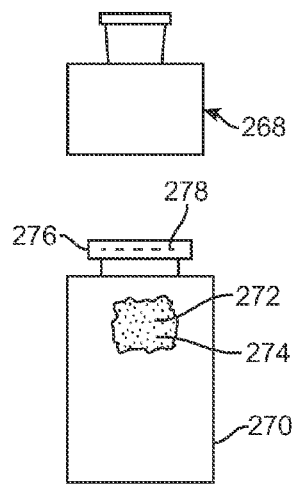
FIG. 10C shows embodiments of a second vial reservoir and a second vial adapter assembly.

The fluid transfer system may also include a first vial reservoir 256 and a first vial adapter assembly 258, Both components are shown in FIG. 10B. The first vial reservoir 256 has a first vial interior volume 260 which contains a first fluid 262. A first spigot port 264 disposed on the exterior of the first vial reservoir 256 contains a first vial septum 266 which seals the first vial interior volume 260 from the surrounding environment. FIG. 10C shows a second vial adaptor assembly 268 and a second vial reservoir 270. The second vial reservoir 270 shown in FIG. 10C has a second vial interior volume 272 which contains a second fluid 274. A second spigot port 276 disposed on the exterior of the second vial reservoir 270 contains a second vial septum 278 which seals the second vial interior volume 272.

Figure 10D:
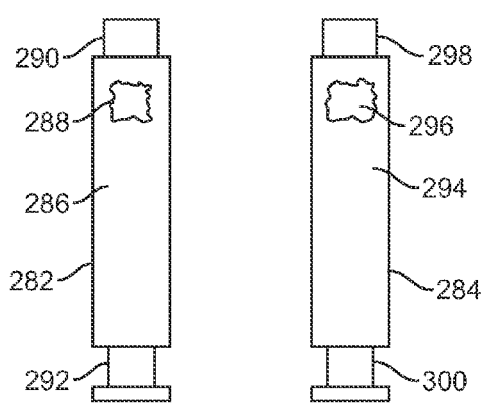
FIG. 10D shows embodiments of a first syringe reservoir and a second syringe reservoir.

The fluid transfer system may also include a first syringe reservoir 282 and a second syringe reservoir 284, both of which are shown in FIG. 10D. The first syringe reservoir 282 shown in FIG. 10D may include a first syringe body 286 and a first syringe interior volume 288 disposed within the first syringe body 286. The first syringe body 286 may also include a first syringe port 290. The first syringe reservoir 282 may also have a first plunger 292 which may be slidingly sealed to an inner bore of the interior volume and when manipulated can vary the volume of the first syringe interior volume 288 and thereby draw a fluid into or out of the first syringe interior volume 288. The second syringe reservoir 284 is also shown in FIG. 10D and may include a second syringe body 294 and a second syringe interior volume 296 disposed within the second syringe body 294. The second syringe body 294 may also include a second syringe port 298. The second syringe reservoir 284 may also have a second plunger 300 which may be slidingly sealed against an inner bore of the interior volume 296 and when manipulated can vary the volume of the second syringe interior volume 296 and thereby draw a fluid into or out of the second syringe interior volume 296. FIGS. 10E-10G show the multiple reservoir cartridge 216 of FIG. 10A. FIG. 10G depicts an enlarged view of the multiple reservoir cartridge 216 which shows the first keyed port 224 and the second keyed port 244.

Figure 11A:
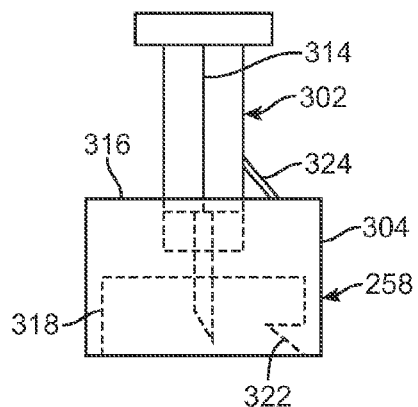
FIGS. 11A and 11B depict a first vial adapter assembly embodiment.
Figure 11B:
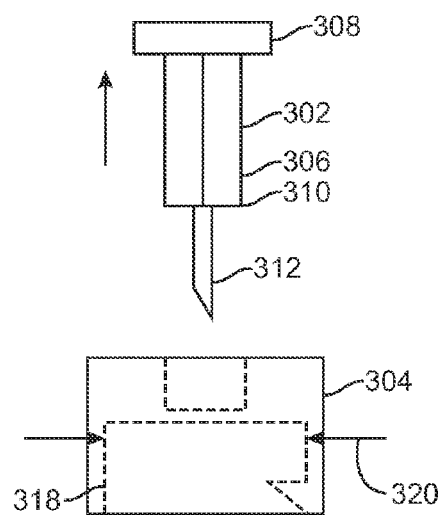

FIG. 11A shows the first vial adapter assembly 258 which may include a first hub assembly 302 and a first vial adapter 304. The first hub assembly 302 may include a first hub body 306 having a proximal section 308 which is capable of mating with a syringe port, and a distal section 310 which is sealingly secured to a first tubular needle 312 as shown in FIG. 11B. The first needle 312 may be fabricated from stainless steel or any other suitable metal, and the first needle 312 can vary in gauge size from about 16 gauge to about 30 gauge. The first hub assembly 302 may also include a first hub key feature 314 that is mechanically compatible with the first keyed port 224, but is mechanically incompatible with the second keyed port 244. The first hub body 306 and first hub key feature 314 may be fabricated from any suitable polymer.

The first vial adapter 304 may include a first vial adapter body 316 having a first distal cavity 318 which may be fabricated such that it has a substantially cylindrical configuration and which has an interior transverse dimension 320 as shown in FIG. 11B configured to couple to the first spigot port 264 of the first vial reservoir 256 but not couple to the second spigot port 276 of the second vial reservoir 270. The first vial adapter body 316 may be fabricated from any suitable polymer or other material. The first distal cavity 318 may also include at least one first hooked clip 322 capable of engaging with the first spigot port 264 but not the second spigot port 276. FIG. 11A also shows a first engagement feature 324 which may releasably secure the first hub body 306 to the first vial adapter body 316 such that the first needle 312 is disposed within and is in axial alignment of the first distal cavity 318. FIG. 11B shows the first hub assembly 302 separated from the first vial adapter 304 after the first engagement feature 324 has been disengaged. The first engagement feature 324 is shown in FIG. 11A as a break away rib; however, the first engagement feature 324 could also be configured as a threaded section on the first hub body 306 and a corresponding threaded section on the first vial adapter body 316 which would allow for the coupling of the two components.

Figure 11C:
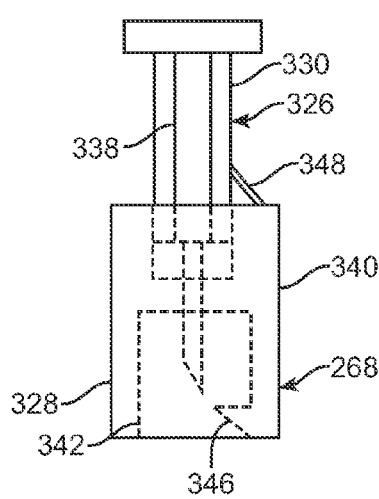
FIGS. 11C and 11D depict a second vial adapter assembly embodiment.
Figure 11D:
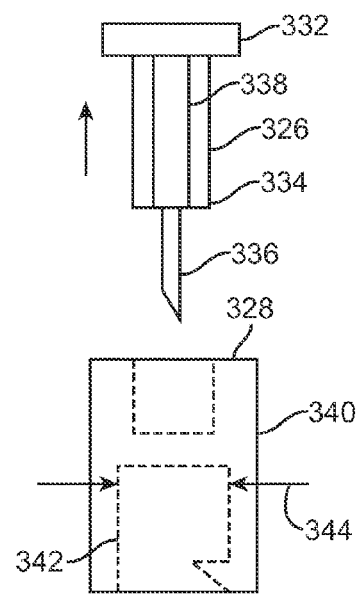

FIG. 11C shows the second vial adapter assembly 268 which may have a second hub assembly 326 and a second vial adapter 328. The second hub assembly 326 may include a second hub body 330 which has a proximal section 332 configured for mating with a syringe port, and a distal section 334 which is sealingly secured to a second tubular needle 336 as shown in FIG. 11D. The second needle 336 may be fabricated from stainless steel or any other suitable metal, and the second needle 336 can vary in gauge size from about 16 gauge to about 30 gauge. The second hub assembly 326 may also include a second hub key feature 338 that is mechanically compatible with the second keyed port 244, but is mechanically incompatible with the first keyed port 224. The second hub body 330 and second hub key feature 338 may be fabricated from any suitable polymer.

The second vial adapter 328 may include a second vial adapter body 340 having a second distal cavity 342 which may be fabricated such that it has a substantially cylindrical configuration and which has an interior transverse dimension 344 as shown in FIG. 11D configured to couple to the second spigot port 276 of the second vial reservoir 270 but not couple to the first spigot port 264 of the first vial reservoir 256. The second vial adapter body may be fabricated from any suitable polymer. The second distal cavity 342 may also include at least one second hooked clip 346 which is configured for engaging with and mechanically capturing the second spigot port 276 but not the first spigot port 264. FIG. 11C also shows a second engagement feature 348 which may releasably secure the second hub body 330 to the second vial adapter body 340 such that the second needle 336 is disposed within and is in axial alignment of the second distal cavity 342. The second engagement feature 348 may be configured as a breakable link or connection that may be configured to be separated by firmly applied manual force but not casual or incidental manual force, other similar engagement features discussed herein may be similarly configured. FIG. 11D shows the second hub assembly 326 separated from the second vial adapter 328 after the second engagement feature 348 has been disengaged. The second engagement feature 348 is shown in FIG. 11C as a break away rib; however, the second engagement feature 348 could also be configured as a threaded section on the second hub body 330 and a corresponding threaded section on the first vial adapter body 340 which would allow for the coupling of the two components.

The first keyed port 224 shown in FIG. 10G may include the first channel conduit 228 which is in fluid communication with the first reservoir interior volume 222 of the first pump reservoir 218. The reservoir interior volume 222 and any other similarly used reservoir interior volume discussed herein may be configured as an enclosed or substantially enclosed volume surrounded by an inner surface that is sealed and configured to confine a fluid such as a liquid medicament therein. The first channel 228 may be configured as a female receptacle such that it can accommodate the insertion of the first hub body 306. The first reservoir septum 230 may be disposed within and seals the first channel 228, and may be positioned at a depth 394 (see FIG. 15A) within the first channel 228 that is substantially equal to or greater than a distance 376 (see FIG. 12A) that the first needle 312 extends from the first hub body 306. The first keyed port 224 may also include a first port key feature 350 which is disposed on an inner perimeter 352 of the first channel 228, and which is configured to couple with the first hub key feature 314 but which is mechanically incompatible with the second hub key feature 338. The first port key feature 350 may include a first circular array of oblong slots 354 running parallel to a first channel central axis 356 and positioned around the perimeter 352 of the first channel 228.

The second keyed port 244 shown in FIG. 10G may include the second channel 248 which is in fluid communication with the second reservoir interior volume 242 of the second pump reservoir 238. The second channel 248 may be configured as a female receptacle such that it can accommodate the insertion of the second hub body 330. The second reservoir septum 250 is disposed within and seals the second channel 248 from an outside environment, and is positioned at a depth 398 (see FIG. 16A) within the second channel 248 that is substantially equal to or greater than a distance 388 (see FIG. 12C) that the second needle 336 extends from the second hub body 330. The second keyed port 244 may also include a second port key feature 358 which is disposed on an inner perimeter 360 of the second channel 248, and which is configured to couple with the second hub key feature 338 but which is mechanically incompatible with insertion of the first hub key feature 314. The second port key feature 358 may include a second circular array of oblong slots 362 running parallel to a second channel central axis 364 and positioned around the perimeter 360 of the second channel 248.

Figure 12A:
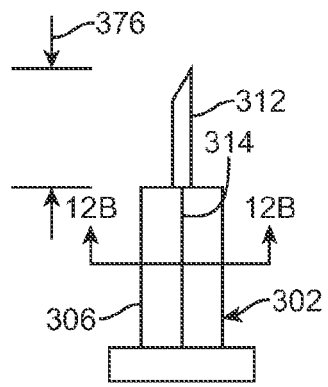
FIG. 12A depicts a first hub assembly embodiment.
Figure 12B:
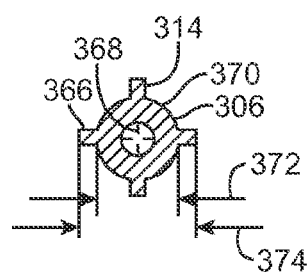
FIG. 12B is a transverse sectional view of the first hub assembly embodiment of FIG. 12A.

FIGS. 12A and 12B show the first hub assembly 302 with the first hub key feature 314. The first hub key feature 314 may include a first circular array of oblong bosses 366 running parallel to a first hub central axis 368 and positioned around the perimeter 370 of the first hub body 306. FIGS. 12A and 12B also show multiple dimensions of various device components including a first hub body diameter 372, a first hub key feature diameter 374, and the distance that the first needle extends from the first hub body 376. The first circular array of bosses 366 which include the first hub key feature 314 may be axially positioned such that they are substantially in axial alignment with the first circular array of slots 354 of the first port key feature 350 shown in FIG. 10G. The axial alignment of the first circular array of bosses 366 and the first circular array of slots 354 allows for the insertion of the first hub assembly 302 into the first keyed port 224 with the bosses 366 sliding within respective slots 354.

Figure 12C:
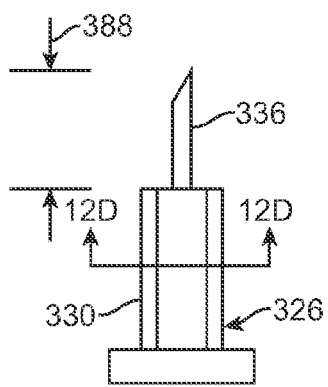
FIG. 12C depicts a second hub assembly embodiment.
Figure 12D:
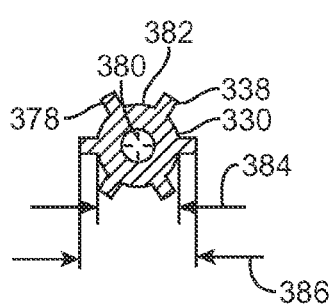
FIG. 12D is a view in transverse section of the second hub assembly embodiment of FIG. 12C.

FIGS. 12C and 12D show the second hub assembly 326 with the second hub key feature 338. The second hub key feature 338 may include a second circular array of oblong bosses 378 running parallel to a second hub central axis 380 and positioned around the perimeter 382 of the second hub body 330. FIGS. 12C and 12D also show multiple dimensions including a second hub body diameter 384, a second hub key feature diameter 386, and a distance that the second needle extends from the second hub body 388. The second circular array of bosses 378 which constitute the second hub key feature 338 are axially positioned such that they are substantially in axial alignment with the second circular array of slots 362 of the second port key feature 358 shown in FIG. 10G. The axial alignment of the second circular array of bosses 378 and the second circular array of slots 362 are configured to allow for the insertion of the second hub assembly 326 into the second keyed port 244 with the bosses 378 sliding within respective slots 362. If there is no corresponding slot 362 for each boss 378, with a matched or paired circumferential spacing, a front edge of the impaired boss 378 will impinge upon the top surface of the keyed port 244 thereby creating mechanical incompatibility and preventing insertion of the hub assembly 326.

Figures 13A, 13B:
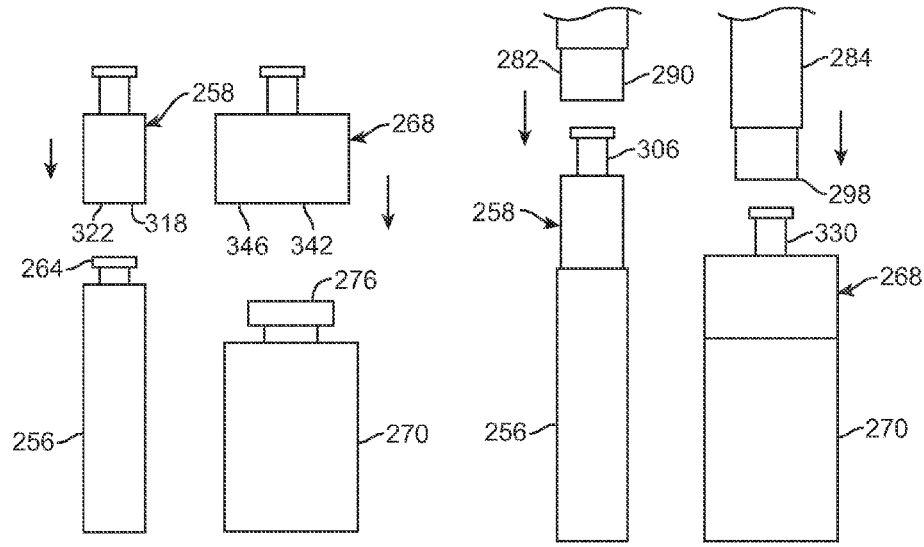
FIG. 13A-13B depict respective coupling embodiments of the first vial adapter assembly embodiment of FIG. 10B to the first vial reservoir embodiment of FIG. 10B and the second vial adapter assembly embodiment of FIG. 10C to the second vial reservoir embodiment of FIG. 10C.

The fluid transfer system embodiments discussed above may be used in order to safely transfer fluids from an appropriate supply reservoir to an appropriate receptacle reservoir. FIG. 13A shows the coupling the first vial adapter assembly 258 to the first vial reservoir 256 (both of FIG. 10B) by the insertion of the first spigot port 264 into the first distal cavity 318 such that the first needle 312 punctures the first vial septum 266 and the first vial adapter assembly 258 may be mechanically captured to the first vial reservoir 256 by the first hooked clip 322. FIG. 13A also shows the coupling the second vial adapter assembly 268 to the second vial reservoir 270 (both of FIG. 10C) by the insertion of the second spigot port 276 into the second distal cavity 342 such that the second tubular needle 336 punctures the second vial septum 278 and the second vial adapter assembly 268 is mechanically captured to the second vial reservoir 270 by the second hooked clip 346 with an inner lumen of the tubular needle 336 in fluid communication with an interior volume of the second vial reservoir 270.

Figures 13C, 13D:
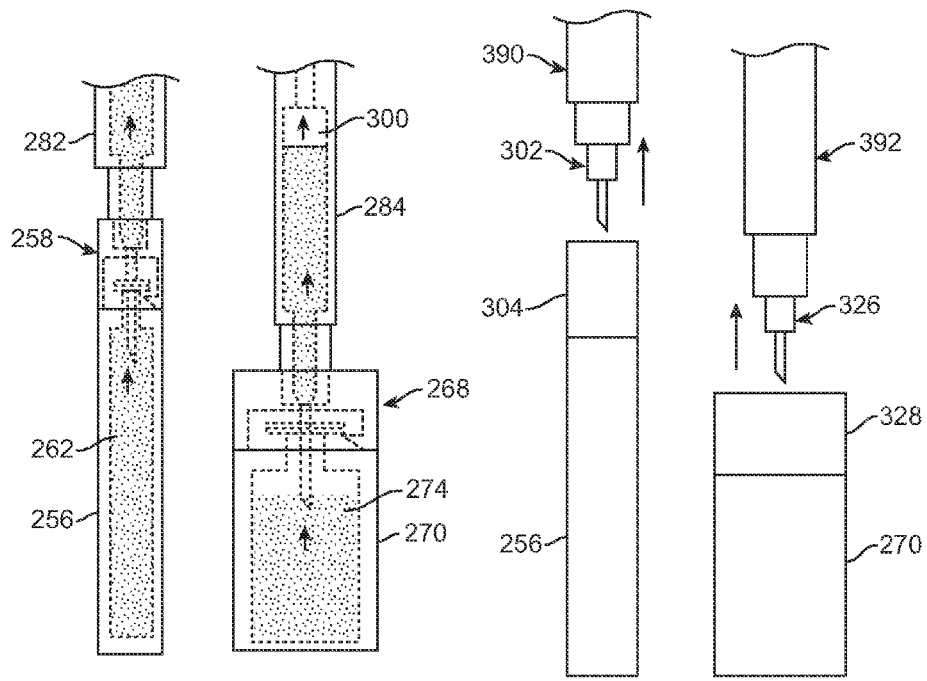
FIG. 13C depicts a coupling embodiment of the first syringe reservoir embodiment of FIG. 10D to the first vial adapter assembly embodiment of FIG. 13B as well as a coupling embodiment of the second syringe reservoir embodiment of FIG. 10D to the second vial adapter assembly embodiment of FIG. 13B.
FIG. 13D depicts a first hub assembly embodiment being uncoupled from the first vial adapter body embodiment of FIG. 13C as well as a second hub assembly embodiment being uncoupled from the second vial adapter body embodiment of FIG. 13C.

FIG. 13B depicts the coupling of the first syringe reservoir 282 of FIG. 10D to the first vial adapter assembly 258 by coupling the first syringe port 290 to the first hub body 306. FIG. 13B also depicts the coupling of the second syringe reservoir 284 of FIG. 10D to the second vial adapter assembly 268 by coupling the second syringe port 298 to the second hub body 330. FIG. 13C depicts the first fluid 262 being transferred from the first vial reservoir 256 to the first syringe reservoir 282 through the first vial adapter assembly 258. FIG. 13C also shows the second fluid 274 being transferred from the second vial reservoir 270 to the second syringe reservoir 284 through the second vial adapter assembly 268. FIG. 13D depicts the detachment of the first hub assembly 302 from the first vial adapter 304 after the disengagement of the first engagement feature 324, thus creating the first syringe hub assembly 390, with the first hub assembly 302 releasably secured to the first syringe reservoir 282. FIG. 13D also depicts the detachment of the second hub assembly 326 from the second vial adapter 328 after the disengagement of the second engagement feature 348, thus creating the second syringe hub assembly 392, with the second hub assembly 326 releasably secured to the second syringe reservoir 284.

FIGS. 14A-14C show the multiple reservoir cartridge 216 of FIG. 10A. FIG. 14A is a perspective view of the multiple reservoir cartridge 216, while FIG. 14B is a sectional view of the multiple reservoir cartridge 216. FIG. 14C is an enlarged detail view of FIG. 14B; the purpose of FIG. 14C is to illustrate the enlarged sectional views of the first keyed port 224 and the second keyed port 244. FIG. 15A shows the first syringe hub assembly 390 and the first keyed port 224. FIG. 15B is a transverse cross sectional view of the first hub body 306, and FIG. 15C is a transverse cross sectional view of the first keyed port 224. The first syringe hub assembly 390 may be inserted into the first keyed port 224 as shown in FIG. 15D. The axial alignment and common circumferential spacing of the first circular array of bosses 366 and the first circular array of slots 354 allows for the insertion of the first hub assembly 302 into the first keyed port 224 with each boss 366 sliding within a respective slot 354. Also a first channel diameter 396 maybe configured to allow for the insertion of the first hub body 306 having first hub body diameter 372. As shown in FIG. 15D, the first tubular needle 312 has penetrated the first reservoir septum 230 thus creating a first fluid communication junction between the first syringe reservoir 282 and the first reservoir interior volume 222 through an inner lumen of the tubular needle 312. FIG. 15D also shows the first fluid 262 being transferred from the first syringe reservoir 282 to the first reservoir interior volume 222.

Figure 16A:
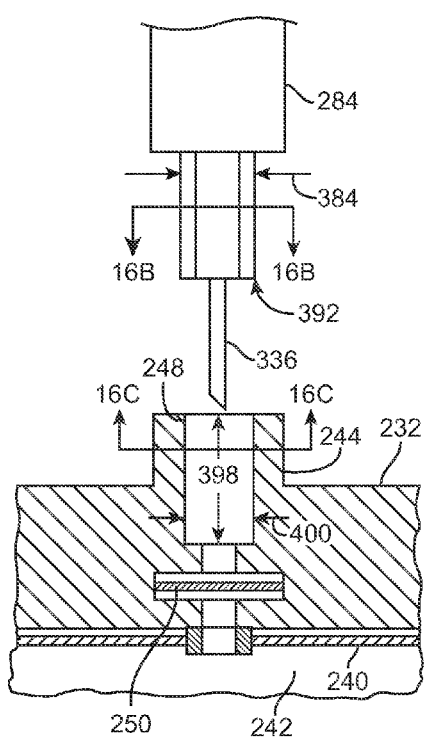
FIG. 16A shows a second keyed port embodiment of the dual reservoir cartridge of FIG. 14C and the coupled second syringe reservoir embodiment and the second hub assembly embodiment of FIG. 13D.
Figure 16B:
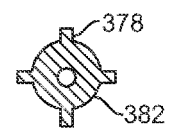
FIG. 16B is a view in transverse section of the second hub assembly embodiment of FIG. 16A.
Figure 16C:
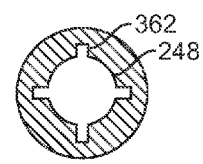
FIG. 16C is a view in transverse section of the second keyed port embodiment of FIG. 16A.
Figure 16D:
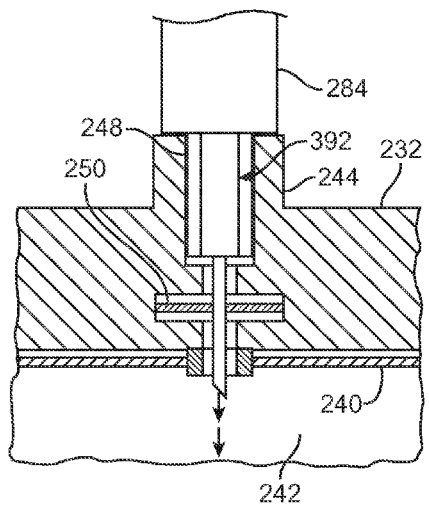
FIG. 16D shows a second fluid communication junction embodiment created by inserting the second hub assembly embodiment of FIG. 16A into the second keyed port embodiment of FIG. 16A.

FIG. 16A shows the second syringe hub assembly 392 and the second keyed port 244. FIG. 16B is a transverse cross sectional view of the second hub body 330, and FIG. 16C is a transverse cross sectional view of the second keyed port 244. As shown in FIG. 16D, the second syringe hub assembly 392 is mechanically compatible with the second keyed port 244 and may be inserted into the second keyed port 244. The axial alignment and matching circumferential spacing of the second circular array of bosses 378 and the second circular array of slots 362 allows for the insertion of the second hub assembly 326 into the second keyed port 244. Also, a second channel diameter 400 may be configured to allow for the insertion of the second hub body 330 having second hub body diameter 384. As shown in FIG. 16A, the second tubular needle 336 has penetrated the second reservoir septum 250 thus creating a second fluid communication junction between the second syringe reservoir 284 and the second reservoir interior volume 242 through the inner lumen of the second tubular needle 336. FIG. 1BD also shows the second fluid 274 being transferred from the second syringe reservoir 284 to the second reservoir interior volume 242.

A user of the fluid transfer system may attempt to transfer the first fluid 262 contained within the first syringe hub assembly 390 into the second pump reservoir 238 244. Similarly, the user may attempt transfer the second fluid 274 contained within the second syringe hub assembly 392 into the first pump reservoir 218. The user might also incorrectly attempt to couple the second vial adapter assembly 268 to the first vial reservoir 256, or incorrectly attempt to couple the first vial adapter assembly 258 to the second vial reservoir 270. With this in mind, the multiple fluid transfer interfaces used may be configured such that mechanical incompatibilities between interfaces which are not intended to be coupled prevent the creation of an incorrect fluid communication junction between two respective reservoirs.

Figure 17A:
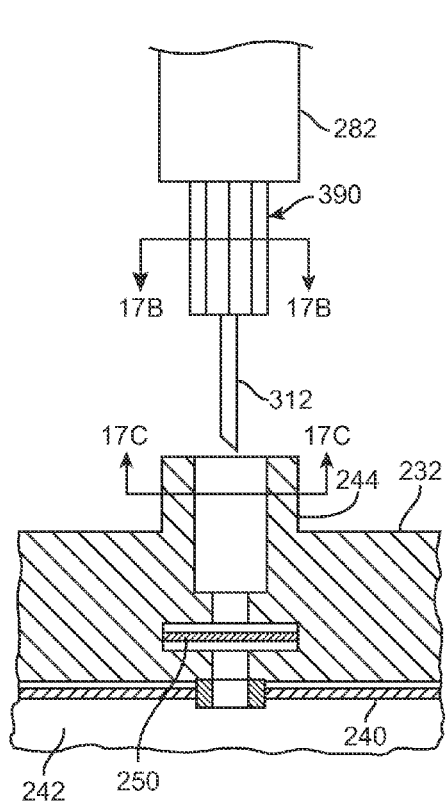
FIG. 17A shows the second keyed port embodiment of the dual reservoir cartridge of FIG. 14C and the coupled first syringe reservoir embodiment and first hub assembly embodiment of FIG. 13D.
Figure 17B:
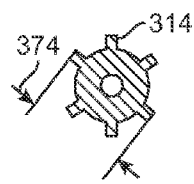
FIG. 17B is a view in transverse section of the first hub assembly embodiment of FIG. 17A.
Figure 17C:
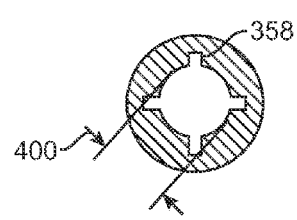
FIG. 17C is a view in transverse section of the second keyed port embodiment of FIG. 17A.
Figure 17D:
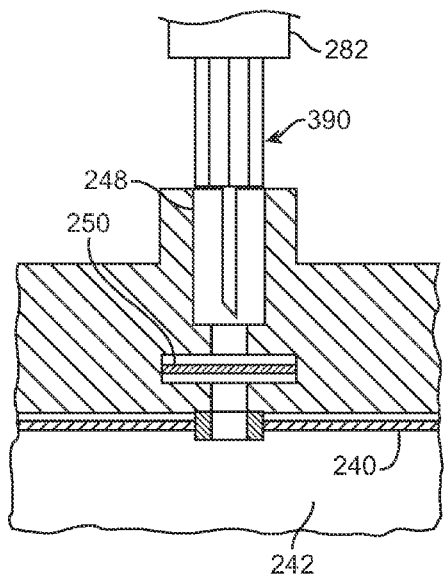
FIG. 17D illustrates an embodiment of the mechanical incompatibility between the first hub assembly embodiment of FIG. 17A and the second keyed port embodiment of FIG. 17A.

In particular, a comparison of FIG. 17B and FIG. 17C shows that the first hub key feature embodiment 314 is mechanically incompatible with the second port key feature embodiment 358. More specifically, the first hub key feature 314 includes 6 oblong bosses and the second port key feature 358 includes 4 oblong slots. Thus, as illustrated in FIG. 17D, an attempt to insert the first syringe hub assembly 390 into the second keyed port 244 will result in the failure of the first hub body 306 to enter the second channel 248. This is because the first hub key feature diameter 374 is larger than the second channel diameter 400. As a result, as shown in FIG. 17D the first needle 312 does not penetrate the second reservoir septum 250 and therefore no fluid communication junction is created.

Figure 18B:
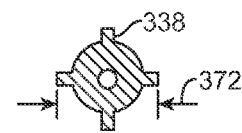
FIG. 18B is a view in transverse section of the second hub assembly embodiment of FIG. 18A.
Figure 18C:
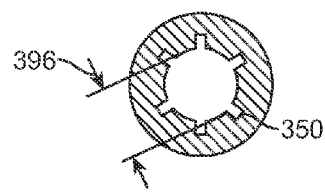
FIG. 18C is a view in transverse section of the first keyed port embodiment of FIG. 18A.
Figure 18A:
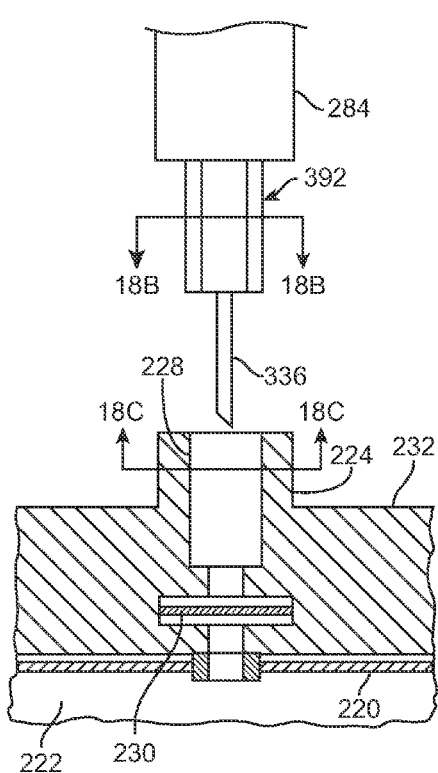
FIG. 18A shows the first keyed port embodiment of the dual reservoir cartridge of FIG. 14C and the coupled second syringe reservoir and second hub assembly embodiment of FIG. 13D.
Figure 18D:
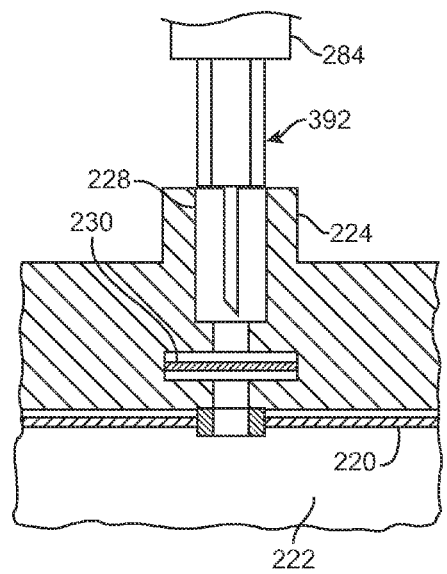
FIG. 18D illustrates an embodiment of the mechanical incompatibility between the second hub assembly embodiment of FIG. 18A and the first keyed port embodiment of FIG. 18A.

FIG. 18A shows the second syringe hub assembly 392 and the first keyed port 224. A comparison of FIGS. 18B and 18C shows that the second hub key feature embodiment 338 is mechanically incompatible with the first port key feature embodiment 350. The second hub key feature 338 comprises four oblong bosses and the second port key feature 350 includes six oblong slots. Thus, as illustrated in FIG. 18D, an attempt to insert the second syringe hub assembly 392 into the first keyed port 224 will result in the failure of the second hub body 330 to enter the first channel 228. This is because the second hub key feature diameter 372 is larger than the first channel diameter 396. As a result, as shown in FIG. 18D the second needle 336 does not penetrate the first reservoir septum 230 and therefore no fluid communication junction is created.

Figure 19A:
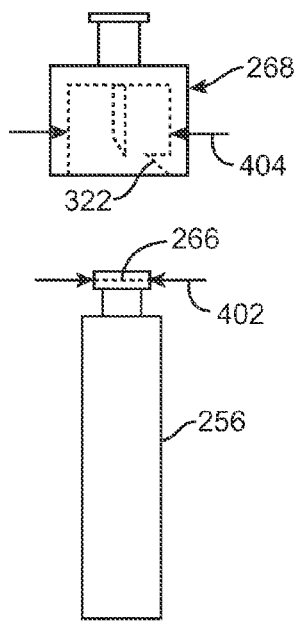
FIG. 19A illustrates an embodiment of the mechanical incompatibility between the first vial reservoir embodiment of FIG. 13A and the second vial adapter assembly embodiment of FIG. 13A.

FIG. 19A shows the second vial adapter assembly 268 of FIG. 10C and the first vial reservoir 256 of FIG. 10B. As shown in FIG. 19A, the two embodiments are mechanically incompatible because the exterior transverse diameter 402 of the first spigot port 264 of the first vial reservoir 256 does not match the interior transverse diameter 404 of the second distal cavity 342 of the second vial adapter assembly 268. Therefore, a mechanical coupling by the user between these two embodiments is impractical. The second hooked clip 346 would not engage the first spigot port 264, therefore the second hub assembly 326 could not be separated from the second vial adapter 328 after the first vial reservoir 256 and second vial adapter assembly 268 have been coupled. Therefore, a mechanical coupling by the user between these two embodiments is impractical.

Figure 19B:
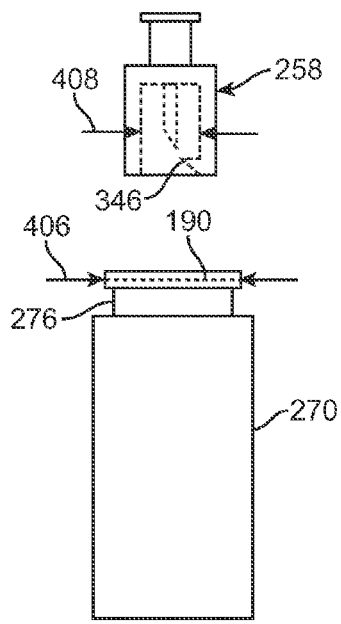
FIG. 19B illustrates an embodiment of the mechanical incompatibility between the second vial reservoir embodiment of FIG. 13A and the first vial adapter assembly embodiment of FIG. 13A.

The first vial adapter assembly 258 of FIG. 10B and the second vial reservoir 270 of FIG. 10C are mechanically incompatible because the exterior transverse diameter 406 of the second spigot port 276 of the second vial reservoir 270 is too large to insert into the interior transverse diameter 408 of the first distal cavity 318 as shown in FIG. 19B. The second spigot port 276 could not be inserted into the first distal cavity 318 so the first needle 312 can not penetrate the second vial septum 190. Therefore, a mechanical coupling by the user between these two embodiments is prohibited.

Figure 20A:
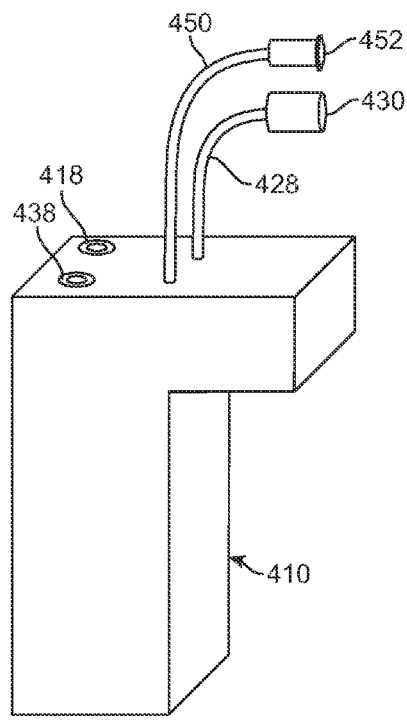
FIG. 20A is a perspective view of a multiple input and multiple output dual reservoir cartridge embodiment.

FIGS. 20A-20D show the components of a fluid transfer system embodiment. FIG. 20A shows a multiple reservoir cartridge embodiment 410 which may include a first pump reservoir 412 (as shown in FIG. 20M) which has a first pump reservoir body 414 having a first reservoir interior volume 416 which is disposed within the first reservoir body 414. The first pump reservoir body 414 may be fabricated from a thin flexible material. The first pump reservoir 412 may also include a first input port 418 which has a first channel 420 that is in fluid communication with the first reservoir interior volume 416. The first input port 418 may also include a first septum 422 that is disposed within a multiple reservoir cartridge body 424 and which seals the first channel 420. The first pump reservoir 412 may also include a first output port 426 which has a first fluid line 428 that is in fluid communication with the first reservoir interior volume 416, and a first output port adapter 430 which is secured to and in fluid communication with the first fluid line 428.

The multiple reservoir cartridge of FIG. 20A may also include second pump reservoir 432 (as shown in FIG. 20M) which may have a second pump reservoir body 434 having a second reservoir interior volume 436 which is disposed within the second pump reservoir body 434. The second pump reservoir body 434 may be comprised of a thin flexible material. The second pump reservoir 432 may also include a second input port 438 which has a second channel 440 which is in fluid communication with the second reservoir interior volume 436. A second septum 442 is disposed within the multiple reservoir cartridge body 424 and seals the second channel 440, and a port key feature 444 is disposed on a perimeter 446 of the second channel 440. The second pump reservoir 432 may also include a second output port 448 comprising a second fluid line 450 which is in fluid communication with the second reservoir interior volume 436, and a second output port adapter 452 which is secured to and in fluid communication with the second fluid line 450.

Figure 20B:
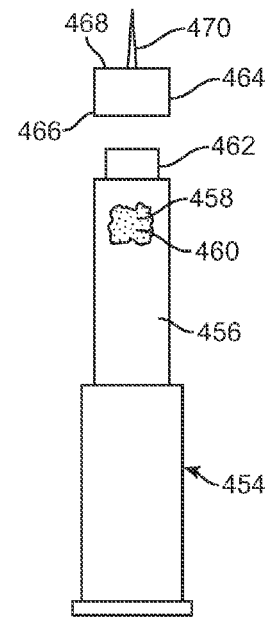
FIG. 20B shows embodiments of a diabetic pen reservoir and a bayonet needle.

FIG. 20B shows a diabetic pen reservoir 454 which may include a diabetic pen reservoir body 456 which has a pen interior volume disposed 458 within it. A first fluid 460 may be contained within the pen interior volume 458. The diabetic pen reservoir 454 may also include a pen port 462 which is in fluid communication with the pen interior volume 458. FIG. 20B also shows a bayonet needle adapter 464 which has a proximal section 466 that is capable of mating with the pen port 462 and a distal section 468 that is sealingly secured to a bayonet needle 470.

Figure 20C:
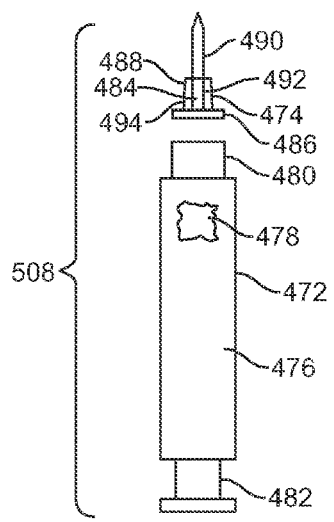
FIG. 20C shows embodiments of a syringe reservoir and a hub assembly.

A syringe reservoir 472 and a hub assembly 474 are shown in FIG. 20C. The syringe reservoir 472 may include a syringe body 476 which may have a syringe interior volume 478 disposed within the syringe body 476. The syringe reservoir 472 may also include a syringe port 480 and a plunger 482 which may be slidingly sealed to an inner bore of the syringe reservoir and when manipulated can vary the volume of the syringe interior volume 478 and thereby draw a fluid into or out of the syringe interior volume 478.

Figure 20D:
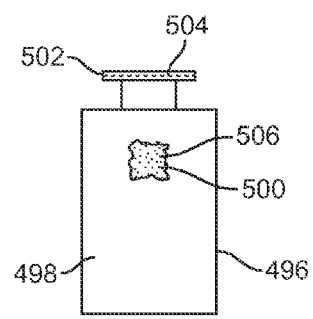
FIG. 20D shows a vial reservoir embodiment.
Figure 20E:
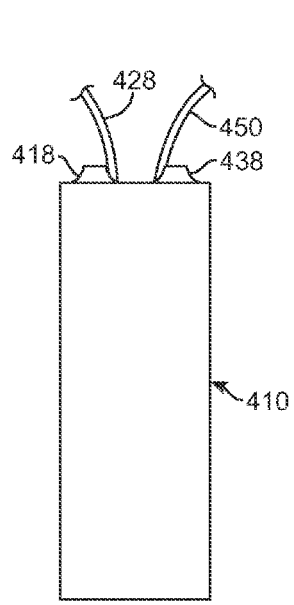
FIG. 20E is a front view of the dual reservoir cartridge embodiment of FIG. 20A.
Figure 20F:
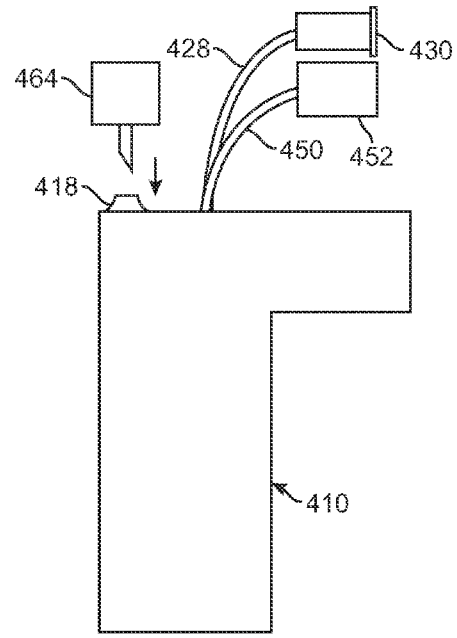
FIG. 20F is a side view of the dual reservoir cartridge embodiment of FIG. 20A.
Figure 20G:
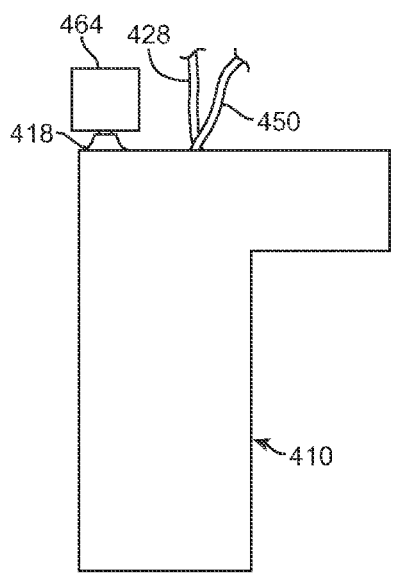
FIG. 20G depicts the bayonet needle embodiment of FIG. 20B inserted into a first port of the dual reservoir cartridge embodiment of FIG. 20A.
Figure 20H:
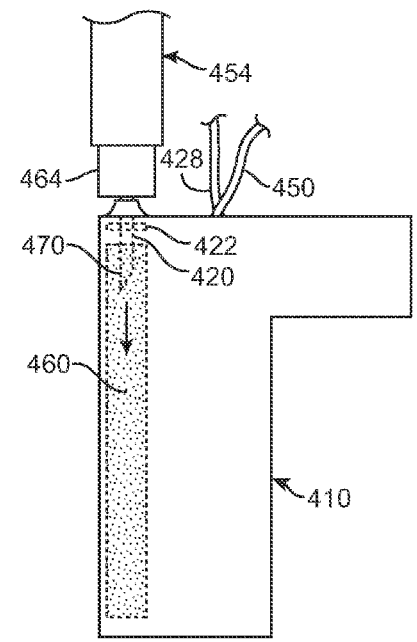
FIG. 20H depicts the diabetic pen reservoir embodiment of FIG. 20B coupled to the bayonet needle embodiment of FIG. 20G.

FIG. 20C also shows the hub assembly 474 which may include a hub body 484 having a proximal section 486 which is configured for coupling to the syringe port 480, and a distal section 488 of the hub body 484 which is sealingly secured to a tubular needle 490 having an inner lumen extending along a length thereof. The needle 490 may be configured to pierce the second septum 442 in order to create a second fluid communication junction between the syringe interior volume 478 and the second reservoir interior volume 436, but may also be configured to be mechanically incompatible with the second output port adapter 452 so as to prevent the creation of a fluid communication junction between the two components. The hub assembly 474 may also include a hub key feature 492 which is disposed on a perimeter 494 of the hub body 484, and which is mechanically compatible with the second input port 438, but is mechanically incompatible with the first input port 418. FIG. 20D shows a vial reservoir 496 which may have a vial reservoir body 498, and a vial interior volume 500 disposed within the vial reservoir body 498. The vial reservoir 496 may have a spigot port 502, and a vial septum 504 which may be disposed within the spigot port 502 and which seals the vial interior volume 500. The vial interior volume 500 may contain a second fluid 506.

FIGS. 20E-21B illustrate a fluid transfer method for a fluid transfer system embodiment. The method may include inserting the tubular bayonet needle 470 into the first channel 420 such that it penetrates the first septum 422 as shown in FIGS. 20F-20H. The method may also include creating a first fluid communication junction between the first pump reservoir 412 and the diabetic pen reservoir 454 by coupling the pen port 462 of the diabetic pen reservoir 454 to the bayonet needle adapter 464 as shown in FIG. 20H. The bayonet needle adapter 464 is releasably secured to the diabetic pen reservoir 454. The first fluid 460 may then be transferred from the diabetic pen reservoir 454 to the first pump reservoir 412 through the first fluid communication junction as is also shown in FIG. 20H.

Figures 20I, 20J:
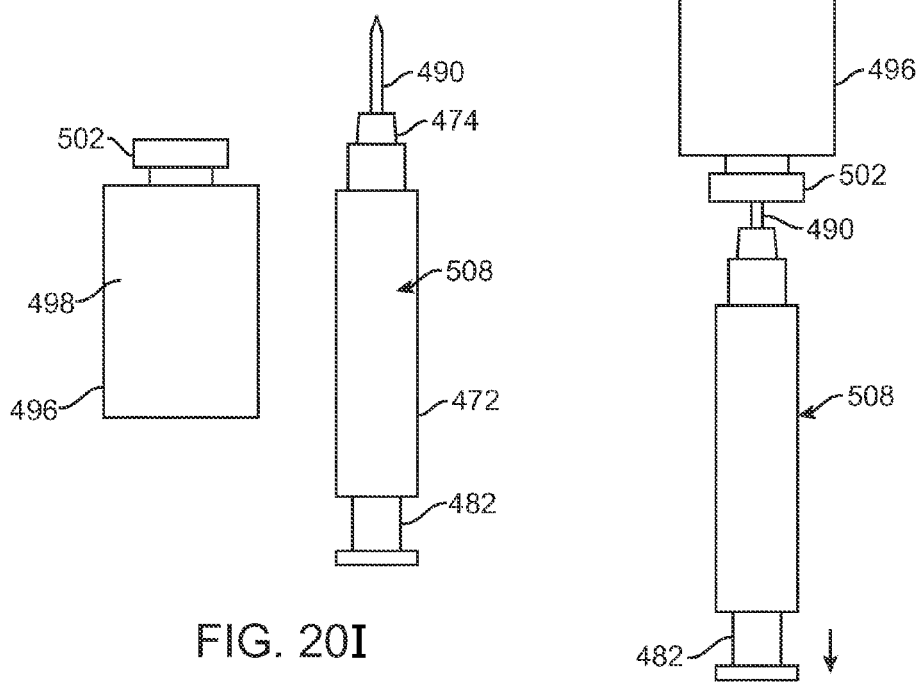
FIG. 20I shows the vial adapter embodiment of FIG. 20 D and the syringe reservoir and hub assembly embodiments of FIG. 20C coupled together.
FIG. 20J shows the needle of the hub assembly embodiment of FIG. 20C inserted into a spigot port of the vial reservoir embodiment of FIG. 20D.

FIG. 20I shows the vial reservoir 496 of FIG. 20D. FIG. 20I also shows the hub assembly 474 and syringe reservoir 472, both of FIG. 20C, coupled together to form the syringe hub assembly 508. The hub assembly 474 is releasably secured to the syringe reservoir 472. FIG. 20J shows the tubular needle 490 of the syringe hub assembly 508 having penetrated the vial septum 504 (not shown) of the vial reservoir 496, thereby forming a fluid communication junction between the vial interior volume 400 (not shown) and the syringe interior volume 478 (not shown) through an inner lumen of the tubular needle 490. FIG. 20J also shows the plunger 482 of the syringe reservoir 472 being drawn back in order to transfer the second fluid 506 form the vial reservoir 496 to the syringe reservoir 472.

Figures 20K, 20L:
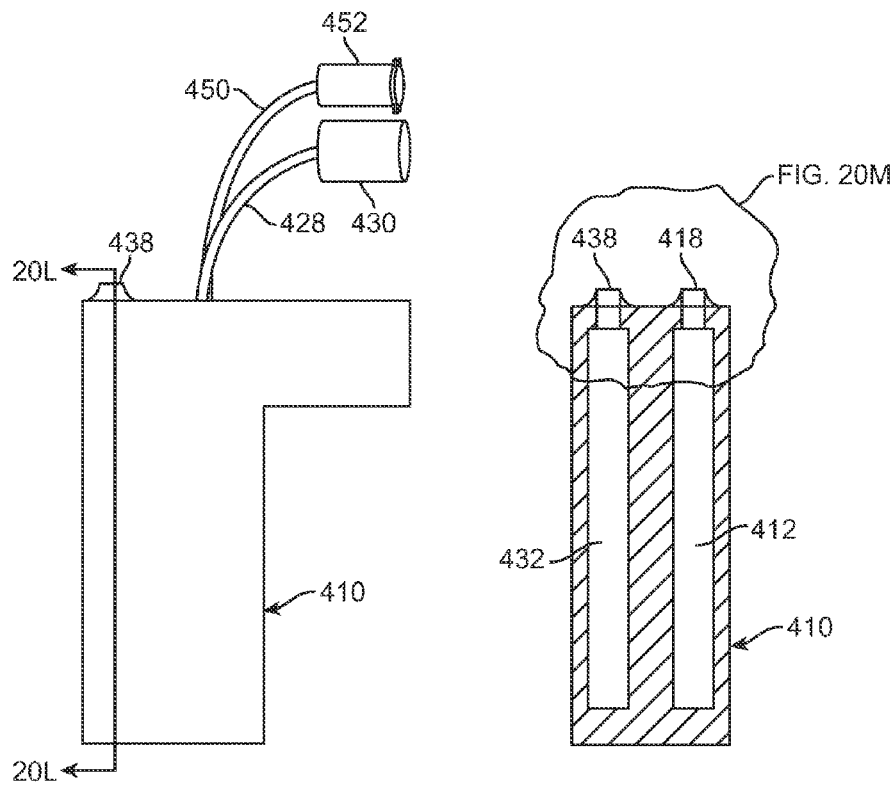
FIG. 20K shows the dual reservoir cartridge embodiment of FIG. 20A.
FIG. 20L is a view in transverse section of the dual reservoir cartridge embodiment of FIG. 20A.
Figure 20M:
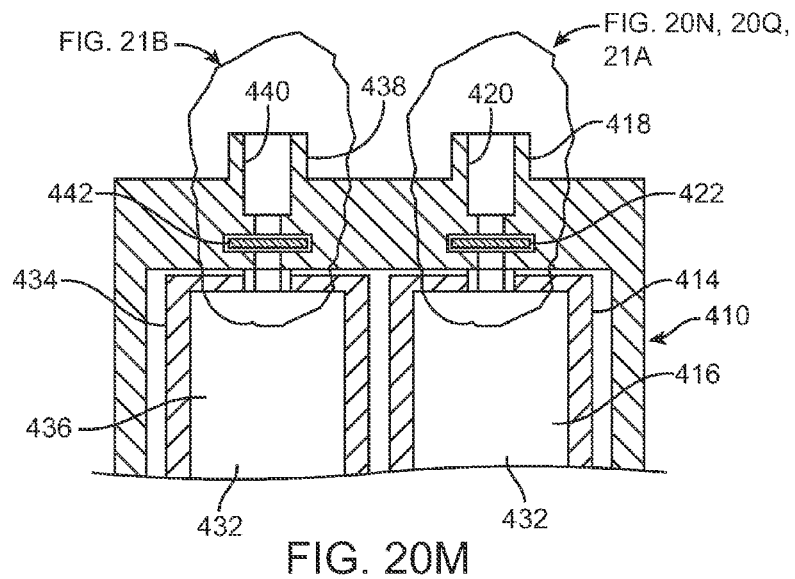
FIG. 20M is an enlarged view of the dual reservoir cartridge embodiment of FIG. 20L.

FIGS. 20K-20M show the multiple reservoir cartridge 410 of FIG. 20A. FIG. 20L is a sectional view of FIG. 20K. FIG. 20M is an enlarged view of FIG. 20L the purpose of which is to show detailed sectional views of the first input port 418 and the second input port 438. FIG. 20N shows the syringe hub assembly 508 and the second input port 438. FIG. 20O is a cross sectional view of the hub body 484, and FIG. 20P is a cross sectional view of the second input port 438. FIG. 20O shows the hub key feature 492 which consists of an array of oblong bosses 510 which run parallel to a hub central axis 512. FIG. 20O also shows a hub body diameter 518 and hub key feature diameter 520. FIG. 20P shows the port key feature 444 which consists of an array of oblong slots 514 which run parallel to a second channel central axis 516. FIG. 20P also shows a second channel diameter 522 and a port key feature diameter 524. FIG. 20O depicts the syringe hub assembly 508 inserted into the second input port 438. The axial alignment and circumferential spacing of the array of oblong bosses 510 which comprise the hub key feature 492 and the matching circular array of oblong slots 514 which comprise the port key feature 444 allows for the insertion of the hub assembly 474 into the second input port 438, with each boss 510 sliding within a respective slot 514. Also, the second channel diameter 522 is configured to allow for the insertion of the hub body 484 having a hub body diameter 518. As shown in FIG. 20Q, the tubular needle 490 has penetrated the second septum 442 thus creating a second fluid communication junction between the syringe reservoir 472 and the second reservoir interior volume 436 through an inner lumen of the tubular needle 490. FIG. 20Q also shows the second fluid 506 being transferred from the syringe reservoir 472 to the second reservoir interior volume 436.

As exemplified in the method described in connection with, e.g., FIGS. 20A-20Q, there may be mechanical compatibilities and mechanical incompatibilities designed into the various port interfaces which are used to transfer the fluids between the respective reservoirs. The purpose of the mechanical incompatibilities is to prevent the user from transferring the first fluid 460 from the diabetic pen reservoir 454 to the second pump reservoir 432, and/or from transferring the second fluid 506 from the syringe reservoir 472 to the first pump reservoir 412.

FIGS. 21A and 21B illustrate some mechanical incompatibility embodiments configured into the port interfaces for the embodiments described in FIGS. 20A-20Q. In some cases the second output port adapter 452 of the fluid transfer system may be a female luer adapter as shown in FIG. 20A, and the pen port 462 may be a male luer adapter as shown in FIG. 20B. If a user attempts to transfer the first fluid 460 from the diabetic pen reservoir 454 into the second pump reservoir 432, the exterior transverse diameter 526 of the pen port 462 is too large to insert into the second channel 440 which has a second channel diameter 552. The ability to create a fluid communication junction between the diabetic pen reservoir 454 and the second input port 438 may be further hindered by the fact that the second reservoir septum 442 is located at a lower section of the second channel 440. The second reservoir septum 442 must be penetrated in order to access the second reservoir interior volume 436, and because the pen port 462 is too large to insert into the second channel 440 the second reservoir septum 442 can not come into contact with the pen port 462 and therefore the second reservoir septum 442 will remain intact. A fluid communication junction between the diabetic pen reservoir 454 and the second pump reservoir 432 is therefore prevented by the mechanical incompatibility between the pen port 462 and the second channel 440.

As shown in FIG. 21C, the hub body 484 incorporates the hub key feature 492 which has a hub key feature diameter 520. As shown in FIG. 21D, the first channel 420 of the first input port 418 does not have a corresponding key feature embodiment. Therefore, the hub body 484 can not be inserted into the first channel 420 of the first input port 418 as is shown in FIG. 21B. This is because the hub key feature diameter 520 is larger than the first channel diameter 528. This being the case, the tubular needle 490 of the hub assembly 474 can not puncture the first reservoir septum 422 of the first input port 418 and therefore no fluid communication junction can be established between an interior volume of the syringe reservoir 472 and the first pump reservoir 412.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

Certain embodiments of the technology are set forth in the claim(s) that follow(s).

What is claimed is:

1. A fluid transfer system, comprising:
    A. a first pump reservoir including:
        (i) a first pump reservoir body,
        (ii) a first reservoir interior volume disposed within the first pump reservoir body, the first reservoir interior volume being capable of containing fluid,
        (iii) an input port comprising a first reservoir septum disposed within the first pump reservoir body and being in fluid communication with the first reservoir interior volume, and
        (iv) a first output port in fluid communication with the first reservoir interior volume;
    B. a second pump reservoir including:
        (i) a second pump reservoir body,
        (ii) a second reservoir interior volume disposed within the second pump reservoir body, the second reservoir interior volume being capable of containing a fluid, and
        (iii) a second output port comprising a second output port adapter in fluid communication with the second reservoir interior volume;
    C. a syringe hub assembly comprising:
        (i) a syringe body,
        (ii) a syringe interior volume disposed within the syringe body,
        (iii) a first fluid contained within the syringe interior volume, and
        (iv) a hub assembly coupled to the syringe body, the hub assembly including a needle in fluid communication with the syringe interior volume, the needle capable of piercing the first reservoir septum in order to create a first fluid communication junction between the syringe interior volume and the first reservoir interior volume, the needle being mechanically incompatible with the second output port adapter so as to prevent a fluid communication junction therebetween; and
    D. a diabetic pen reservoir assembly including:
        (i) a diabetic pen reservoir body,
        (ii) a pen interior volume disposed within the diabetic pen reservoir body,
        (iii) a second fluid contained within the pen interior volume, and
        (iii) a diabetic pen reservoir adapter coupled to the diabetic pen reservoir body and in fluid communication with the pen interior volume, the diabetic pen reservoir adapter being capable of coupling with the second output port adapter in order to create a second fluid communication junction between the pen interior volume and the second reservoir interior volume, the diabetic pen reservoir adapter being mechanically incompatible with the input port so as to prevent a fluid communication junction therebetween.

2. The fluid transfer system of claim 1 wherein the second output port adapter comprises a male luer adapter and the diabetic pen reservoir adapter comprises a female luer adapter.

3. The fluid transfer system of claim 2 wherein the input port comprises a channel disposed within the pump reservoir body, the channel diameter being too small to accept the female luer adapter thereby preventing a fluid communication junction between the diabetic pen reservoir and the first pump reservoir.

4. A method for transferring fluids, comprising:
    a. creating a first fluid communication junction between a first pump reservoir and a syringe reservoir by a piercing a first reservoir septum of a first input port of the first pump reservoir with a needle of a syringe hub assembly, the needle being mechanically incompatible with a second adapter of a second output port of a second pump reservoir so as to prevent a fluid communication junction therebetween;
    b. transferring a first fluid from the syringe reservoir to the first pump reservoir through the first fluid communication junction;
    c. creating a second fluid communication junction between a second pump reservoir and a diabetic pen reservoir by coupling the second adapter of the second output port to a diabetic pen reservoir adapter, the diabetic pen reservoir adapter being mechanically incompatible with the first input port so as to prevent a fluid communication junction therebetween; and d. transferring a second fluid from the diabetic pen reservoir to the second pump reservoir through the second fluid communication junction.

5. The method of claim 4 wherein the second adapter comprises a male luer adapter and the diabetic pen reservoir adapter comprises a female luer adapter and wherein creating the second fluid communication junction includes coupling the male luer adapter to the female luer adapter.

6. The method of claim 5 wherein coupling the male luer adapter with the female luer adapter comprises coupling the male luer adapter with the female luer adapter which is too large to insert into a channel of the input port thereby preventing a viable fluid communication junction therebetween.

7. The method of claim 4 wherein piercing the first reservoir septum with the syringe reservoir needle comprises piercing the first reservoir septum with the syringe reservoir needle which has an outer transverse dimension which is too small to form a seal with an inner transverse dimension of the male luer adaptor thereby preventing a viable fluid communication junction therebetween.

8. A fluid transfer system, comprising:
A. a first pump reservoir including:
   (i) a first pump reservoir body,
   (ii) a first reservoir interior volume disposed within the first pump reservoir body, the first reservoir interior volume being capable of containing fluid,
   (iii) an input port comprising a first reservoir septum, the first reservoir septum sealing the first reservoir interior volume, and
   (iv) a first output port in fluid communication with the first reservoir interior volume;
B. a second pump reservoir including:
   (i) a second pump reservoir body,
   (ii) a second reservoir interior volume disposed within the second pump reservoir body, the second reservoir interior volume being capable of containing a fluid, and
   (iii) a second output port comprising a second output port adapter being in fluid communication with the second reservoir interior volume;
C. a syringe hub assembly comprising:
   (i) a first syringe body,
   (ii) a first syringe interior volume within the first syringe body,
   (iii) a first fluid contained within the first syringe interior volume, and
   (iv) a hub assembly coupled to the first syringe body, the hub assembly including a needle in fluid communication with the first syringe interior volume, the needle capable of piercing the first reservoir septum in order to create a first fluid communication junction between the first syringe interior volume and the first reservoir interior volume, the needle being mechanically incompatible with the second output port adapter so as to prevent a fluid communication junction therebetween; and
D. a second syringe reservoir comprising:
   (i) a second syringe body,
   (ii) a second syringe interior volume within the second syringe body,
   (iii) a second fluid contained within the second syringe interior volume, and
   (iv) a second syringe port in fluid communication with the second syringe interior volume, the second syringe port capable of coupling to the second output port adapter in order to create a second fluid communication junction between the second syringe interior volume and the second reservoir interior volume, the second syringe port being mechanically incompatible with the input port so as to prevent a fluid communication junction therebetween.

9. The fluid transfer system of claim 8 wherein the second output port adapter comprises a female luer adapter and the pen port comprises a male luer adapter.

10. The fluid transfer system of claim 9 wherein the input port comprises a channel disposed within the pump reservoir body, the channel diameter being too small to accept the second syringe port thereby preventing a fluid communication junction between the diabetic pen reservoir and the second pump reservoir.

11. A method for transferring fluids comprising:
a. creating a first fluid communication junction between a first pump reservoir and a first syringe reservoir by piercing a first reservoir septum of a first input port of the first pump reservoir with a needle of a syringe hub assembly, the needle being mechanically incompatible with a second adapter of a second output port of a second pump reservoir so as to prevent a fluid communication junction therebetween;
b. transferring a first fluid from the first syringe reservoir to the first pump reservoir through the first fluid communication junction of the first syringe reservoir needle and the septum;
c. creating a second fluid communication junction between a second pump reservoir and a second syringe reservoir by coupling the second adapter with a syringe port of the second syringe reservoir, the syringe port being mechanically incompatible with the first input port so as to prevent a fluid communication junction therebetween; and
d. transferring a second fluid from the second syringe reservoir to the second pump reservoir through the fluid communication junction of the syringe port and the second adapter.

12. The method of claim 11 wherein the second adapter comprises a female luer adapter and the syringe port comprises a male luer adapter and wherein creating the second fluid communication junction includes coupling the female luer adapter to the male luer adapter.

13. The method of claim 12 wherein creating the second fluid communication junction includes coupling the female luer adapter with the male luer adapter which is too large to insert into the input port thereby preventing a viable fluid communication junction therebetween.

14. The method of claim 11 wherein piercing the first reservoir septum with the needle comprises piercing the first reservoir septum with the needle which has an outer transverse dimension which is too small to form a seal with an inner transverse dimension of the female luer adaptor thereby preventing a viable fluid communication junction therebetween.

15. A fluid transfer system, comprising:
A. a first vial adapter assembly including:
   1. a first hub assembly including:
      (i). a first hub comprising a first hub body, a proximal section capable of mating with a syringe port, and a first key feature disposed on a perimeter of the first hub body that is mechanically compatible with a first keyed port of a first receptacle reservoir and is mechanically incompatible with a second keyed port of a second receptacle reservoir; and (ii). a first needle comprising an elongate tubular member of high strength material including a sharpened distal end and a proximal end sealingly secured to the distal section of the first hub body; and
2. a first vial adapter including a first vial adapter body comprising a first distal cavity which has an inner transverse dimension configured to couple to a first spigot of a first vial reservoir but not couple to a second spigot port of a second vial reservoir and which includes a first hooked clip configured to engage the first spigot port but not the second spigot port, and
3. a first engagement feature which releasably secures the first hub body to the first vial adapter body such that the first needle of the first hub assembly may be disposed within and in axial alignment with the first distal cavity of the first vial adapter; and
B. A second vial adapter assembly comprising:
1. a second hub assembly including:
(i). a second hub comprising a second hub body, a proximal section capable of mating with a syringe port, and a second key feature disposed on a perimeter of the second hub body that is mechanically compatible with the second keyed port of the second receptacle reservoir and is mechanically incompatible with the first keyed port of the first receptacle reservoir, and
(ii). a second needle comprising an elongate tubular member of high strength material including a sharpened distal end and a proximal end sealingly secured to the distal section of the second hub body,
2. a second vial adapter including a second vial adapter body comprising a second distal cavity which has an inner transverse dimension configured to couple to a second spigot of a second vial reservoir but not couple to a first spigot port of a first vial reservoir and which includes a second hooked clip configured to engage the second spigot port but not the first spigot port, and
3. a second engagement feature which releasably secures the second hub body to the second vial adapter body such that the second needle of the second hub assembly may be disposed within and in axial alignment of the second distal cavity of the second vial adapter.

16. The fluid transfer system of claim 15 wherein the first hub body comprises a polymer.

17. The fluid transfer system of claim 15 wherein the second hub body comprises a polymer.

18. The fluid transfer system of claim 15 wherein the first needle comprises stainless steel.

19. The fluid transfer system of claim 15 wherein the second needle comprises stainless steel.

20. The coupling system of claim 15 wherein the first vial adapter comprises a polymer.

21. The fluid transfer system of claim 15 wherein the second vial adapter comprises a polymer.

22. The fluid transfer system of claim 15 wherein the first key feature comprises a plurality of elongated bosses disposed parallel to a longitudinal axis of the first needle lumen and spaced around a perimeter of the first hub body and the second key feature comprises a plurality of elongated bosses disposed parallel to a longitudinal axis of the second needle lumen and spaced around a perimeter of the second hub body.

23. The fluid transfer system of claim 15 wherein the first distal cavity comprises a substantially cylindrical configuration and the second distal cavity comprises a substantially cylindrical configuration.

24. The fluid transfer system of claim 15 wherein the first vial adapter body includes about 1 first hooked clip to about 3 first hooked clips and the second vial adapter body includes about 1 second hooked clip to about 3 second hooked clips.

25. The fluid transfer system of claim 15 wherein the first engagement feature comprises a break away rib connected between the first hub body and the first adapter body.

26. The coupling system of claim 15 wherein the second engagement feature comprises a break away rib connected between the second hub body and the second adapter body.

27. A method for transferring fluids, comprising:
A. providing a first vial adapter assembly, including:
1. a first hub having a tubular needle extending therefrom and a first key feature which is mechanically compatible with a first keyed port of a first pump reservoir and which is mechanically incompatible with a second keyed port of a second pump reservoir,
2. a first vial adapter including a first distal cavity which is configured to couple to a first spigot of a first vial reservoir but mechanically incompatible with a second spigot port of a second vial reservoir, and
3. a first engagement feature which releasably secures the hub to the first vial adapter with the tubular needle disposed within the first distal cavity;
B. providing a first vial reservoir including a first vial internal volume containing a first fluid, a first spigot port in fluid communication with the first vial internal volume, and a first vial septum disposed within and sealing the first spigot port;
C. providing a second vial adapter assembly, including:
1. a second hub having a tubular needle extending therefrom and a second key feature which is mechanically compatible with the second keyed port of the first pump reservoir and which is mechanically incompatible with the first keyed port of the second pump reservoir,
2. a second vial adapter including a second distal cavity which is configured to couple to the second spigot of the second vial reservoir but mechanically incompatible with the first spigot port of the first vial reservoir, and
3. a second engagement feature which releasably secures the second hub to the second vial adapter with the tubular needle disposed within the second distal cavity;
D. providing a second vial reservoir including a second vial internal volume containing a second fluid, a second spigot port in fluid communication with the second vial internal volume, and a second vial septum disposed within and sealing the second spigot port;
E. coupling the first vial adapter assembly to the first vial reservoir by inserting the first spigot port into the first distal cavity such that the first tubular needle punctures the first vial septum and such that the first vial adapter assembly is mechanically captured to the first vial reservoir;
F. coupling a first syringe to the first hub;
G. transferring the first fluid from the first vial reservoir to a first syringe reservoir of the first syringe through a lumen of the first tubular needle;
H. detaching the first hub from the first vial adapter by disengaging the first engagement feature;

I. coupling the second vial adapter assembly to the second vial reservoir by inserting the second spigot port into the second distal cavity such that the second tubular needle punctures the second vial septum and such that the second vial adapter assembly is mechanically captured to the second vial reservoir;

J. coupling a second syringe to the second hub;

K. transferring the second fluid from the second vial reservoir to a second syringe reservoir of the second syringe through a lumen of the second tubular needle; and L. detaching the second hub from the second vial adapter by disengaging the second engagement feature.

28. The method of claim 27 wherein coupling the first vial adapter assembly to the first vial reservoir by inserting the first spigot port into the first distal cavity comprises inserting the first spigot port which has a diameter which is too small to form a seal with the second distal cavity thereby preventing the creation of a fluid communication junction therebetween into the first distal cavity.

29. The method of claim 27 wherein coupling the second vial adapter assembly to the second vial reservoir by inserting the second spigot port into the second distal cavity comprises inserting the second spigot port which has a diameter which is too large to fit within the second distal cavity thereby preventing the creation of a fluid communication junction therebetween into the second distal cavity.

30. A fluid transfer system, comprising:
A. a first hub assembly including:
  (i). a first hub comprising:
    a. a first hub body including a proximal section configured to mate with a syringe port, and
    b. a first hub key feature which is disposed on a perimeter of the first hub body, which is configured to couple to a first keyed port of a first receptacle reservoir but which is mechanically incompatible with a second keyed port of a second receptacle reservoir, and
  (ii). a first needle comprising an elongate tubular member of high strength material, a sharpened distal end and a proximal end sealingly secured to a distal section of the first hub body;
B. a first keyed port in fluid communication with an interior volume of a first receptacle reservoir, comprising:
  (i). a first channel which is in fluid communication with an interior volume of a first receptacle reservoir and which is configured to accommodate insertion of the first hub body,
  (ii). a first septum disposed within and sealing the first channel at a depth substantially equal to or greater than a distance that the first needle extends from the first hub, and
  (iii). a first port key feature which is disposed on an inner perimeter of the first channel, which is configured to couple with the first hub key feature but which is mechanically incompatible with a second hub key feature;
C. a second hub assembly including:
  (i). a second hub comprising:
    a. a second hub body including a proximal section configured to mate with a syringe port, and
    b. a second hub key feature which is disposed on a perimeter of the second hub body, which is configured to couple to a second keyed port of a second receptacle reservoir but which is mechanically incompatible with the first keyed port of the first receptacle reservoir, and
  (ii). a second needle comprising an elongate tubular member of high strength material, a sharpened distal end and a proximal end sealingly secured to a distal section of the second hub body; and
D. a second keyed port in fluid communication with an interior volume of a second receptacle reservoir, comprising:
  (i). a second channel which is in fluid communication with the interior volume of a second receptacle reservoir and which is configured to accommodate insertion of the second hub body,
  (ii). a second septum disposed within and sealing the second channel at a depth substantially equal to or greater than a distance that the second needle extends from the second hub, and
  (iii). a second port key feature which is disposed on an inner perimeter of the second channel, which is configured to couple with the second hub key feature but which is mechanically incompatible with the first hub key feature.

31. The fluid transfer system of claim 30 wherein the first hub key feature comprises a plurality of oblong bosses disposed parallel to a longitudinal axis of the first hub body and the first port key feature comprises a plurality of oblong slots which correspond in circumferential spacing to the circumferential spacing of these oblong bosses and which extend substantially parallel to a longitudinal axis of the first channel.

32. The fluid transfer system of claim 30 wherein the second hub key feature comprises a plurality of oblong bosses disposed parallel to a longitudinal axis of the second hub body and the second port key feature comprises a plurality of oblong slots which correspond in circumferential spacing to the circumferential spacing of these oblong bosses and which extend substantially parallel to a longitudinal axis of the second channel.

33. A fluid transfer system, comprising:
A. a first vial adapter assembly comprising:
  1. a first hub assembly including:
    (i). a first hub comprising:
      a. a first hub body,
      b. a proximal section capable of mating with a syringe port, and
      c. a first hub key feature which is disposed on a perimeter of the first hub body, which is mechanically compatible with a first keyed port of a first receptacle reservoir and which is mechanically incompatible with a second keyed port of a second receptacle reservoir; and
    (ii). a first needle comprising an elongate tubular member of high strength material including a sharpened distal end and a proximal end sealingly secured to the distal section of the first hub body; and
  2. a first vial adapter including:
    (i). a first vial adapter body, and
    (ii). a first distal cavity which has an inner transverse dimension configured to couple to a first spigot of a first vial reservoir but not couple to a second spigot port of a second vial reservoir, the first distal cavity including a hooked clip configured to engage a first spigot port but not a second spigot port, and
  3. a first engagement feature which releasably secures the first hub body to the first vial adapter body such that the first needle of the first hub assembly is disposed within and in axial alignment with the first distal cavity of the first vial adapter;

B. a first vial reservoir comprising a first vial reservoir body, a first vial internal volume disposed within the vial reservoir body, a first spigot port in fluid communication with the first vial internal volume, a first vial septum disposed within the first spigot port, and a first fluid disposed within the first vial internal volume;

C. a first receptacle reservoir comprising an interior volume and a first keyed port including a first channel in fluid communication with the interior volume of the receptacle reservoir, a first septum which is disposed within and seals the first channel at a depth which is greater than or equal to a distance which the first needle extends from the first hub body and a first port keyed feature which is disposed on a perimeter of the first channel and mechanically compatible with the first hub key feature;

D. a second vial adapter assembly comprising:
 1. a second hub assembly including:
  (i). a second hub comprising:
   a. a second hub body,
   b. a proximal section capable of mating with a syringe port, and
   c. a second hub key feature which is disposed on a perimeter of the second hub body, which is mechanically compatible with a second keyed port of a second receptacle reservoir and which is mechanically incompatible with the first keyed port of the first receptacle reservoir; and
  (ii). a second needle comprising an elongate tubular member of high strength material including a sharpened distal end and a proximal end sealingly secured to the distal section of the second hub body; and
 2. a second vial adapter including:
  (i). a second vial adapter body, and
  (ii). a second distal cavity which has an inner transverse dimension configured to couple to a second spigot of a second vial reservoir but not couple to the first spigot port of the first vial reservoir, the second distal cavity including a second hooked clip configured to engage the second spigot port but not the first spigot port, and
 3. a second engagement feature which releasably secures the second hub body to the second vial adapter body such that the second needle of the second hub assembly may be disposed within and in axial alignment with the second distal cavity of the second vial adapter;

E. a second vial reservoir comprising a second vial reservoir body, a second vial internal volume disposed within the second vial reservoir body, a second spigot port in fluid communication with the second vial internal volume, a second vial septum disposed within the second spigot port, and a second fluid disposed within the second vial internal volume; and F. a second receptacle reservoir comprising an interior volume and a second keyed port including a second channel in fluid communication with the interior volume of the second receptacle reservoir, a second septum which is disposed within and seals the second channel at a depth which is greater than or equal to a distance which the second needle extends from the second hub body and a second port keyed feature which is disposed on a perimeter of the second channel and mechanically compatible with the second hub key feature.

34. A fluid transfer system, comprising:
A. a first pump reservoir including:
 (i) a first reservoir body,
 (ii) a first reservoir interior volume which is disposed within the first reservoir body and which is capable of containing fluid,
 (iii) a first input port including a first channel which is in fluid communication with the first reservoir interior volume, a first septum disposed within and sealing the first channel and a tubular bayonet needle inserted through the first septum such that an inner lumen of the first bayonet needle is in fluid communication with the first interior volume, and
 (iv) a first output port comprising a first fluid line which is in fluid communication with the first interior volume and a first output port adapter which is secured to and in fluid communication with the first fluid line;
B. a second pump reservoir including:
 (i) a second reservoir body,
 (ii) a second reservoir interior volume which is disposed within the second reservoir body and which is capable of containing fluid,
 (iii) a second input port including a second channel which is in fluid communication with the second reservoir interior volume, a second septum disposed within and sealing the second channel, and a key feature disposed on a perimeter of the second channel, and
 (iv) a second output port comprising a second fluid line which is in fluid communication with the second interior volume and a second output port adapter which is secured to and in fluid communication with the second fluid line;
C. a diabetic pen reservoir assembly including:
 (i) a diabetic pen reservoir body;
 (ii) a pen interior volume disposed within the diabetic pen reservoir body;
 (iii) a first fluid contained within the pen interior volume; and
 (iv) a pen port which is in fluid communication with the pen interior volume, which is configured to couple to the bayonet needle in order to create a second fluid communication junction between the pen interior volume and the first interior volume and which is mechanically incompatible with the first channel of the first input port so as to prevent a fluid communication junction therebetween; and
D. a syringe hub assembly comprising:
 (i) a syringe including a syringe body, a syringe interior volume disposed within the syringe body, a second fluid contained within the syringe interior volume and a syringe port; and
 (ii) a hub assembly comprising:
  a. a hub body including a proximal section secured to a syringe port of the syringe;
  c. a hub key feature which is disposed on a perimeter of the hub body, which is mechanically compatible with the second input port so as to allow for the coupling of the hub assembly to the second input port and which is mechanically incompatible with the first input port; and
  d. a tubular needle which includes an inner lumen in fluid communication with the syringe interior volume, which is configured to pierce the second reservoir septum in order to create a second fluid communication junction between the syringe interior volume and the second interior volume and which is mechanically incompatible with the second output port adapter so as to prevent a fluid communication junction therebetween.

35. The fluid transfer system of claim 34 wherein the second output port adapter comprises a female luer adapter and the pen port comprises a male luer adapter.

36. A method for transferring fluids, comprising:
a. creating a first fluid communication junction between a first pump reservoir and a diabetic pen reservoir by coupling a diabetic pen adapter of the diabetic pen reservoir, which is mechanically incompatible with a second keyed input port, to a bayonet needle adapter which is secured to the first pump reservoir and which includes a bayonet needle disposed through a first reservoir septum of a first port of the first pump reservoir;
b. transferring a first fluid from the diabetic pen reservoir to the first pump reservoir through the first fluid communication junction;
c. inserting a keyed hub assembly coupled to a syringe reservoir, which is mechanically incompatible with the first input port, into the second keyed input port of a second pump reservoir such that a hub needle of the keyed hub assembly penetrates a second reservoir septum which seals the second pump reservoir thereby creating a second fluid communication junction between the second pump reservoir and the syringe reservoir; and
d. transferring a second fluid from the syringe reservoir to the second pump reservoir through the second fluid communication junction.

37. The method of claim 36 wherein the bayonet needle adapter comprises a male luer adapter and the diabetic pen reservoir adapter comprises a female luer adapter and wherein creating the first fluid communication junction includes coupling the male luer adapter to the female luer adapter.

38. The method of claim 37 wherein creating the first fluid communication junction includes coupling the male luer adapter with the female luer adapter which is too large to insert into the second keyed port thereby preventing a viable fluid communication junction therebetween.

39. The method of claim 36 wherein creating the second fluid communication junction includes piercing the second reservoir septum with the hub needle including an outer transverse dimension which is too small to form a seal with an inner transverse dimension of the female luer adaptor of the bayonet needle thereby preventing a fluid communication junction therebetween.

* * * * *